(12) United States Patent
Alford

(10) Patent No.: US 10,758,571 B1
(45) Date of Patent: *Sep. 1, 2020

(54) PROCESSES FOR MAKING AND USING A MESENCHYMAL STEM CELL DERIVED SECRETOME

(71) Applicant: Combangio, Inc., Menlo Park, CA (US)

(72) Inventor: Spencer Alford, Mountain View, CA (US)

(73) Assignee: COMBANGIO, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/785,470

(22) Filed: Feb. 7, 2020

Related U.S. Application Data

(60) Provisional application No. 62/831,371, filed on Apr. 9, 2019, provisional application No. 62/929,035, filed on Oct. 31, 2019.

(51) Int. Cl.

| | | |
|---|---|---|
| *A61K 38/18* | (2006.01) | |
| *A61K 38/57* | (2006.01) | |
| *A61K 38/20* | (2006.01) | |
| *A61K 38/17* | (2006.01) | |
| *A61K 35/28* | (2015.01) | |
| *A61K 45/06* | (2006.01) | |
| *A61P 27/02* | (2006.01) | |
| *A61K 47/02* | (2006.01) | |
| *A61K 47/26* | (2006.01) | |
| *A61K 47/38* | (2006.01) | |
| *A61K 38/36* | (2006.01) | |
| *A61K 47/10* | (2017.01) | |

(52) U.S. Cl.
CPC ............ *A61K 35/28* (2013.01); *A61K 38/177* (2013.01); *A61K 38/1709* (2013.01); *A61K 38/1833* (2013.01); *A61K 38/1866* (2013.01); *A61K 38/2053* (2013.01); *A61K 38/36* (2013.01); *A61K 38/57* (2013.01); *A61K 45/06* (2013.01); *A61K 47/02* (2013.01); *A61K 47/10* (2013.01); *A61K 47/26* (2013.01); *A61K 47/38* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 8,058,066 B2 | 11/2011 | Marshall et al. | |
| 8,088,732 B2 | 1/2012 | Marshall et al. | |
| 8,198,239 B2 | 6/2012 | Marshall et al. | |
| 8,318,665 B1 | 11/2012 | Marshall et al. | |
| 8,361,485 B2 | 1/2013 | Naughton et al. | |
| 8,530,418 B2 | 9/2013 | Marshall et al. | |
| 8,741,646 B2 | 6/2014 | Emig et al. | |
| 8,796,025 B2 | 8/2014 | Emig et al. | |
| 8,822,415 B2 | 9/2014 | Trumpower et al. | |
| 8,911,963 B2 | 12/2014 | Epstein et al. | |
| 9,029,146 B2 | 5/2015 | Lim et al. | |
| 9,173,927 B2 | 11/2015 | Emig et al. | |
| 9,192,632 B2 | 11/2015 | Johnstone et al. | |
| 9,636,364 B2 | 5/2017 | Brown et al. | |
| 9,856,455 B2 | 1/2018 | March et al. | |
| 9,980,987 B2 | 5/2018 | Brown et al. | |
| 2011/0003008 A1 | 1/2011 | Lim | |
| 2011/0206647 A1* | 8/2011 | Woda | A61P 9/00 424/93.7 |
| 2012/0276215 A1 | 11/2012 | Riordan et al. | |
| 2014/0079688 A1 | 3/2014 | Sing | |
| 2014/0242043 A1 | 8/2014 | Steed et al. | |
| 2014/0242142 A1 | 8/2014 | O'Brien et al. | |
| 2014/0255355 A1 | 9/2014 | Sing | |
| 2015/0017122 A1 | 1/2015 | Rolfo et al. | |
| 2015/0064273 A1 | 3/2015 | Peled et al. | |
| 2015/0190430 A1 | 7/2015 | Lim | |
| 2015/0250823 A1* | 9/2015 | Rolfo | A61K 38/2066 424/85.2 |
| 2015/0335712 A1 | 11/2015 | Brown et al. | |
| 2016/0145576 A1 | 5/2016 | March et al. | |
| 2016/0166619 A1 | 6/2016 | Harris et al. | |
| 2016/0220615 A1 | 8/2016 | Sing | |
| 2016/0324928 A1 | 11/2016 | Sing | |
| 2016/0361253 A1 | 12/2016 | Brown | |
| 2017/0035812 A1 | 2/2017 | Meyen, III et al. | |
| 2017/0080033 A1 | 3/2017 | Harris et al. | |
| 2017/0189449 A1 | 7/2017 | Lim | |
| 2017/0202919 A1 | 7/2017 | Steed et al. | |

(Continued)

FOREIGN PATENT DOCUMENTS

| | | |
|---|---|---|
| EP | 2054506 A1 | 5/2009 |
| EP | 2185197 B1 | 5/2010 |

(Continued)

OTHER PUBLICATIONS

Akpek, E. K., and J. D. Gottsch. "Immune Defense at the Ocular Surface." Eye (London, England) 17 (8): 949-56 (2003).
Baradaran-Rafii et al. Current and Upcoming Therapies for Ocular Surface Chemical Injuries. The Ocular Surface 15 (1): 48-64 (2017).
Brighton, et al., The Journal of Bone and Joint Surgery 73(6):832-47 (1991).
Chen et al., MK2 Inhibitor Reduces Alkali Burn-Induced Inflammation in Rat Cornea. Scientific Reports. (2016).
Choi et al., Effects of Amniotic Membrane Suspension in the Rat Alkali Burn Model. Molecular Vision 17 (February): 404-12. (2011).
Choi, H., et al., Curr Eye Res. 42(10):1348-1357 (2017).
Dietrich-Ntoukas et al. Cornea., 31(3):299-310 (2012).

(Continued)

*Primary Examiner* — Daniel C Gamett
(74) *Attorney, Agent, or Firm* — Morgan, Lewis & Bockius LLP; Christina A. MacDougall

(57) ABSTRACT

The present application provides methods and processes for making and using a mesenchymal stem cell secretome, as well as methods for treating ocular conditions and/disorders with the mesenchymal stem cell secretome described herein.

25 Claims, 20 Drawing Sheets

(56) References Cited

U.S. PATENT DOCUMENTS

| | | | |
|---|---|---|---|
| 2017/0209498 A1 | 7/2017 | Brown et al. | |
| 2017/0216366 A1 | 8/2017 | Rolfo et al. | |
| 2018/0187159 A1 | 7/2018 | March et al. | |
| 2018/0207091 A1 | 7/2018 | Brown | |
| 2018/0220642 A1 | 8/2018 | March et al. | |
| 2018/0271914 A1 | 9/2018 | Steed et al. | |
| 2018/0271916 A1 | 9/2018 | Brown et al. | |
| 2018/0280441 A1 | 10/2018 | Lee | |
| 2018/0327713 A1 | 11/2018 | Harris et al. | |
| 2019/0046576 A1* | 2/2019 | Gangaraju | A61K 9/0019 |

FOREIGN PATENT DOCUMENTS

| | | | |
|---|---|---|---|
| EP | 2254586 A1 | 12/2010 | |
| EP | 2451964 A1 | 5/2012 | |
| EP | 2723364 A1 | 4/2013 | |
| EP | 2617428 A1 | 7/2013 | |
| EP | 2793929 B1 | 10/2014 | |
| EP | 2814950 A1 | 12/2014 | |
| EP | 3224348 A1 | 10/2017 | |
| EP | 3233096 A2 | 10/2017 | |
| EP | 3279212 A1 | 2/2018 | |
| EP | 3317397 A1 | 5/2018 | |
| EP | 3328413 A1 | 6/2018 | |
| WO | WO 2006/060779 | 6/2006 | |
| WO | WO 2008/020815 | 2/2008 | |
| WO | WO 2009/025730 | 2/2009 | |
| WO | WO 2009/045359 | 4/2009 | |
| WO | WO 2009/105044 | 8/2009 | |
| WO | WO 2010/110768 | 9/2010 | |
| WO | WO 2011/006107 | 1/2011 | |
| WO | WO 2011/127090 | 10/2011 | |
| WO | WO 2012/175745 | 12/2012 | |
| WO | WO 2013093878 | 6/2013 | |
| WO | WO 2013/121427 | 8/2013 | |
| WO | WO 2015/179490 | 11/2015 | |
| WO | WO 2016/082882 | 6/2016 | |
| WO | WO 2016/083500 | 6/2016 | |
| WO | WO 2016/099949 | 6/2016 | |
| WO | WO 2016/159721 | 10/2016 | |
| WO | WO 2017/001649 | 1/2017 | |
| WO | WO 2017/019986 | 2/2017 | |
| WO | WO 2017/139795 | 8/2017 | |
| WO | WO 2017/164467 | 9/2017 | |
| WO | WO 2017/209658 | 12/2017 | |
| WO | WO 2017/217967 | 12/2017 | |
| WO | WO 2018/102174 | 6/2018 | |
| WO | WO 2018/131003 | 7/2018 | |
| WO | WO 2018/213795 | 11/2018 | |
| WO | WO 2019/016799 | 1/2019 | |

OTHER PUBLICATIONS

Epstein et al., "Corneal Neovascularization. Pathogenesis and Inhibition." Cornea 6 (4): 250-57 (1987).
Fernandes-Cunha et al., "Corneal Wound Healing Effects of Mesenchymal Stem Cell Secretome Delivered within a Viscoelastic Gel Carrier." Stem Cells Translational Medicine 8 (5): 478-89 (2019).
Ferreira et al., "Mesenchymal Stromal Cell Secretome: Influencing Therapeutic Potential by Cellular Pre-Conditioning." Frontiers in Immunology 9. (2018).
Fukuda K., Int J Mol Sci. 18(9) (2017).
Gao et al., Am J Pathol. 179(5):2243-53 (2011).
Gaudana R, Jwala J, Boddu SH, Mitra AK. "Recent perspectives in ocular drug delivery." Pharm Res. 26(5):1197-216 (2009).
Haring et al., JAMA Ophthalmol. 134(10):1119-1124 (2016).
Harkin et al. "Concise Reviews: Can Mesenchymal Stromal Cells Differentiate into Corneal Cells? A Systematic Review of Published Data." Stem Cells 33 (3): 785-91 (2015).
Jin, Y., et al., Mol Vis.;13:626-34 (2007).
Kaltz, et al., Exp Cell Res Oct. 1;316(16):2609-17 (2010).
Katzman and Jeng, "Management Strategies for Persistent Epithelial Defects of the Cornea." Saudi Journal of Ophthalmology : Official Journal of the Saudi Ophthalmological Society 28 (3): 168-72 (2014).
Kim et al., "PEP-1-FK506BP Inhibits Alkali Burn-Induced Corneal Inflammation on the Rat Model of Corneal Alkali Injury." BMB Reports 48 (11): 618-23 (2015).
Li, M. et al., Int Wound J. (1):64-73 (2017).
Maddula et al., "Horizons in Therapy for Corneal Angiogenesis." Ophthalmology 118 (3): 591-99 (2011).
McGwin and Owsley, "Incidence of Emergency Department—Treated Eye Injury in the United States." Archives of Ophthalmology 123 (5): 662-66 (2005).
Newell, Seminars in Immunopathology 33(2):91 (2011).
Samaeekia et al., Effect of Human Corneal Mesenchymal Stromal Cell-Derived Exosomes on Corneal Epithelial Wound Healing. Investigative Ophthalmology & Visual Science 59 (12): 5194-5200 (2018).
Schrage et al., "Use of an Amphoteric Lavage Solution for Emergency Treatment of Eye Burns. First Animal Type Experimental Clinical Considerations." Burns : Journal of the International Society for Burn Injuries 28 (8): 782-86 (2002).
Serrano et al., "Traumatic Eye Injuries: Management Principles for the Prehospital Setting." JEMS: A Journal of Emergency Medical Services 38 (12): 56 (2013).
Singh et al., "Ocular Chemical Injuries and Their Management." Oman Journal of Ophthalmology 6 (2): 83-86 (2013).
Stevenson, et al., Clin Ophthalmol. 7:2153-2158 (2013).
Trainor et al., Nature Biotechnology 32(8) (2014).
Turner, et al., J Neurosurg 118(5):1072-1085 (2013).
Van Stavern, et al., J Neuro-Ophthamol 21(2):112-117 (2001).
Vizoso et al., "Mesenchymal Stem Cell Secretome: Toward Cell-Free Therapeutic Strategies in Regenerative Medicine." International Journal of Molecular Sciences 18 (9): 1852 (2017).
White et al., J Allergy Clin Immunol Pract. 6(1):38-69 (2018).
Wirostko B, et al., Ocul Surf. Jul; 13(3): 204-21 (2015).
Yamagami S., et al., Invest Ophthalmol Vis Sci. 46(4):1201-7 (2005).
Zanotti et al., "Mouse Mesenchymal Stem Cells Inhibit High Endothelial Cell Activation and Lymphocyte Homing to Lymph Nodes by Releasing TIMP-1." Leukemia 30 (5): 1143-54. (2016).
Ziaei, Greene, and Green, "Wound Healing in the Eye: Therapeutic Prospects." Advanced Drug Delivery Reviews 126: 162-76 (2018).

* cited by examiner

| Protein ID | | Function |
|---|---|---|
| 1 | Serpin E1 | Corneal repair (26024123); anti-angiogenic (25378411) |
| 2 | Chitinase-3 like | Antimicrobial (26238714) |
| 3 | Apolipoprotein A1 | Wound healing (24705596) |
| 4 | Angiogenin | Cell proliferation/anti-apoptosis (22021078) |
| 5 | MIF | Reduces oxidative stress (12626594) |
| 6 | Pentraxin-3 | Tissue repair; fibrin remodeling (26763449) |

FIGURE 5A — FIGURE 5B
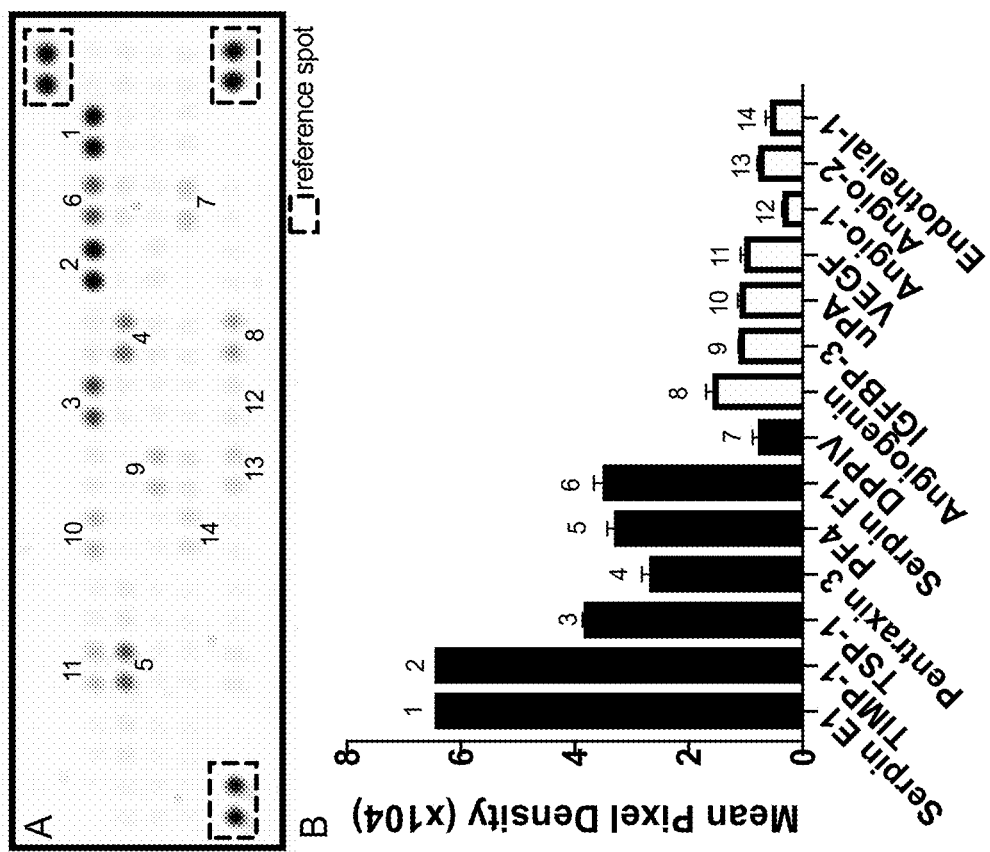

PROCESSES FOR MAKING AND USING A MESENCHYMAL STEM CELL DERIVED SECRETOME

CROSS REFERENCE TO RELATED APPLICATION

The present application claims priority to U.S. Provisional Application No. 62/831,371, filed Apr. 9, 2019; and U.S. Provisional Application No. 62/929,035 filed Oct. 31, 2019, the disclosures of which are hereby incorporated by reference in their entireties for all purposes.

BACKGROUND OF THE INVENTION

Regenerative medicine is an area of medicine that is concerned with the replacement or regeneration of human cells, tissues, or organs, in order to restore or establish normal functions. For example, stem cell therapies can be utilized in order to treat, prevent, or cure a variety of diseases and disorders.

Stem cells are cells that have the ability to divide without limit and that, under certain specific conditions, can differentiate into a variety of different cell types. Totipotent stem cells are stem cells that have the potential to generate all of the cells and tissues that make up an embryo. Pluripotent stem cells are stem cells that give rise to cells of the mesoderm, endoderm, and ectoderm. Multipotent stem cells are stem cells that have the ability to differentiate into two or more cell types, whereas unipotent stem cells are stem cells that differentiate into only one cell type. One type of such stem cells are mesenchymal stem cells. See, for example U.S. Patent Application US20190046576.

However, it is difficult to produce and store live stem cell-based therapies on a clinically relevant scale. (See, Trainor et al., *Nature Biotechnology* 32(1) (2014)). Moreover, the therapeutic potency and regenerative capacity of such therapies is often variable and the cells can die before or during transplantation. (See, Newell, Seminars in *Immunopathology* 33(2):91 (2011)). Implanted stem cells are also susceptible to host immune system attack and/or rejection, and it is often difficult to assess potency and/or control "dosing". Thus, there is a need in the art for additional regenerative therapies that can overcome the cost, storage, and manufacturing quality control limitations that are currently associated with cell-based regenerative medicine therapies. In particular in the context of ocular conditions.

Blast and blunt injuries to the eye can cause a series of mechanical disruptions to the ocular contents including commotio retinae, traumatic cataract, disruption of the zonular attachments to the lens, angle recession, iris dialysis, and rupture of the pupillary sphincter. Treatment of these injuries has been limited to mechanical repair (when possible) of the iris, replacement of the crystalline lens with plastic lens implants, and repair of retinal detachments. There has been no treatment to repair the cellular architecture of the retina or the anterior chamber. Furthermore, traumatic optic neuropathy and optic nerve avulsion are among the six leading types of ocular injury that required specialized ophthalmic care during Operation Iraqi Freedom (Cho and Savitsky, "Ocular Trauma Chapter 7", in Combat Casualty Care: Lessons learned from Oef and Oif, by Brian Eastbridge and Eric Savitsky, pp. 299-342, Ft. Detrick, Md.: Borden Institute (US) Government Printing Office, 2012), incorporated herein by reference in its entirety. Sixty percent of traumatic head injuries result in neuro-ophthalmic abnormalities (Van Stavern, et al., *J Neuro-Ophthamol* 21(2):112-117, 2001) (incorporated herein by reference in its entirety) half of which involve the optic nerves or visual pathways. Traumatic injury to neurons results in axonal damage and irreversible neuronal loss resulting in permanent deficits. While a number of potential neuroprotective therapies have been identified in animals, these single agents have generally failed to translate to therapies in human clinical trials (Turner, et al., *J Neurosurg* 118(5):1072-1085, 2013, incorporated herein by reference in its entirety). Combination therapies that affect several cellular targets are likely needed to prevent neuronal damage.

The cornea serves a protective role as the outermost tissue of the eye, however it is highly vulnerable to severe injury and disease. Its lack of blood vessels enables its transparency but also limits its ability to heal. Corneal injury, due to its potential to cause irreversible blindness, requires prompt intervention and aggressive treatment. The critical need for improved ocular surface healing therapies is particularly apparent for chemical burns and in severe corneal diseases, such as ocular manifestations of acute Chronic Graft v. Host Disease (GvHD), Stevens-Johnson Syndrome, Ocular Mucous Membrane Pemphigoid and other conditions giving rise to persistent corneal epithelial defect, which collectively comprise an incidence of over 100,000 cases per year. (See, Dietrich-Ntoukas et al. Cornea. 2012, 31(3):299-310; Stevenson W, et al., *Clin Ophthalmol.* 2013, 7:2153-2158.

White K D, et al., *J Allergy Clin Immunol Pract.* 2018; 6(1):38-69; Tauber J. (2002) Autoimmune Diseases Affecting the Ocular Surface. In: Ocular Surface Disease Medical and Surgical Management. Springer, New York, N.Y.; and Wirostko B, et al., Ocul Surf 2015 July; 13(3): 204-21; and Haring, R S., et al., *JAMA Ophthalmol.* 2016 Oct. 1; 134(10):1119-1124.)

Moreover, topical ophthalmic drug development is impeded by many anatomical constraints including tear turnover and dilution, nasolacrimal drainage, and reflex blinking with often less than 5% of the topically administered dose reaching deeper ocular tissues (Gaudana et al., 2009). In the case of corneal wounds, the initial insult causes rifts in the corneal epithelium thereby enabling the passage of topically applied MSC-S to penetrate the epithelial layers.

Accordingly, there is a large unmet need in the art for ocular therapies that can target the eye and deliver a therapeutic payload to difficult-to-reach sensory tissue which may have degenerated due to inflammation secondary to trauma (such as for example, burns, acute inflammation, age, and/or oxidative stress). The present invention meets this need by providing mesenchymal stem cell secretome compositions for use in such treatments, as well as methods for making such compositions.

BRIEF SUMMARY OF THE INVENTION

The present invention provides a mesenchymal stem cell (MSC) secretome composition comprising:
  i. less than about 250 µM IDO (Indoleamine-2,3-dioxygenase) enzyme activity;
  ii. at least one trophic factors/cytokines selected from the group consisting of HGF, FGF-7, TIMP-1, TIMP-2, PAI-1 (Serpin E1), VEGF-A, and/or b-NGF;
  iii. at least one additional factor selected from the group consisting of sFLT-1, PEDF (Serpin F1), IGFBP-2, IGFBP-3, SDF-1, TSG-14, Kallikrein 3, MCP-1, bFGF, Angiogenin, MCP-2, Angio-2, IL-6, IL-17, G-CSF, M-CSF, GM-CSF, IL-8, TNF-beta, PDGF, SOD1, SOD2, SOD3, and/or HO-1; and iv. at least one additional factor selected from the group consisting of DPPIV (dipeptidyl peptidase-4), uPA, Angiopoietin-1, Angiopoietin-2, Amphiregulin, Endostatin, Endothelial-1, Thrombospondin-2, and/or Thrombospondin-1.

In some embodiments, the MSC secretome further comprises "higher levels" of at least one factor selected from the group consisting of Serpin E1, TIMP-1, Thrombospondin-1, Pentraxin-3 (TSG-14), Platelet Factor 4, and/or Serpin F1, optionally 1 ng/mL-8 ng/mL.

In some embodiments, the MSC secretome further comprises "mid-range" levels of at least one factor selected from the group consisting of Angiopoietin-1, Angiopoietin-2, Amphiregulin, Endostatin, Endothelial-1, Thrombospondin-2, Thrombospondin-1, Angiogenin, DPPIV, IGFBP-3, and/or uPA, optionally 400 pg/mL-3000 pg/mL.

In some embodiments, the MSC secretome further comprises at least one factor selected from the group consisting of Apolipoprotein A1, Complement Factor D, C-reactive protein, Cystatin C, DKK-1, Emmprin, Osteopontin, vitamin D BP, MIF, RANTES, uPAR, IL-17a, GDF-15, and/or IFNγ.

In some embodiments, the MSC secretome comprises ratios of anti-angiogenic to pro-angiogenic wherein the ratio is >2, >3, >4, or >5.

In some embodiments, the MSC secretome further comprises "low" levels for VEGF, optionally 0 pg/mL-200 pg/mL.

In some embodiments, the level of VEGF is 5-10 fold lower than the level of Serpin E1.

In some embodiments, the composition comprises one or more anti-angiogenic factor, and wherein the sum of the concentration of the one or more anti-angiogenic factors relative to the concentration of VEGF is >2, >3, >4, or >5.

In some embodiments, the MSC secretome does not comprise and/or comprises very low levels of bFGF, PLGF, and PDGF, optionally less than 1000 pg/mL.

In some embodiments, the MSC secretome composition has a pH of about 4.7 to about 7.5.

In some embodiments, the MSC secretome is formulated in a buffer system selected from the group consisting of di/mono sodium phosphate, sodium citrate/citric acid, boric acid/sodium citrate, boric acid/sodium tetraborate, and citric acid/disodium phosphate.

In some embodiments, the MSC secretome composition further comprises a tonicity modifying agent.

In some embodiments, the tonicity modifying agent is selected from the group consisting of NaCl, KCl, mannitol, dextrose, sucrose, sorbitol, and glycerin.

In some embodiments, the MSC secretome further comprises mono/di-sodium phosphate, mannitol, and trehalose, wherein the composition has a pH of about pH 7.4.

In some embodiments, the MSC secretome further comprises divalent cations.

In some embodiments, the divalent cations are selected from the group consisting of Mg2+, Ca2+, and Zn2+.

In some embodiments, the MSC secretome further comprises di-sodium phosphate/citric acid, mannitol, and trehalose, wherein the composition has a pH of about pH 6.4.

In some embodiments, the composition further comprises an adhesive agent.

In some embodiments, the adhesive agent is selected from the group consisting of hypromellose, Poloxamer 407, Poloxamer 188, Poloxomer 237, Poloxomer 338, Hypromellose, (HPMC), polycarbophil, polyvinylpyrrolidone (PVP), PVA (polyvinyl alcohol), polyimide, sodium hyaluronate, gellan gum, poly(lactic acid-co-glycolic acid) (PLGA), polysiloxane, polyimide, carboxymethylcellulose (CMC), or hydroxypropyl methylcellulose (HPMC), hydroxy methyl cellulose, hydroxy ethyl cellulose, sodium carboxy methyl cellulose, fibrin glue, polyethyelene glycol, and GelCORE.

The present invention also provides a method of making a mesenchymal stem cell (MSC) secretome composition comprising:
v. culturing mesenchymal stem cells (MSCs) in a first culture media;
vi. removing the first culture media from step (i) from the MSCs;
vii. washing the MSCs in step (ii);
viii. adding a second culture media and culturing for about 1-5 days;
ix. harvesting the second culture media from step (iv) as conditioned media; and
x. processing the conditioned media in step (v) into the MSC secretome composition as described herein.

In some embodiments, the MSC secretome composition is a secretome composition as described herein.

In some embodiments, step (vi) processing the conditioned media in step (v) into the secretome composition comprises:
a) filtering the harvested conditioned media from step (v) to remove cell particulate;
b) concentrating the filtered conditioned media from step (a);
c) buffer exchanging with the formulation buffer.

In some embodiments, step c) comprises buffer exchanging with a buffer system selected from the group consisting of di/mono sodium phosphate, sodium citrate/citric acid, boric acid/sodium citrate, boric acid/sodium tetraborate, and citric acid/disodium phosphate.

In some embodiments, the filtering step (a) comprises the use of a 0.45 μm filter, a 0.22 μm filter, 0.8 μm filter, and 0.65 μm filter, a low protein binding PVDF membranes, and/or PES (polyethersulfone).

In some embodiments, the concentration step (b) comprises using a hollow fiber filters, tangential flow filtration systems, or centrifugation based size exclusion techniques.

In some embodiments, centrifugation based size exclusion techniques employs a 3-10 kDa MW cutoff.

In some embodiments, the present invention provides a method of treatment of an ocular disease comprising administering to a patient in need thereof therapeutically effective amount of a mesenchymal stem cell secretome composition as described herein or a composition made according to the methods described herein to a patient in need thereof.

In some embodiments, the composition is administered to a target area.

The present invention also provides a method for treating visual dysfunction following traumatic injury to ocular structures in a patient in need thereof comprising administering to the patient a therapeutically effective amount of a mesenchymal stem cell secretome composition as described herein or a composition made according to the methods described herein.

The present invention also provides a method for inducing and/or promoting ocular wound healing. in a patient in need thereof comprising administering to the patient a therapeutically effective amount of a mesenchymal stem cell secretome composition as described herein or a composition made according to the methods described herein.

The present invention also provides a method for reducing and/or inhibiting neovascularization, reducing and/or inhibiting scarring, promoting and/or preserving vision, and/or increasing wound closure rate (e.g., decreasing would closure time) in a patient in need thereof comprising administering to the patient a therapeutically effective amount of a mesenchymal stem cell secretome composition as described herein or a composition made according to the methods described herein.

The present invention also provides a method for reducing and/or inhibiting neovascularization and reducing scarring in order to promote vision preservation in a patient in need thereof comprising administering to the patient a therapeutically effective amount of a mesenchymal stem cell secretome composition as described herein or a composition made according to the methods described herein.

In some embodiments, the mesenchymal stem cell secretome composition is formulated for topical administration.

In some embodiments, the mesenchymal stem cell secretome composition is formulated for subconjunctival injection.

The present invention also provides a method for characterizing a MSC secretome, wherein the method comprises:
(i) subjecting an MSC secretome to one or more characterization assays, wherein characterization assays are selected from the group consisting of physical component characterizations, oxidative stress assays, safety analyses, stability assays, proliferation assays, migration assays, neovascularization assays, differentiation/scarring assays, and/or inflammation assays; and
(ii) determining the results from the one or more assays in (i).

The present invention also provides a method determining biopotency and stability of a MSC secretome comprising, wherein the method comprises:
(i) subjecting an MSC secretome to one or more characterization assays, wherein characterization assays are selected from the group consisting of physical component characterizations, oxidative stress assays, safety analyses, stability assays, proliferation assays, migration assays, neovascularization assays, differentiation/scarring assays, and/or inflammation assays; and
(ii) determining the results from the one or more assays in (i).

The present invention also provides a method for determining MSC secretome lot consistency between a plurality of MSC secretome lots, wherein the method comprises:
(i) subjecting an MSC secretome to one or more characterization assays, wherein characterization assays are selected from the group consisting of physical component characterizations, oxidative stress assays, safety analyses, stability assays, proliferation assays, migration assays, neovascularization assays, differentiation/scarring assays, and/or inflammation assays; and
(ii) determining the results from the one or more assays in (i).

In some embodiments, the results in (ii) from a physical component characterization identify an anti-angiogenic MSC secretome as described herein.

In some embodiments, the results in (ii) from a safety analyses provides for a MSC secretome that exhibits blood compatibility, and low and/or no pyrogens and/or endotoxins.

In some embodiments, the results in (ii) from a stability assay provides for a MSC secretome that exhibits stability at 4° C., 20° C., and/or 37° C. for at least 7 days.

In some embodiments, the results in (ii) from a proliferation assay provides for a MSC secretome that induces proliferation.

In some embodiments, the results in (ii) from a migration assay provides for a MSC secretome that induces migration.

In some embodiments, the results in (ii) from a neovascularization assay provides for a MSC secretome that inhibits neovascularization.

In some embodiments, the results in (ii) from a differentiation/scarring assay provides for a MSC secretome that inhibits differentiation and/or scarring.

In some embodiments, the results in (ii) from an inflammation assay provides for a MSC secretome that inhibits inflammation.

In some embodiments, the method further comprises:
(iii) identifying a MSC secretome lot based on the results in (ii).

The present invention also provides a panel of tests and/or assays for characterizing a MSC secretome, wherein the panel comprises at least two characterization assays, wherein characterization assays are selected from the group consisting of physical component characterizations, oxidative stress assays, safety analyses, stability assays, proliferation assays, migration assays, neovascularization assays, differentiation/scarring assays, and/or inflammation assays.

The present invention also provides a panel of tests and/or assays for determining consistency between MSC secretome lots, wherein the panel comprises one or more characterization assays, wherein characterization assays are selected from the group consisting of physical component characterizations, oxidative stress assays, safety analyses, stability assays, proliferation assays, migration assays, neovascularization assays, differentiation/scarring assays, and/or inflammation assays.

In some embodiments, the physical component characterization identifies a MSC secretome as described herein.

In some embodiments, the results in (ii) from a safety analyses provides for a MSC secretome that exhibits blood compatibility, and low and/or no pyrogens and/or endotoxins.

In some embodiments, the stability assay identifies for a MSC secretome that exhibits stability at 4° C., 20° C., and/or 37° C. for at least 7 days.

In some embodiments, the proliferation assay identifies for a MSC secretome that induces proliferation.

In some embodiments, the migration assay identifies a MSC secretome that induces migration.

In some embodiments, the neovascularization assay identifies for a MSC secretome that inhibits neovascularization.

In some embodiments, the differentiation/scarring assay identifies a MSC secretome that inhibits differentiation and/or scarring.

In some embodiments, the inflammation assay identifies a MSC secretome that inhibits inflammation.

In some embodiments, the physical component characterizations, oxidative stress assays, safety analyses, stability assays, proliferation assays, migration assays, neovascularization assays, differentiation/scarring assays, and/or inflammation assays are all performed.

In some embodiments, the panel of tests and/or assays as described herein identify a MSC secretome as described herein.

In some embodiments, the MSC secretome is an anti-angiogenic MSC secretome and/or an anti-scarring MSC secretome.

In some embodiments, the MSC secretome is an anti-angiogenic MSC secretome and/or or an anti-scarring MSC secretome.

In some embodiments, the MSC secretome is an anti-angiogenic MSC secretome or an anti-scarring MSC secretome.

The present invention also provides a mesenchymal stem cell (MSC) secretome composition comprising:
i. at least one trophic factors/cytokines selected from the group consisting of HGF, TIMP-1, TIMP-2, PAI-1 (Serpin E1), VEGF-A, and b-NGF;
ii. at least one additional factor selected from the group consisting of PEDF (Serpin F1), IGFBP-2, IGFBP-3, SDF-1, TSG-14, Kallikrein 3, MCP-1, Angiogenin, MCP-2, Angio-2, IL-6, IL-17, G-CSF, M-CSF, GM-CSF, IL-8, TNF-beta, and PDGF; and
iii. at least one additional factor selected from the group consisting of DPPIV (dipeptidyl peptidase-4), uPA, Angiopoietin-1, Angiopoietin-2, Amphiregulin, Endostatin, Endothelial-1, Thrombospondin-2, and Thrombospondin-1.

The MSC secretome composition according to claim 1, wherein the MSC secretome composition further comprises high levels of at least one factor selected from the group consisting of Serpin E1, TIMP-1, Thrombospondin-1, Pentraxin-3 (TSG-14), Platelet Factor 4, and Serpin F1.

In some embodiments, the MSC secretome composition according to claim 2, wherein the MSC secretome composition comprises 1 ng/mL-100 ng/mL of at least one factor selected from the group consisting of Serpin E1, TIMP-1, Thrombospondin-1, Pentraxin-3 (TSG-14), Platelet Factor 4, and Serpin F1.

In some embodiments, the MSC secretome composition according to claim 1, wherein the MSC secretome composition further comprises mid-range levels of at least one factor selected from the group consisting of Angiopoietin-1, Angiopoietin-2, Amphiregulin, Endostatin, Endothelial-1, Thrombospondin-2, Thrombospondin-1, Angiogenin, DPPIV, IGFBP-3, and uPA.

In some embodiments, the MSC secretome composition according to claim 4, wherein the MSC secretome comprises 400 pg/mL-3000 pg/mL of at least one factor selected from the group consisting of Angiopoietin-1, Angiopoietin-2, Amphiregulin, Endostatin, Endothelial-1, Thrombospondin-2, Thrombospondin-1, Angiogenin, DPPIV, IGFBP-3, and uPA.

In some embodiments, the MSC secretome composition according to claim 1, wherein the MSC secretome composition further comprises at least one factor selected from the group consisting of Apolipoprotein A1, Complement Factor D, C-reactive protein, Cystatin C, DKK-1, Emmprin, Osteopontin, vitamin D BP, MIF, RANTES, uPAR, IL-17a, GDF-15, and IFNγ.

In some embodiments, the MSC secretome composition according to claim 1, wherein the MSC secretome composition comprises ratios of anti-angiogenic to pro-angiogenic wherein the ratio is >2, >3, >4, or >5.

In some embodiments, the MSC secretome composition according to claim 7, wherein the anti-angiogenic factors includes one or more factors selected from the group consisting of PEDF, lower levels of VEGF, and Serpin E1 and the pro-angiogenic factors includes one or more factors selected from the group consisting of VEGF, Angiogenin, IGFBP-3, uPA, Angio-1, Angio-2, Endothelial-1.

In some embodiments, the MSC secretome composition according to claim 1, wherein the MSC secretome composition further comprises low levels for VEGF.

In some embodiments, the MSC secretome composition according to claim 9, wherein the MSC secretome composition comprises 1 pg/mL-400 pg/mL of VEGF.

In some embodiments, the MSC secretome composition according to any one of claim 1, wherein the level of VEGF is 5-10 fold lower than the level of Serpin E1.

In some embodiments, the MSC secretome composition according to claim 1, wherein the composition comprises one or more anti-angiogenic factor, and wherein the sum of the concentration of the one or more anti-angiogenic factors relative to the concentration of VEGF is >2, >3, >4, or >5.

In some embodiments, the MSC secretome composition according to claim 1, wherein the MSC secretome composition does not comprise and/or comprises very low levels of bFGF, PLGF, and PDGF.

In some embodiments, the MSC secretome composition according to claim 13, wherein the MSC secretome comprises less than 1000 pg/mL of bFGF, PLGF, and PDGF.

In some embodiments, the MSC secretome composition according to claim 1, wherein the MSC secretome composition has a pH of about 4.7 to about 7.5.

In some embodiments, the MSC secretome composition according to claim 1, wherein the MSC secretome composition is formulated in a buffer system selected from the group consisting of di/mono sodium phosphate, sodium citrate/citric acid, boric acid/sodium citrate, boric acid/sodium tetraborate, and citric acid/disodium phosphate.

In some embodiments, the MSC secretome composition according to claim 1, wherein the MSC secretome composition further comprises a tonicity modifying agent.

In some embodiments, the MSC secretome composition according to claim 17, wherein the tonicity modifying agent is selected from the group consisting of NaCl, KCl, mannitol, dextrose, sucrose, sorbitol, and glycerin.

In some embodiments, the MSC secretome composition according to claim 1, wherein the MSC secretome composition further comprises mono/di-sodium phosphate, mannitol, and trehalose, and wherein the composition has a pH of about pH 7.4.

In some embodiments, the MSC secretome composition according to claim 1, wherein the MSC secretome composition further comprises divalent cations.

In some embodiments, the MSC secretome composition of claim 19, wherein the divalent cations are selected from the group consisting of $Mg^{2+}$, $Ca^{2+}$, and $Zn^{2+}$.

In some embodiments, the MSC secretome composition according to claim 1, wherein the MSC secretome composition further comprises di-sodium phosphate/citric acid, mannitol, and trehalose, wherein the composition has a pH of about pH 6.4.

In some embodiments, the MSC secretome composition according to claim 1, wherein the MSC secretome composition further comprises an adhesive agent.

In some embodiments, the MSC secretome composition according to claim 23, wherein the adhesive agent is selected from the group consisting of hypromellose, Poloxamer 407, Poloxamer 188, Poloxomer 237, Poloxomer 338, Hypromellose, (HPMC), polycarbophil, polyvinylpyrrolidone (PVP), PVA (polyvinyl alcohol), polyimide, sodium hyaluronate, gellan gum, poly(lactic acid-co-glycolic acid) (PLGA), polysiloxane, polyimide, carboxymethylcellulose (CMC), or hydroxypropyl methylcellulose (HPMC), hydroxy methyl cellulose, hydroxy ethyl cellulose, sodium carboxy methyl cellulose, fibrin glue, polyethyelene glycol, and GelCORE.

In some embodiments, the MSC secretome composition according to claim 1, wherein the MSC secretome composition does not comprise one or more components selected from the group consisting of: xenobiotic components; Phenol red; peptides and biomolecules <3 kDa; antibiotics; protein aggregates >200 nm; cells; non-exosome/non-Extracellular Vesicles cell debris; hormones; and L-glutamine.

In some embodiments, the MSC secretome composition according to claim 2, wherein the MSC secretome composition comprises: HGF; Pentraxin-3 (TSG-14); VEGF; TIMP-1; Serpin E1; and <5 ng/mL IL-8.

In some embodiments, the MSC secretome composition according to claim 2, wherein the MSC secretome composition comprises:
  i. 0.3-4.5 ng/mL HGF;
  ii. 0.5-20 ng/mL Pentraxin-3 (TSG-14);
  iii. 100-600 pg/mL VEGF;
  iv. 10-200 ng/mL TIMP-1;
  v. 20-80 ng/mL Serpin E1; and
  vi. <5 ng/mL IL-8.

In some embodiments, the MSC secretome composition according to claim 1, wherein the MSC secretome composition comprises an anti-angiogenic MSC secretome or an anti-scarring MSC secretome.

The present invention also provides a stable mesenchymal stem cell (MSC) secretome formulation comprising:
  i. 2 µg-20 µg of MSC secretome per mL;
  ii. 2 mg-3 mg monobasic sodium phosphate per mL;
  iii. 11 mg-12 mg dibasic sodium phosphate per mL;
  iv. 11.5 mg-13 mg mannitol per mL;
  v. 23 mg-24 mg trehalose dihydrate;
  vi. 0.5 mg-2 mg hypromellose per mL; and
  wherein the pH is about 4.7 to about 7.5.

The present invention also provides a stable mesenchymal stem cell (MSC) secretome formulation comprising:
  i. 0.004%-0.08% w/w of MSC secretome;
  ii. 4%-5% w/w monobasic sodium phosphate;
  iii. 21.5%-23% w/w dibasic sodium phosphate;
  iv. 23%-25% w/w mannitol;
  v. 46%-48% w/w trehalose dehydrate;
  vi. 1%-3% w/w hypromellose; and
  wherein the pH is about 4.7 to about 7.5.

The present invention further provides a method of treatment for an ocular condition in a subject in need thereof comprising administering to the subject a mesenchymal stem cell (MSC) secretome composition, wherein the MSC secretome composition comprises:
  i. at least one trophic factors/cytokines selected from the group consisting of HGF, TIMP-1, TIMP-2, PAI-1 (Serpin E1), VEGF-A, and b-NGF;
  ii. at least one additional factor selected from the group consisting of PEDF (Serpin F1), IGFBP-2, IGFBP-3, SDF-1, TSG-14, Kallikrein 3, MCP-1, Angiogenin, MCP-2, Angio-2, IL-6, IL-17, G-CSF, M-CSF, GM-CSF, IL-8, TNF-beta, and PDGF; and
  iii. at least one additional factor selected from the group consisting of DPPIV (dipeptidyl peptidase-4), uPA, Angiopoietin-1, Angiopoietin-2, Amphiregulin, Endothelial-1, Thrombospondin-2, and Thrombospondin-1.

In some embodiments, the MSC secretome composition further comprises high levels of at least one factor selected from the group consisting of Serpin E1, TIMP-1, Thrombospondin-1, Pentraxin-3 (TSG-14), Platelet Factor 4, and Serpin F1.

In some embodiments, the MSC secretome composition comprises 1 ng/mL-100 ng/mL of at least one factor selected from the group consisting of Serpin E1, TIMP-1, Thrombospondin-1, Pentraxin-3 (TSG-14), Platelet Factor 4, and Serpin F1.

In some embodiments, the MSC secretome composition further comprises mid-range levels of at least one factor selected from the group consisting of Angiopoietin-1, Angiopoietin-2, Amphiregulin, Endostatin, Endothelial-1, Thrombospondin-2, Thrombospondin-1, Angiogenin, DPPIV, IGFBP-3, and uPA.

In some embodiments, the MSC secretome composition comprises 400 pg/mL-3000 pg/mL of at least one factor selected from the group consisting of Angiopoietin-1, Angiopoietin-2, Amphiregulin, Endostatin, Endothelial-1, Thrombospondin-2, Thrombospondin-1, Angiogenin, DPPIV, IGFBP-3, and uPA.

In some embodiments, the MSC secretome composition further comprises at least one factor selected from the group consisting of Apolipoprotein A1, Complement Factor D, C-reactive protein, Cystatin C, DKK-1, Emmprin, Osteopontin, vitamin D BP, MIF, RANTES, uPAR, IL-17a, GDF-15, and IFNγ.

In some embodiments, the MSC secretome composition comprises ratios of anti-angiogenic to pro-angiogenic wherein the ratio is >2, >3, >4, or >5.

In some embodiments, the anti-angiogenic factors includes one or more factors selected from the group consisting of PEDF, lower levels of VEGF, and Serpin E1 and pro-angiogenic: VEGF, Angiogenin, IGFBP-3, uPA, Angio-1, Angio-2, Endothelial-1.

In some embodiments, the MSC secretome composition further comprises low levels for VEGF.

In some embodiments, the MSC secretome comprises 1 pg/mL-400 pg/mL of VEGF.

In some embodiments, the level of VEGF is 5-10 fold lower than the level of Serpin E1.

In some embodiments, the MSC secretome composition comprises one or more anti-angiogenic factor, and wherein the sum of the concentration of the one or more anti-angiogenic factors relative to the concentration of VEGF is >2, >3, >4, or >5.

In some embodiments, the MSC secretome composition does not comprise or comprises very low levels of bFGF, PLGF, and PDGF.

In some embodiments, the MSC secretome composition comprises less than 1000 pg/mL of bFGF, PLGF, and PDGF.

In some embodiments, the MSC secretome composition has a pH of about 4.7 to about 7.5.

In some embodiments, the MSC secretome composition is formulated in a buffer system selected from the group consisting of di/mono sodium phosphate, sodium citrate/citric acid, boric acid/sodium citrate, boric acid/sodium tetraborate, and citric acid/disodium phosphate.

In some embodiments, the MSC secretome composition further comprises a tonicity modifying agent.

In some embodiments, the tonicity modifying agent is selected from the group consisting of NaCl, KCl, mannitol, dextrose, sucrose, sorbitol, and glycerin.

In some embodiments, the MSC secretome composition further comprises mono/di-sodium phosphate, mannitol, and trehalose, and wherein the composition has a pH of about pH 7.4.

In some embodiments, the MSC secretome composition further comprises divalent cations.

In some embodiments, the divalent cations are selected from the group consisting of $Mg^{2+}$, $Ca^{2+}$, and $Zn^{2+}$.

In some embodiments, the MSC secretome composition further comprises di-sodium phosphate/citric acid, mannitol, and trehalose, and wherein the composition has a pH of about pH 6.4.

In some embodiments, the MSC secretome composition further comprises an adhesive agent.

In some embodiments, the adhesive agent is selected from the group consisting of hypromellose, Poloxamer 407, Poloxamer 188, Poloxomer 237, Poloxomer 338, Hypromellose, (HPMC), polycarbophil, polyvinylpyrrolidone (PVP), PVA (polyvinyl alcohol), polyimide, sodium hyaluronate, gellan gum, poly(lactic acid-co-glycolic acid) (PLGA), polysiloxane, polyimide, carboxymethylcellulose (CMC), or hydroxypropyl methylcellulose (HPMC), hydroxy methyl cellulose, hydroxy ethyl cellulose, sodium carboxy methyl cellulose, fibrin glue, polyethyelene glycol, and GelCORE.

In some embodiments, the MSC secretome composition does not comprise one or more components selected from the group consisting of: xenobiotic components; Phenol red; peptides and biomolecules <3 kDa; antibiotics; protein aggregates >200 nm; cells; non-exosome/non-Extracellular Vesicles cell debris; hormones; and L-glutamine.

In some embodiments, the MSC secretome composition comprises: HGF; Pentraxin-3 (TSG-14); VEGF; TIMP-1; Serpin E1; and <5 ng/mL IL-8.

In some embodiments, the MSC secretome composition comprises:
 i. 0.3-4.5 ng/mL HGF;
 ii. 0.5-20 ng/mL Pentraxin-3 (TSG-14);
 iii. 100-600 pg/mL VEGF;
 iv. 10-200 ng/mL TIMP-1;
 v. 20-80 ng/mL Serpin E1; and
 vi. <5 ng/mL IL-8.

In some embodiments, the MSC secretome composition comprise an anti-angiogenic MSC secretome or an anti-scarring MSC secretome.

The present invention also provides a method of treatment for an ocular condition in a subject in need thereof comprising administering to the subject a mesenchymal stem cell (MSC) secretome composition, wherein the MSC secretome composition is a stable mesenchymal stem cell (MSC) secretome formulation comprising:
 i. 2 µg-20 µg of MSC secretome per mL;
 ii. 2 mg-3 mg monobasic sodium phosphate per mL;
 iii. 11 mg-12 mg dibasic sodium phosphate per mL;
 iv. 11.5 mg-13 mg mannitol per mL;
 v. 23 mg-24 mg trehalose dihydrate;
 vi. 0.5 mg-2 mg hypromellose per mL; and
 wherein the pH is about 4.7 to about 7.5.

The present invention also provides a method of treatment for an ocular condition in a subject in need thereof comprising administering to the subject a mesenchymal stem cell (MSC) secretome composition, wherein the MSC secretome composition is a stable mesenchymal stem cell (MSC) secretome formulation comprising:
 i. 0.004%-0.08% w/w of MSC secretome
 ii. 4%-5% w/w monobasic sodium phosphate;
 iii. 21.5%-23% w/w dibasic sodium phosphate;
 iv. 23%-25% w/w mannitol;
 v. 46%-48% w/w trehalose dehydrate;
 vi. 1%-3% w/w hypromellose; and
 wherein the pH is about 4.7 to about 7.5.

BRIEF DESCRIPTION OF THE DRAWINGS

FIG. 5A-FIG. 5B. MSC-S has an anti-angiogenic profile by protein expression. A) A human angiogenesis array was used to evaluate pro-angiogenic and anti-angiogenic factors in MSC-S. B) Anti-angiogenic factors (black) are present at high levels, and pro-angiogenic factors (white) are present in low levels. Mean pixel intensities were determined using Image J (NIH, Bethesda, Md.)

DETAILED DESCRIPTION OF THE INVENTION

I. Introduction

Figure 1:
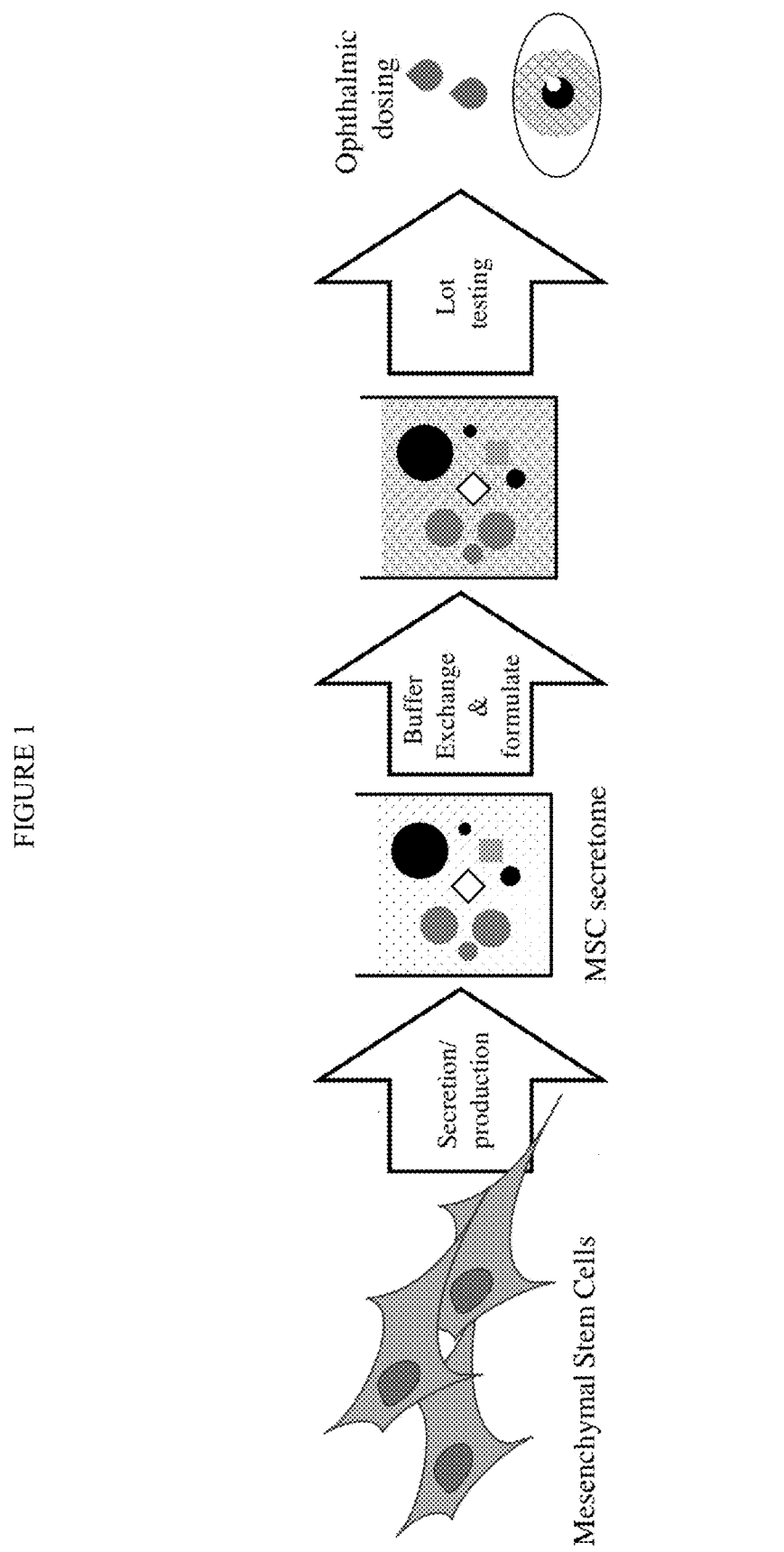
FIG. 1. Schematic diagram of an embodiment of MSC secretome preparation, processing, and use.

The present invention provides mesenchymal stem cell secretome compositions for use in such treatments, as well as methods for making such compositions. Such compositions, uses, and associated methods are described in further detail below.

A. Definitions

Terms used in the claims and specification are defined as set forth below unless otherwise specified. In the case of direct conflict with a term used in a parent provisional patent application, the term used in the instant specification shall control.

As used herein "isolated" refers to material removed from its original environment and is thus altered "by the hand of man" from its natural state.

As used herein, "enriched" means to selectively concentrate or to increase the amount of one or more materials by elimination of the unwanted materials or selection and separation of desirable materials from a mixture (e.g., separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers. As used herein, the term "multipotent stem cells" are true stem cells but can only differentiate into a limited number of types. For example, the bone marrow contains multipotent stem cells that give rise to all the cells of the blood but may not be able to differentiate into other cells types.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Generally, clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50-fold and up to 150-fold higher than the number of cells in the primary culture after 5 passages, as compared to about a 20-fold increase in such cells using previous methods. In another example, the level of cells per gram of amniotic tissue in expanded compositions of AMP cells is at least 30-fold and up to 100-fold higher than the number of cells in the primary culture after 3 passages. Accordingly, an "expanded" population has at least a 2-fold, and up to a 10-fold, improvement in cell numbers per gram of amniotic tissue over previous methods. The term "expanded" is meant to cover only those situations in which a person has intervened to elevate the number of the cells.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to, hormones, cytokines, extracellular matrix (ECM), proteins, vesicles, antibodies, chemokines, receptors, inhibitors and granules. The medium containing the cellular factors is the conditioned medium. Examples of methods of preparing conditioned media have been described in U.S. Pat. No. 6,372,494 which is incorporated by reference in its entirety herein. As used herein, conditioned medium also refers to components, such as proteins, that are recovered and/or purified from conditioned medium or from for example, MSC cells.

As used herein, the term "mesenchymal stem cell composition" or "MSC composition" means conditioned medium that has been derived from MSCs and in some instances has undergone further processing. In some embodiments, "MSC secretome" can refer to the crude conditioned media derived from the MSC. In some embodiments, "MSC secretome" can refer to the composition obtained from the crude conditioned media after it has been subjected to further processing as described herein.

As used herein, the term "suspension" means a liquid containing dispersed components, e.g., cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene. Polynucleotides used herein can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "secretome composition" refers to a composition comprising one or more substances which are secreted from a cell. In certain embodiments, a secretome composition may include one or more cytokines, one or more exosomes, and/or one or more microvesicles. A secretome composition may be purified or unpurified. In some embodiments, a secretome composition may further comprise one or more substances that are not secreted from a cell (e.g., culture media, additives, nutrients, etc.). In some a secretome composition does not comprise and or comprises only trace amounts of one or more substances that are not secreted from a cell (e.g., culture media, additives, nutrients, etc.).

The terms "treatment," "treat," or "treating," and the like, as used herein covers any treatment of a human or nonhuman mammal (e.g., rodent, cat, dog, horse, cattle, sheep, and primates etc.), and includes preventing the disease or condition from occurring in a subject who may be predisposed to the disease or condition but has not yet been diagnosed as having it. It also includes inhibiting (arresting development of), relieving or ameliorating (causing regression of), or curing (permanently stopping development or progression) the disease, condition and/or any related symptoms. The terms "treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, e.g., arresting its development; (c) relieving and or ameliorating the disease or condition, e.g., causing regression of the disease or condition; or (d) curing the disease or condition, e.g., stopping its development or progression. The population of subjects treated by the methods of the invention includes subjects suffering from the undesirable condition or disease, as well as subjects at risk for development of the condition or disease. In some embodiments, "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder, and/or condition, and/or of a subject who exhibits only early signs of the disease, disorder, and/or condition. Alternatively and/or additionally, such treatment may be of a subject who exhibits one or more established signs of the relevant disease, disorder, and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, a "wound" is any disruption, from whatever cause, of normal anatomy (internal and/or external anatomy) including but not limited to traumatic injuries such as mechanical (e.g. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (e.g. ocular contusion). A wound is dynamic and the process of healing is a continuum requiring a series of integrated and interrelated cellular processes that begin at the time of wounding and proceed beyond initial wound closure through arrival at a stable wound closure. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein, the terms "a" or "an" means one or more or at least one.

As used herein, a "therapeutically effective" or "effective" dosage or amount of a composition is an amount sufficient to have a positive effect on a given medical condition. If not immediate, the therapeutically effective or effective dosage or amount may, over period of time, provide a noticeable or measurable effect on a patient's health and well-being.

As used herein a "pharmaceutical composition" refers to an effective amount of the compositions described herein in combination with a delivery components. The pharmaceutical composition may optionally contain other components such as pharmaceutically suitable carriers and excipients, which may facilitate administration of a composition and/or its individual components to a subject.

The term "pharmaceutically acceptable carrier" refers to a carrier or a diluent that does not cause significant irritation to a subject and does not abrogate the biological activity and properties of the administered compounds.

The term "excipient" refers to an inert substance added to a pharmaceutical composition to further facilitate administration of a compound.

As used herein, the terms "mix", "mixing", and the like describe a mechanical process or a mechanical treatment of the components. For example, mixing can be in the sense of carrying out repeated cycles of pressing and folding or comparable processing steps which lead to an intense compression and mixing of the provided hydrophobic matrices.

Adult stem cells can be harvested from a variety of adult tissues, including bone marrow, fat, and dental pulp tissue. While all adult stem cells are cable of self-renewal and are considered multipotent, their therapeutic functions vary depending on their origin. As a result, each type of adult stem cell has unique characteristics that make them suitable for certain diseases. Mesenchymal stem cells (MSCs) are typically derived from the mesoderm and are multipotent, nonhematopoietic (non-blood) stem cells isolated from (derived from) capable of differentiating into a variety of tissues, including osteoblasts (e.g., bone cells), chondrocytes (e.g., cartilage cells), myocytes (e.g., muscle cells) and adipocytes (e.g., fat cells which give rise to marrow adipose tissue). As used herein, "isolated" refers to cells removed from their original environment. Stem cells produce factors, such as growth factors, that regulate or are important for regulating multiple biological processes. A growth factor is an agent, such as a naturally occurring substance capable of stimulating cellular growth and/or proliferation and/or cellular differentiation. Typically, growth factors are proteins or steroid hormones. While the terms "growth factor" and "factor" and the like are used interchangeably herein, the term "biological factor" is not limited to growth factors.

Human mesenchymal stem cells (MSCs), can be characterized by the surface marker profile of CD45−/CD31−/CD73+/CD90+/CD105+/CD44+ (or any suitable subset thereof). (See Bourin et al., Cytotherapy 15(6):641-648 (2013)). Further, appropriate stem cells display the CD34+ positive at the time of isolation, but lose this marker during culturing. Therefore, the full marker profile for one stem cell type that may be used according to the present application includes CD45−/CD31−/CD73+/CD90+/CD105+. In another embodiment utilizing mouse stem cells, the stem cells are characterized by the Sca-1 marker, instead of CD34, to define what appears to be a homologue to the human cells described above, with the remaining markers remaining the same.

The phrase "conditioned medium" or "CM" refers to media which includes biological factors secreted by MSCs. This can also be referred to herein as the "secretome", "MSC-CM", "MSC secretome" and/or "MSC derived secretome". Also provided are processed "conditioned medium" which included biological factors secreted by MSCs and which has been further processed by, for example, filtration, purification, and/or concentration procedures. The "conditioned medium" is obtained by culturing stem cells in media, as described herein in detail, and separating the resulting media, which contains stem cells and their secreted stem cell products (secretome) into conditioned medium that contains biological factors and fewer stem cells than were present prior to separation. The conditioned medium may be used in the methods described herein and is substantially free of stem cells (may contain a small percentage of stem cells) or free of stem cells. Biological factors that may be in the conditioned medium include, but are not limited to, proteins (e.g., cytokines, chemokines, growth factors, enzymes), nucleic acids (e.g., miRNA), lipids (e.g., phospholipids), polysaccharides, and/or combinations thereof. Any combination(s) of these biological factors may be either bound within or on the surface of extracellular vesicles (e.g., exosomes) or separate from extracellular vesicles.

B. Compositions and Formulations

According to the present description, compositions comprising conditioned medium comprising mesenchymal stem cell (MSC) secretome and/or mesenchymal stem cell (MSC) secretome (including processed MSC secretome) are provided herein.

In some embodiments, the MSC secretome is generally low for angiogenic factors. In some embodiments, the MSC secretome does not promote angiogenesis. In some embodiments, the MSC secretome exhibits anti-angiogenic properties. In some embodiments, the MSC secretome provides for reduced angiogenesis as compared to other secretome. In some embodiments, the MSC secretome provides for a 10%, 20%, 30%, 40%, 50%, 60%, 70%, 80%, 90%, 95%, or 99% reduction in angiogenesis. In some embodiments, the MSC secretome provides for a 10%, 20%, 30%, 40%, 50%, 60%, 70%, 80%, 90%, 95%, or 99% reduction in angiogenesis as compared to another secretome. In some embodiments, the MSC secretome provides for a 10%, 20%, 30%, 40%, 50%, 60%, 70%, 80%, 90%, 95%, or 99% reduction in angiogenesis as compared to the conditioned media prior to processing into the MSC secretome. In some embodiments, the MSC secretome has low angiogenesis induction. In some embodiments, the MSC secretome has reduced angiogenic response. In some embodiments, the MSC secretome has reduced angiogenic capacity. In some embodiments, the MSC secretome impairs and/or reduces the normal formation of blood vessels in presence of media supportive of angiogenesis. In some embodiments, the MSC secretome has reduced angiogenic capacity when the MSC secretome is compared to untreated control. In some embodiments, the MSC secretome has reduced angiogenic capacity as compared to a sample treated with serum containing media. In some embodiments, the MSC secretome attenuates an angiogenic response. In some embodiments, the MSC secretome reduces the angiogenic response induce by serum containing media. In some embodiments, a reduction in angiogenic response is induced by the MSC secretome when secretome plus serum containing media (reduced or no angiogenic response) is compared to serum containing media (angiogenic response). In some embodiments, an angiogenic response is indicated by tube formation in a cell based assay. In some embodiments, an angiogenic response is indicated by tube formation in an endothelial cell tube formation assay. In some embodiments, an angiogenic response is indicated by blood vessel formation in a CAM assay. In some embodiments, an angiogenic response is indicated by blood vessel formation in any blood vessel formation assay known in the art.

In some embodiments, the mesenchymal stem cell (MSC) secretome composition comprises
  i. IDO (Indoleamine-2,3-dioxygenase) enzyme activity;
  ii. "threshold" ppm levels for at least one trophic factors/cytokines selected from the group consisting of HGF, FGF-7, TIMP-1, TIMP-2, PAI-1 (Serpin E1), VEGF-A, and b-NGF;
  iii. "threshold" ppm levels for at least one additional factor selected from the group consisting of sFLT-1, PEDF (Serpin F1), IGFBP-2, IGFBP-3, SDF-1, TSG-14, Kallikrein 3, MCP-1, bFGF, Angiogenin, MCP-2, Angio-2, IL-6, IL-17, G-CSF, M-CSF, GM-CSF, IL-8, TNF-beta, PDGF, SOD1, SOD2, SOD3, and HO-1; and
  iv. "threshold" ppm levels for at least one additional factor selected from the group consisting of DPPIV (dipeptidyl peptidase-4), uPA, Angiopoietin-1, Angiopoietin-2, Amphiregulin, Endostatin, Endothelial-1, Thrombospondin-2, and Thrombospondin-1.

In some embodiments, the mesenchymal stem cell (MSC) secretome composition comprises at least one additional factor which includes but is not limited to Apolipoprotein A1, Complement Factor D, C-reactive protein, Cystatin C, DKK-1, Emmprin, Osteopontin, vitamin D BP, MIF, RANTES, uPAR, IL-17a, GDF-15, and/or IFNγ. In some embodiments, the mesenchymal stem cell (MSC) secretome composition comprises at least one additional factor selected from the group consisting of Apolipoprotein A1, Complement Factor D, C-reactive protein, Cystatin C, DKK-1, Emmprin, Osteopontin, vitamin D BP, MIF, RANTES, uPAR, IL-17a, GDF-15, and IFNγ.

In some embodiments, the mesenchymal stem cell (MSC) secretome composition comprises Pentraxin-3, TIMP-1, Serpin E1, TSP-1, and HGF.

In some embodiments, the mesenchymal stem cell (MSC) secretome composition comprises 2-16 ng/mL, or 9.8+/−0.5 ng/ml Pentraxin-3.

In some embodiments, the mesenchymal stem cell (MSC) secretome composition comprises 10-200 ng/mL, or 90+/−21.5 ng/ml TIMP-1.

In some embodiments, the mesenchymal stem cell (MSC) secretome composition comprises 10-100 ng/mL, or 49.2+/−9.8 ng/ml Serpin E1.

In some embodiments, the mesenchymal stem cell (MSC) secretome composition comprises 0.1-10 ng/mL, or 2.0+/−0.3 ng/ml HGF.

In some embodiments, the mesenchymal stem cell (MSC) secretome composition comprises 100-800 pg/mL, or 304+/−44 pg/ml VEGF.

In some embodiments, the mesenchymal stem cell (MSC) secretome composition comprises 0.1-100 pg/mL, or <1 ng/ml IL-8.

In some embodiments, the IDO (Indoleamine-2,3-dioxygenase) enzyme activity less than about 250 µM. In some embodiments, the IDO (Indoleamine-2,3-dioxygenase) enzyme activity is from 0 µM to about 250 µM. In some embodiments, the IDO (Indoleamine-2,3-dioxygenase) enzyme activity is from 50 µM to about 250 µM L-Kynurenine/million MSC. In some embodiments, the IDO (Indoleamine-2,3-dioxygenase) enzyme activity is from 50 µM to about 200 µM L-Kynurenine/million MSC. In some embodiments, the IDO (Indoleamine-2,3-dioxygenase) enzyme activity is from 100 µM to about 250 µM L-Kynurenine/million MSC. In some embodiments, the IDO (Indoleamine-2,3-dioxygenase) enzyme activity is from 100 µM to about 200 µM L-Kynurenine/million MSC. In some embodiments, the IDO (Indoleamine-2,3-dioxygenase) enzyme activity is about 0 µM, about 10 µM, about 20 µM, about 30 µM, about 40 µM, about 50 µM, about 60 µM, about 70 µM, about 80 µM, about 90 µM, about 100 µM, about 110 µM, about 120 µM, about 130 µM, about 140 µM, about 150 µM, about 160 µM, about 170 µM, about 180 µM, about 190 µM, about 200 µM, about 210 µM, about 220 µM, about 230 µM, about 240 µM, or about 250 µM L-Kynurenine/million MSC.

In some embodiments, the MSC secretome further comprises "threshold" ppm levels for at least one additional factor which includes but is not limited to sFLT-1, PEDF (Serpin F1), IGFBP-2, IGFBP-3, SDF-1, TSG-14, Kallikrein 3, MCP-1, bFGF, Angiogenin, MCP-2, Angio-2, IL-6, IL-17, G-CSF, M-CSF, GM-CSF, IL-8, TNF-beta, PDGF, SOD1, SOD2, SOD3, and/or HO-1. In some embodiments, the MSC secretome further comprises "threshold" ppm levels for at least one additional factor selected from the group consisting of sFLT-1, PEDF (Serpin F1), IGFBP-2, IGFBP-3, SDF-1, TSG-14, Kallikrein 3, MCP-1, bFGF, Angiogenin, MCP-2, Angio-2, IL-6, IL-17, G-CSF, M-CSF, GM-CSF, IL-8, TNF-beta, PDGF, SOD1, SOD2, SOD3, and HO-1. In some embodiments, the MSC secretome further comprises one additional factor in a concentration range of 200 pg/mL to 5000 pg/mL, wherein the one additional factor includes but is not limited to sFLT-1, PEDF (Serpin F1), IGFBP-2, IGFBP-3, SDF-1, TSG-14, Kallikrein 3, MCP-1, bFGF, Angiogenin, MCP-2, Angio-2, IL-6, IL-17, G-CSF, M-CSF, GM-CSF, IL-8, TNF-beta, PDGF, SOD1, SOD2, SOD3, and/or HO-1. In some embodiments, the MSC secretome further comprises 1000-3000 pg/mL of sFLT-1. In some embodiments, the MSC secretome further comprises 2000-8000 pg/mL of PEDF. In some embodiments, the MSC secretome further comprises 400-800 pg/mL of TSG-6.

In some embodiments, the MSC secretome further comprises "higher" levels of at least one factor selected from the group consisting of Serpin E1, TIMP-1, Thrombospondin-1, Pentraxin-3 (TSG-14), Platelet Factor 4, and Serpin F1. In some embodiments, the MSC secretome further comprises "higher" levels of Serpin E1. In some embodiments, the MSC secretome further comprises "higher" levels of TIMP-1. In some embodiments, the MSC secretome further comprises "higher" levels of Thrombospondin-1. In some embodiments, the MSC secretome further comprises "higher" levels of Pentraxin-3 (TSG-14). In some embodiments, the MSC secretome further comprises "higher" levels of Platelet Factor 4. In some embodiments, the MSC secretome further comprises "higher" levels of Serpin F1. In some embodiments, the MSC secretome comprises 1 ng/mL to 20 ng/mL at least one factor selected from the group consisting of Serpin E1, TIMP-1, Thrombospondin-1, Pentraxin-3 (TSG-14), Platelet Factor 4, and Serpin F1. In some embodiments, the MSC secretome comprises 1 ng/mL to 8 ng/mL at least one factor selected from the group consisting of Serpin E1, TIMP-1, Thrombospondin-1, Pentraxin-3 (TSG-14), Platelet Factor 4, and Serpin F1. In some embodiments, the MSC secretome comprises 2 ng/mL to 8 ng/mL at least one factor selected from the group consisting of Serpin E1, TIMP-1, Thrombospondin-1, Pentraxin-3 (TSG-14), Platelet Factor 4, and Serpin F1. In some embodiments, the MSC secretome comprises 3 ng/mL to 8 ng/mL at least one factor selected from the group consisting of Serpin E1, TIMP-1, Thrombospondin-1, Pentraxin-3 (TSG-14), Platelet Factor 4, and Serpin F1. In some embodiments, the MSC secretome comprises 4 ng/mL to 8 ng/mL at least one factor selected from the group consisting of Serpin E1, TIMP-1, Thrombospondin-1, Pentraxin-3 (TSG-14), Platelet Factor 4, and Serpin F1. In some embodiments, the MSC secretome comprises 5 ng/mL to 8 ng/mL at least one factor selected from the group consisting of Serpin E1, TIMP-1, Thrombospondin-1, Pentraxin-3 (TSG-14), Platelet Factor 4, and Serpin F1. In some embodiments, the MSC secretome comprises 6 ng/mL to 8 ng/mL at least one factor selected from the group consisting of Serpin E1, TIMP-1, Thrombospondin-1, Pentraxin-3 (TSG-14), Platelet Factor 4, and Serpin F1. In some embodiments, the MSC secretome comprises 2 ng/mL to 7 ng/mL at least one factor selected from the group consisting of Serpin E1, TIMP-1, Thrombospondin-1, Pentraxin-3 (TSG-14), Platelet Factor 4, and Serpin F1.

In some embodiments, the MSC secretome composition further comprises "mid-range" levels of at least one factor including but not limited to Angiopoietin-1, Angiopoietin-2, Amphiregulin, Endostatin, Endothelial-1, Thrombospondin-2, and Thrombospondin-1, Angiogenin, DPPIV, IGFBP-3, and/or uPA. In some embodiments, the MSC secretome composition further comprises "mid-range" levels of at least one factor selected from the group consisting of Angiopoietin-1, Angiopoietin-2, Amphiregulin, Endostatin, Endothelial-1, Thrombospondin-2, and Thrombospondin-1, Angiogenin, DPPIV, IGFBP-3, and uPA. In some embodiments, the MSC secretome composition further comprises "mid-range" levels of at least one factor selected from the group consisting of Angiogenin, DPPIV, IGFBP-3, and uPA. In some embodiments, the MSC secretome composition further comprises about 200 pg/mL to about 800 pg/mL of at least one factor selected from the group consisting of Angiogenin, DPPIV, IGFBP-3, and uPA. In some embodiments, the MSC secretome composition further comprises about 200 pg/mL to about 700 pg/mL, about 300 pg/mL to about 800 pg/mL, about 200 pg/mL to about 500 pg/mL, or about 300 pg/mL to about 500 pg/mL of at least one factor selected from the group consisting of Angiopoietin-1, Angiopoietin-2, Amphiregulin, Endostatin, Endothelial-1, Thrombospondin-2, and Thrombospondin-1, Angiogenin, DPPIV, IGFBP-3, and uPA. In some embodiments, the MSC secretome composition further comprises about 200 pg/mL, about 300 pg/mL, about 400 pg/mL, about 500 pg/mL, about 600 pg/mL, about 700 pg/mL, or about 800 pg/mL of at least one factor selected from the group consisting of Angiopoietin-1, Angiopoietin-2, Amphiregulin, Endostatin, Endothelial-1, Thrombospondin-2, and Thrombospondin-1, Angiogenin, DPPIV, IGFBP-3, and uPA. In some embodiments, the MSC secretome composition comprises about 200 pg/mL to about 800 pg/mL, about 300 pg/mL to 800 pg/mL, about 200 pg/mL to about 500 pg/mL, or about 300 pg/mL to about 500 pg/mL of Angiogenin. In some embodiments, the MSC secretome composition further comprises about 200 pg/mL to about 800 pg/mL, about 300 pg/mL to about 800 pg/mL, about 200 pg/mL to about 500 pg/mL, or about 300 pg/mL to about 500 pg/mL of DPPIV. In some embodiments, the MSC secretome composition comprises about 200 pg/mL to about 800 pg/mL, about 300 pg/mL to about 800 pg/mL, about 200 pg/mL to 500 pg/mL, or about 300 pg/mL to about 500 pg/mL of IGFBP-3. In some embodiments, the MSC secretome composition comprises 200 pg/mL to about 800 pg/mL, about 300 pg/mL to 800 pg/mL, about 200 pg/mL to 500 pg/mL, or about 300 pg/mL to about 500 pg/mL of uPA.

In some embodiments, the MSC secretome further comprises "low" levels of VEGF. In some embodiments, the MSC secretome further comprises about 1 pg/mL of VEGF. In some embodiments, the MSC secretome further comprises about 10 pg/mL of VEGF. In some embodiments, the MSC secretome further comprises about 20 pg/mL of VEGF. In some embodiments, the MSC secretome further comprises about 30 pg/mL of VEGF. In some embodiments, the MSC secretome further comprises about 40 pg/mL of VEGF. In some embodiments, the MSC secretome further comprises about 50 pg/mL of VEGF. In some embodiments, the MSC secretome further comprises about 60 pg/mL of VEGF. In some embodiments, the MSC secretome further comprises about 70 pg/mL of VEGF. In some embodiments, the MSC secretome further comprises about 80 pg/mL of VEGF.

In some embodiments, the MSC secretome further comprises about 90 pg/mL of VEGF. In some embodiments, the MSC secretome further comprises about 100 pg/mL of VEGF. In some embodiments, the MSC secretome further comprises about 125 pg/mL of VEGF. In some embodiments, the MSC secretome further comprises about 150 pg/mL of VEGF. In some embodiments, the MSC secretome further comprises about 175 pg/mL of VEGF. In some embodiments, the MSC secretome further comprises 1 pg/mL to about 400 pg/mL of VEGF. In some embodiments, the MSC secretome further comprises 10 pg/mL to about 400 pg/mL of VEGF. In some embodiments, the MSC secretome further comprises 50 pg/mL to about 350 pg/mL of VEGF. In some embodiments, the MSC secretome further comprises 50 pg/mL to about 300 pg/mL of VEGF. In some embodiments, the MSC secretome further comprises 10 pg/mL to about 300 pg/mL of VEGF. In some embodiments, the MSC secretome further comprises 100 pg/mL to about 300 pg/mL of VEGF. In some embodiments, the MSC secretome further comprises less than about 200 pg/mL of VEGF. In some embodiments, the MSC secretome further comprises less than about 200 pg/mL of VEGF. In some embodiments, the MSC secretome further comprises 0 pg/mL to about 200 pg/mL of VEGF. In some embodiments, the MSC secretome further comprises 0 pg/mL to about 200 pg/mL of VEGF. In some embodiments, the MSC secretome further comprises 10 pg/mL to about 200 pg/mL of VEGF. In some embodiments, the MSC secretome further comprises 20 pg/mL to about 200 pg/mL of VEGF. In some embodiments, the MSC secretome further comprises 30 pg/mL to about 200 pg/mL of VEGF. In some embodiments, the MSC secretome further comprises 40 pg/mL to about 200 pg/mL of VEGF. In some embodiments, the MSC secretome further comprises 50 pg/mL to about 200 pg/mL of VEGF. In some embodiments, the MSC secretome further comprises 60 pg/mL to about 200 pg/mL of VEGF. In some embodiments, the MSC secretome further comprises 70 pg/mL to about 200 pg/mL of VEGF. In some embodiments, the MSC secretome further comprises 80 pg/mL to about 200 pg/mL of VEGF. In some embodiments, the MSC secretome further comprises 90 pg/mL to about 200 pg/mL of VEGF. In some embodiments, the MSC secretome further comprises 100 pg/mL to about 200 pg/mL of VEGF. In some embodiments, the MSC secretome further comprises 10 pg/mL to about 150 pg/mL of VEGF. In some embodiments, the MSC secretome further comprises 20 pg/mL to about 150 pg/mL of VEGF. In some embodiments, the MSC secretome further comprises 30 pg/mL to about 150 pg/mL of VEGF. In some embodiments, the MSC secretome further comprises 40 pg/mL to about 150 pg/mL of VEGF. In some embodiments, the MSC secretome further comprises 50 pg/mL to about 150 pg/mL of VEGF. In some embodiments, the MSC secretome further comprises 60 pg/mL to about 150 pg/mL of VEGF. In some embodiments, the MSC secretome further comprises 70 pg/mL to about 150 pg/mL of VEGF. In some embodiments, the MSC secretome further comprises 80 pg/mL to about 150 pg/mL of VEGF. In some embodiments, the MSC secretome further comprises 90 pg/mL to about 150 pg/mL of VEGF. In some embodiments, the MSC secretome further comprises 100 pg/mL to about 150 pg/mL of VEGF. In some embodiments, the MSC secretome further comprises 10 pg/mL to about 100 pg/mL of VEGF. In some embodiments, the MSC secretome further comprises 20 pg/mL to about 100 pg/mL of VEGF. In some embodiments, the MSC secretome further comprises 30 pg/mL to about 100 pg/mL of VEGF. In some embodiments, the MSC secretome further comprises 40 pg/mL to about 100 pg/mL of VEGF. In some embodiments, the MSC secretome further comprises 50 pg/mL to about 100 pg/mL of VEGF. In some embodiments, the MSC secretome further comprises 60 pg/mL to about 100 pg/mL of VEGF. In some embodiments, the MSC secretome further comprises 70 pg/mL to about 100 pg/mL of VEGF. In some embodiments, the MSC secretome further comprises 80 pg/mL to about 100 pg/mL of VEGF. In some embodiments, the MSC secretome further comprises 90 pg/mL to about 100 pg/mL of VEGF. In some embodiments, the MSC secretome further comprises 100 pg/mL to about 100 pg/mL of VEGF.

In some embodiments of the MSC secretome composition the level of VEGF is 5-10 fold lower than the level of Serpin E1. In some embodiments of the MSC secretome composition the level of VEGF is 6-10 fold lower than the level of Serpin E1. In some embodiments of the MSC secretome composition the level of VEGF is 7-10 fold lower than the level of Serpin E1. In some embodiments of the MSC secretome composition the level of VEGF is 8-10 fold lower than the level of Serpin E1. In some embodiments of the MSC secretome composition the level of VEGF is 9-10 fold lower than the level of Serpin E1. In some embodiments of the MSC secretome composition the level of VEGF is 5-fold lower than the level of Serpin E1. In some embodiments of the MSC secretome composition the level of VEGF is 6-fold lower than the level of Serpin E1. In some embodiments of the MSC secretome composition the level of VEGF is 7-fold lower than the level of Serpin E1. In some embodiments of the MSC secretome composition the level of VEGF is 8-fold lower than the level of Serpin E1. In some embodiments of the MSC secretome composition the level of VEGF is 9-fold lower than the level of Serpin E1. In some embodiments of the MSC secretome composition the level of VEGF is 10-fold lower than the level of Serpin E1.

In some embodiments, the MSC secretome composition does not comprise and/or comprises very low levels of bFGF, PLGF, and PDGF. In some embodiments, the MSC secretome composition comprises less than about 200 pg/mL, less than about 150 pg/mL, less than about 100 pg/mL, less than about 75 pg/mL, less than about 50 pg/mL, or less than about 25 pg/mL bFGF, PLGF, and/or PDGF. In some embodiments, the MSC secretome composition comprises less than about 200 pg/mL, less than about 150 pg/mL, less than about 100 pg/mL, less than about 75 pg/mL, less than about 50 pg/mL, or less than about 25 pg/mL bFGF, PLGF, and PDGF. In some embodiments, the MSC secretome composition does not comprise bFGF, PLGF, and/or PDGF. In some embodiments, the MSC secretome composition does not comprise bFGF, PLGF, and PDGF. In some embodiments, the MSC secretome composition comprises less than about 200 pg/mL, less than about 150 pg/mL, less than about 100 pg/mL, less than about 75 pg/mL, less than about 50 pg/mL, or less than about 25 pg/mL of bFGF. In some embodiments, the MSC secretome composition does not comprise bFGF. In some embodiments, the MSC secretome composition comprises less than about 200 pg/mL, less than about 150 pg/mL, less than about 100 pg/mL, less than about 75 pg/mL, less than about 50 pg/mL, or less than about 25 pg/mL of PLGF. In some embodiments, the MSC secretome composition does not comprise PLGF. In some embodiments, the MSC secretome composition comprises less than about 200 pg/mL, less than about 150 pg/mL, less than about 100 pg/mL, less than about 75 pg/mL, less than about 50 pg/mL, or less than about 25 pg/mL of PDGF. In some embodiments, the MSC secretome composition does not comprise PDGF. In some embodiments, the MSC secretome composition does not comprise bFGF. In some embodiments, the MSC secretome composition does not comprise PLGF. In some embodiments, the MSC secretome composition does not comprise PDGF. In some embodiments, the MSC secretome composition comprises very low levels of bFGF, PLGF, and PDGF. In some embodiments, the MSC secretome composition comprises very low levels of bFGF. In some embodiments, the MSC secretome composition comprises very low levels of PLGF. In some embodiments, the MSC secretome composition comprises very low levels of PDGF.

In some embodiments, the MSC secretome composition comprises Apolipoprotein A1, Complement Factor D, C-reactive protein, Cystatin C, DKK-1, Emmprin, Osteopontin, vitamin D BP, MIF, RANTES, uPAR, IL-17a, GDF-15, and/or IFNγ.

In some embodiments, the MSC secretome composition comprises 1 ng/mL-100 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 10 ng/mL-100 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 10 ng/mL-90 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 10 ng/mL-80 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 20 ng/mL-100 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 30 ng/mL-100 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 40 ng/mL-100 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 50 ng/mL-100 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 10 ng/mL-70 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 10 ng/mL-60 ng/mL of at least one factor selected from the group consisting of Serpin E1, TIMP-1, Thrombospondin-1, Pentraxin-3 (TSG-14), Platelet Factor 4, and Serpin F1. In some embodiments, the MSC secretome composition comprises 10 ng/mL-50 ng/mL of at least one factor selected from the group consisting of Serpin E1, TIMP-1, Thrombospondin-1, Pentraxin-3 (TSG-14), Platelet Factor 4, and Serpin F1.

In some embodiments, the MSC secretome composition comprises:
  i. 0.3-4.5 ng/mL HGF;
  ii. 0.5-20 ng/mL Pentraxin-3 (TSG-14);
  iii. 100-600 pg/mL VEGF;
  iv. 10-200 ng/mL TIMP-1;
  v. 20-80 ng/mL Serpin E1; and
  vi. <5 ng/mL IL-8.

In some embodiments, the MSC secretome composition comprises:
  i. 1.5-3.5 ng/mL HGF;
  ii. 5-15 ng/mL Pentraxin-3 (TSG-14);
  iii. 200-400 pg/mL VEGF;
  iv. 50-120 ng/mL TIMP-1;
  v. 30-70 ng/mL Serpin E1; and
  vi. <3 ng/mL IL-8.

In some embodiments, the MSC secretome composition comprises:
  i. 1.5-2.5 ng/mL HGF;
  ii. 8-12 ng/mL Pentraxin-3 (TSG-14);
  iii. 250-350 pg/mL VEGF;
  iv. 70-110 ng/mL TIMP-1;
  v. 30-70 ng/mL Serpin E1; and
  vi. <2 ng/mL IL-8.

In some embodiments, the MSC secretome composition comprises:
  i. 2.0+/−0.3 ng/mL HGF;
  ii. 9.8+/−0.5 ng/mL Pentraxin-3 (TSG-14);
  iii. 304+/−44 pg/mL VEGF;
  iv. 90+/−20 ng/mL TIMP-1;
  v. 49.2+/−10 ng/mL Serpin E1; and
  vi. <1 ng/mL IL-8.

In some embodiments, the MSC secretome composition is formulated at a pH of about pH 4.5 to about pH 8. In some embodiments, the MSC secretome composition is formulated at a pH of about pH 4.7 to about pH 7.8. In some embodiments, the MSC secretome composition is formulated at a pH of about pH 5.0 to about pH 7.5. In some embodiments, the MSC secretome composition is formulated at a pH of about pH 5.5 to about pH 7.5. In some embodiments, the MSC secretome composition is formulated at a pH of about pH 6 to about pH 7.5.

In some embodiments, the MSC secretome composition is formulated at a pH of about pH 4.5, about pH 5.0, about pH 5.5, about pH 6.0, about pH 6.5, about pH 7.0, about pH 7.4, about pH 8.0. In some embodiments, the MSC secretome composition is formulated at a pH of about pH 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0.

In some embodiments, the MSC secretome composition does not comprise certain components. In some embodiments, the MSC secretome composition does not comprise certain components found in cellular media. In some embodiments, the MSC secretome composition does not comprise one or more components selected from the group consisting of xenobiotic components (for example, animal serum); Phenol red; peptides and biomolecules <3 kDa; antibiotics; protein aggregates (for example, protein aggregates >200 nm); cells; cell debris (cell debris do not include exosomes/Extracellular Vesicles (EVs); for example, non-exosome, non-EV cell debris); hormones (for example, hormones include, but are not limited to insulin and/or hydrocortisone); and/or L-glutamine. In some embodiments, the MSC secretome composition does not comprise xenobiotic components. In some embodiments, the MSC secretome composition does not comprise Phenol red. In some embodiments, the MSC secretome composition does not comprise peptides and biomolecules <3 kDa. In some embodiments, the MSC secretome composition does not comprise antibiotics. In some embodiments, the MSC secretome composition does not comprise protein aggregates (for example, protein aggregates >200 nm). In some embodiments, the MSC secretome composition does not comprise cells. In some embodiments, the MSC secretome composition does not comprise cell debris (cell debris do not include exosomes/EVs; for example, non-exosome, non-EV cell debris). In some embodiments, the MSC secretome composition does not comprise hormones (for example, hormones include, but are not limited to insulin and/or hydrocortisone. In some embodiments, the MSC secretome composition does not comprise L-glutamine.

In some embodiments, the MSC secretome further comprises mannitol, lactose, sorbitol, xylitol, sucrose, trehalose, mannose, maltose, lactose, glucose, raffinose, cellobiose, gentiobiose, isomaltose, arabinose, glucosamine, fructose, dextrose, and/or combinations thereof. In some embodiments, the MSC secretome further comprises phosphate. In some embodiments, the phosphate source is sodium phosphate or potassium phosphate. In some embodiments, the phosphate source is sodium phosphate. In some embodiments, the phosphate source is potassium phosphate. In some embodiments, the MSC secretome further comprises mono/di-sodium phosphate, mannitol, and trehalose, wherein the composition has a pH of about pH 7.4.

In some embodiments, the MSC secretome composition can comprise one or more additional agents including but not limited to glycine, glycerol, sodium chloride, potassium chloride, and/or dextrose. In some embodiments, the MSC secretome composition can comprise one or more additional agents selected from the group consisting of glycine, glycerol, sodium chloride, potassium chloride, and dextrose. In some embodiments, the MSC secretome composition can comprise one or more additional agents selected from the group consisting of glycine and glycerol, and dextrose. In some embodiments, the MSC secretome composition can comprise one or more additional agents selected from the group consisting of sodium chloride and potassium chloride.

In some embodiments, the MSC secretome composition is formulated in a buffer system. In some embodiments, the MSC secretome composition is formulated in a buffer system including but not limited to di/mono sodium phosphate, sodium citrate/citric acid, boric acid/sodium citrate, boric acid/sodium tetraborate, and/or citric acid/disodium phosphate. In some embodiments, the MSC secretome composition is formulated in a buffer system selected from the group consisting of di/mono sodium phosphate, sodium citrate/citric acid, boric acid/sodium citrate, boric acid/sodium tetraborate, and/or citric acid/disodium phosphate. In some embodiments, the MSC secretome composition is formulated in a di/mono sodium phosphate buffer system. In some embodiments, the MSC secretome composition is formulated in sodium citrate/citric acid buffer system. In some embodiments, the MSC secretome composition is formulated in a boric acid/sodium citrate buffer system. In some embodiments, the MSC secretome composition is formulated in a boric acid/sodium tetraborate buffer system. In some embodiments, the MSC secretome composition is formulated in a citric acid/disodium phosphate buffer system.

In some embodiments, the phosphate source is sodium phosphate or potassium phosphate. In some embodiments, the phosphate source is sodium phosphate. In some embodiments, the phosphate source is potassium phosphate. In some embodiments, the MSC secretome composition comprises di-sodium phosphate/citric acid, mannitol, and trehalose, wherein the composition has a pH of about pH 6.4.

In some embodiments, the MSC secretome composition further comprises a tonicity adjusting or tonicity modifying agent. In some embodiments, tonicity adjusting or tonicity modifying agent includes but is not limited to NaCl, KCl, mannitol, dextrose, sucrose, sorbitol, and/or glycerin. In some embodiments, tonicity adjusting or tonicity modifying agent is selected from the group consisting of NaCl, KCl, mannitol, dextrose, sucrose, sorbitol, and/or glycerin.

In some embodiments, the MSC secretome composition further comprises an adhesive agent. In some embodiments, the MSC secretome composition further comprises an adhesive agent including but not limited to hypromellose, Poloxamer 407, Poloxamer 188, Poloxamer 237, Poloxamer 338, Hypromellose, (HPMC), HEC, polycarbophil, polyvinylpyrrolidone (PVP), PVA (polyvinyl alcohol, polyimide, sodium hyaluronate, gellan gum, poly(lactic acid-co-glycolic acid) (PLGA), polysiloxane, polyimide, carboxymethylcellulose (CMC), or hydroxypropyl methylcellulose (HPMC), hydroxy methyl cellulose, hydroxy ethyl cellulose, sodium carboxy methyl cellulose, fibrin glue, polyethyelene glycol, and GelCORE. In some embodiments, the adhesive agent is hypromellose. In some embodiments, the adhesive agent is fibrin glue. In some embodiments, the adhesive agent is a polyethyelene glycol. In some embodiments, the adhesive agent is GelCORE (see, Sani, et al., Science Advances, Vol. 5, no. 3 (2019)).

In some embodiments, the MSC secretome composition comprises (a) processed conditioned medium comprising the MSC secretome produced by any one of the methods described herein; and (b) a polymer. In some embodiments, the MSC secretome composition comprises conditioned medium comprising the MSC secretome which is produced as described herein and a polymer. In some embodiments, the MSC secretome composition comprises processed conditioned medium comprising the MSC secretome which is produced as described herein and a polymer. In some embodiments the polymer can be a biodegradable polymer from which the MSC secretome and/or processed MSC secretome components can be released. In some embodiments, the polymer enables sustained (slow) release of the MSC secretome components.

In some embodiments, the MSC secretome compositions provided herein are in the form of a therapeutic bandage (e.g., a polymer impregnated with MSC secretome composition). The therapeutic bandage may be configured as needed, depending on the application. In some embodiments, the bandage is in the form or a patch or is configured as mesh.

In some embodiments, the MSC secretome compositions exhibit bio-penetrance, for example, ocular penetration, corneal penetration, and/or corneal permeation. In some embodiments, the MSC secretome composition exhibits the ability to be absorbed by the eye. In some embodiments, the MSC secretome composition exhibits inherent bio-penetrance. In some embodiments, the MSC secretome composition exhibits excipient-enabled bio-penetrance. In some embodiments, the MSC secretome composition exhibits bio-penetrance due to upregulation of the smaller factors. In some embodiments, the MSC secretome composition exhibits bio-penetrance due to the presence of a biopreservative. In some embodiments, the MSC secretome composition exhibits bio-penetrance due to the presence of the biopreservative benzalkonium chloride.

In some embodiments, the MSC secretome compositions exhibit long half-life and/or have increased stability as compared to other treatments. In some embodiments, the MSC secretome compositions as provided herein allow for an upregulation of proteins that are allow for increased stability of the MSC secretome. In some embodiments, the MSC secretome compositions as provided herein allow for upregulating chaperone proteins to improve stability of other proteins in the MSC secretome.

In some embodiments, the MSC secretome compositions exhibit ultrapotency when administered to a subject in need thereof. In some embodiments, the MSC secretome compositions allow for therapeutic efficacy with one drop or one administration per day.

C. Methods of Producing/Manufacturing

According to the present invention, conditioned medium (and, thus, mesenchymal stem cell secreted factors) can be obtained from mesenchymal stem cells obtained from the patient or individual to be treated (the patient in need thereof) or from another (donor) individual, such as a young and/or healthy donor and/or from mesenchymal stem cells obtained commercially. For example, MSC obtained from the individual to be treated (autologous stem cells) or from a donor (allogeneic stem cells), can be used to produce the conditioned medium described herein, which can then be further processed into a MSC secretome composition as described herein. In some embodiments, MSCs can also be obtained from commercial suppliers. In some embodiments, commercially obtained MSCs can used in MSC secretome production.

According to the present invention, the method of making a anti-angiogenic mesenchymal stem cell (MSC) secretome composition comprising:
  i. culturing mesenchymal stem cells (MSCs) in a first culture media;
  ii. removing the first culture media from step (i) from the MSCs;
  iii. washing the MSCs in step (ii);

iv. adding a second culture media and culturing for about 1-5 days;
v. harvesting the second culture media from step (iv) as conditioned media; and
vi. processing the conditioned media in step (v) into the MSC secretome composition as described herein.

In some embodiments, culturing can be performed using a bioreactor system for culturing cells. In some embodiments, culturing can be performed using a bioreactor system for culturing stem cells. In some embodiments, culturing can be performed using a bioreactor system for culturing mesenchymal stem cells. In some embodiments, culturing can be performed using a PBS Vertical Wheel™ Mixing Technololgy.

In some embodiments, in step (iv) processing the conditioned media in step (v) into the secretome composition comprises:
a) filtering the harvested conditioned media from step (v) to remove cell particulate;
b) concentrating the filtered conditioned media from step (a);
c) buffer exchanging with the formulation buffer.

In some embodiments, step c) comprises buffer exchanging with a buffer system selected from the group consisting of di/mono sodium phosphate, sodium citrate/citric acid, boric acid/sodium citrate, boric acid/sodium tetraborate, and citric acid/disodium phosphate.

In some embodiments, the filtering step (a) comprises the use of a 0.45 µm filter, a 0.22 µm filter, 0.8 µm filter, and 0.65 micron, a low protein binding PVDF membranes, and/or PES (polyethersulfone). In some embodiments, the filtering step (a) comprises the use of a 0.45 µm filter. In some embodiments, the filtering step (a) comprises the use of a 0.22 µm filter. In some embodiments, the filtering step (a) comprises the use of 0.8 µm filter. In some embodiments, the filtering step (a) comprises the use of 0.65 micron. In some embodiments, the filtering step (a) comprises the use of low protein binding PVDF membranes. In some embodiments, the filtering step (a) comprises the use of PES (polyethersulfone).

In some embodiments, the concentration step (b) comprises using a hollow fiber filters, tangential flow filtration systems, or centrifugation based size exclusion techniques. In some embodiments, the concentration step (b) comprises using a hollow fiber filters technique. In some embodiments, the concentration step (b) comprises using a tangential flow filtration systems. In some embodiments, the concentration step (b) comprises using a centrifugation based size exclusion technique.

In some embodiments, the centrifugation based size exclusion techniques employs a 3-10 kDa MW cutoff. In some embodiments, the centrifugation based size exclusion techniques employs at least a 3 kDa MW cutoff, at least a 4 kDa MW cutoff, at least a 5 kDa MW cutoff, at least a 6 kDa MW cutoff, at least a 7 kDa MW cutoff, at least a 8 kDa MW cutoff, at least a 9 kDa MW cutoff, at least a 10 kDa MW cutoff, at least a 11 kDa MW cutoff, at least a 12 kDa MW cutoff, at least a 13 kDa MW cutoff, at least a 14 kDa MW cutoff, at least a 15 kDa MW cutoff, at least a 16 kDa MW cutoff, at least a 17 kDa MW cutoff, at least a 18 kDa MW cutoff, at least a 19 kDa MW cutoff, at least a 20 kDa MW cutoff, at least a 21 kDa MW cutoff, at least a 22 kDa MW cutoff, at least a 23 kDa MW cutoff, at least a 24 kDa MW cutoff, at least a 25 kDa MW cutoff, at least a 26 kDa MW cutoff, at least a 27 kDa MW cutoff, at least a 28 kDa MW cutoff, at least a 29 kDa MW cutoff, and/or at least a 30 kDa MW cutoff.

In some embodiments, the method produces an MSC secretome composition and/or formulation as described herein above. In some embodiments, the first and/or second culture medium are MSC Media and/or MSC-XF.

MSCs, or cells differentiated from MSCs, can be made to produce a conditioned media comprising the desired secretome, e.g., which comprises desired cytokines and/or desired therapeutic properties as described herein. For example, the secretome can be produced from MSCs of a super donor cell line. The secretome can also be produced from MSCs obtained commercially. In come embodiments, allogeneic MSCs (and/or cells derived therefrom) and/or allogeneic MSC-derived secretome compositions can be prepared and stored for large groups of individuals. Allogeneic MSCs (and/or cells derived therefrom) and/or MSC-derived secretome compositions can be made in advance so that they are ready when people need them. In certain embodiments, MSCs (and/or cells derived therefrom) and/or MSC-derived secretome compositions can be processed to manufacture a more concentrated solution or composition (e.g., a mesenchymal stem cell derived secretome composition or MSC secretome composition as described herein).

In some embodiments, the initial culture medium and the first culture medium are different. In some embodiments, the initial culture medium and the first culture medium are the same. Non-limiting examples of cell culture medium or media useful in culturing MSCs to produce conditioned media comprising the MSC secretome according to the present invention include hMSC Media Booster XFM, hMSC High Performance Basal Media, Minimum Essential Medium Eagle (MEME), ADC-1, LPM (Bovine Serum Albumin-free), F10 (HAM), F12 (HAM), DCCM1, DCCM2, RPMI 1640, BGJ Medium (with and without Fitton-Jackson Modification), StemPro, MSCGro, MesenCult, NutriStenm, Basal Medium Eagle (BME—with the addition of Earle's salt base), Dulbecco's Modified Eagle Medium (DMEM—with or without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Alpha (MEM-alpha), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is MEM-alpha. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

In some embodiments, the cell culture medium for mesenchymal stem cells can be a serum-free medium. In some embodiments, the cell culture medium n for mesenchymal stem cells can be supplemented with serum. In some embodiments, the cell culture medium for mesenchymal stem cells can be supplemented human platelet lysate. In some embodiments, the serum can include fetal bovine serum (FBS). In some embodiments, the cell culture medium for mesenchymal stem cells can be supplemented with serum such as fetal serum of bovine or other species.

In some embodiments, the cell culture medium for mesenchymal stem cells can be supplemented with other components to facilitate cell growth and/or promote cell health, such as mercaptoethanol and/or antibiotics. In some embodiments, the cell culture medium for mesenchymal stem cells is not supplemented with antibiotics.

In some embodiments, the oxygen percentage is varied to facilitate cell growth and/or promote cell health. In some embodiments, the oxygen is at 5%, 10%, 15% 20%3, or 25% volume to facilitate cell growth and/or promote cell health. In some embodiments, the mesenchymal stem cells are grown under partial oxygen pressure to facilitate cell growth and/or promote cell health. In some embodiments, the mesenchymal stem cells are grown under a low oxygen partial pressure environment to facilitate cell growth and/or promote cell health.

In one aspect, the present invention is directed to conditioned medium (CM) comprising biological factors secreted by mesenchymal stem cells, which can be referred to as conditioned media comprising the MSC secretome. The conditioned medium can be obtained by culturing mesenchymal stem cells in media, as described herein, and separating the resulting media, which contains mesenchymal stem cells and their secreted mesenchymal stem cell products (referred to as biological factors and/or the secretome) into the components parts of the conditioned medium contain the secretome and mesenchymal stem cells grown in the conditioned media. The conditioned medium once separated comprises the mesenchymal stem cell secretome and can be further processed and/or used according to the methods described herein and is substantially free of mesenchymal stem cells (may contain a small percentage of stem cells and/or trace amounts of stem cells) or free of mesenchymal stem cells. The MSC secretome comprises a variety of biological factors including hormones, cytokines, extracellular matrix, proteins, vesicles, antibodies, chemokines, receptors, inhibitor, and granules. As described herein, the conditioned medium or media (CM or conditioned media comprising the MSC secretome) comprising the MSC secretome can be further processed, producing concentrated, conditioned medium (pCM or concentrated MSC secretome).

In some embodiments, the conditioned media comprising the MSC secretome or concentrated MSC secretome is produced by culturing mesenchymal stem cells in culture medium, replacing culture medium in which the mesenchymal stem cells have been cultured. In some embodiments, the resultant conditioned media comprising the MSC secretome is harvested (collected), then processed to produce concentrated MSC secretome. In certain embodiments, processing of the harvested conditioned media comprising the MSC secretome includes removal of some, most, or essentially all of the medium, or removal of some, most, or essentially all of selected components of the conditioned medium.

In some embodiments, the harvested conditioned media comprising the MSC secretome is filtered to produce concentrated MSC secretome. In some embodiments, the harvested conditioned media comprising the MSC secretome is ultra-filtered to produce concentrated MSC secretome.

In one aspect, provided herein are methods of producing processed conditioned medium, comprising (a) culturing stem cells in a cell culture medium, thereby generating conditioned medium that comprises factors secreted by the mesenchymal stem cells (e.g., conditioned media comprising the mesenchymal stem cell secretome); (b) harvesting the conditioned medium thereby producing harvested conditioned medium (e.g., harvested mesenchymal stem cell secretome); and (c) filtering harvested conditioned medium (e.g., harvested mesenchymal stem cell secretome) to produce processed conditioned medium (mesenchymal stem cell secretome). In some embodiments, the stem cells of (a) are cultured (have been cultured) in growth medium prior to being cultured in growth factor-free medium. Thus, in some embodiments, the methods comprise: (a) culturing mesenchymal stem cells in a first growth medium; (b) replacing the first growth medium with a second growth medium and culturing the stem cells in the second growth medium, thereby generating conditioned media comprising the mesenchymal stem cell secretome; (c) harvesting the conditioned media comprising the mesenchymal stem cell secretome, thereby producing harvested conditioned medium comprising the mesenchymal stem cell secretome; and (d) filtering harvested conditioned medium to produce processed conditioned medium comprising the mesenchymal stem cell secretome.

In some embodiments, the stem cells are mesenchymal stem cells. Mesenchymal stem cells (MSCs) are multipotent (capable of differentiating into multiple, but not all, cell lineages) nonhematopoietic (non-blood) stem cells isolated from (derived from) a variety of adult tissues, including bone marrow and adipose tissue. In certain embodiments, the mesenchymal stem cells are isolated from bone marrow. "Isolated" refers to cells removed from their original environment. MSCs may differentiate into cells of mesodermal lineage, for example, adipocytes, osteoblasts, and chondrocytes. MSCs have a small cell body with few cell processes that are long and thin. The cell body contains a large, round nucleus with a prominent nucleolus, which is surrounded by finely dispersed chromatin particles, giving the nucleus a clear appearance. The remainder of the cell body contains a small amount of Golgi apparatus, rough endoplasmic reticulum, mitochondria, and polyribosomes. The cells, which are long and thin, are widely dispersed and the adjacent extracellular matrix is populated by a few reticular fibrils but is devoid of the other types of collagen fibrils [Brighton, et al. 1991 The Journal of Bone and Joint Surgery 73(6):832-47]. MSCs described herein may express the following molecular marker (protein molecule characteristic of plasma membrane of a cell or cell type) profiles: bone morphogenic protein receptor "1" (BMPR$^+$); CD34$^+$Scal$^+$Lin$^-$; CD44$^+$; c-kit$^+$; Sca-1$^+$; Thy-1$^+$; NOTCH3; JAG1; ITGA11. MSCs may also express other cell type-specific markers (see, the World Wide Web at stemcells.nih.gov; Kaltz, et al. 2010 Exp Cell Res October 1; 316(16):2609-17, incorporated herein by reference]. MSCs described herein may be identified based on colony-forming unit assays to detect the multipotent differentiation potential of the MSCs (to what cell types the MSCs give rise). However, cells that are somewhat differentiated (progenitor cells) can also be used.

i. MSC Secretome—Processing

The conditioned medium comprising the MSC secretome described herein can in some embodiments be collected and filtered and/or purified to remove cell particulate and/or other detrimental components. For example, as described above under step (v) harvesting the second culture media from step (iv) as conditioned media. The filtration membranes used herein may be selected from any of those known in the art having a suitable membrane and configuration, such that they are capable of retaining the desired MSC secretome components while allowing the cell particulate and/or other detrimental components pass through. Thus, one may employ any suitable membrane which permits the retention of cells under the fluid dynamic conditions selected whilst allowing the detrimental components to pass through for removal. In some embodiments, an upper limit of pore size of about 5 microns and a lower limit of about 0.1 microns would be suitable. In some embodiments, filtration can be performed using a micropore filter. In some embodiments, filtration can be performed using a 0.5 µm to a 0.2 µm filter. In some embodiments, filtration can be performed using a 0.5 µm, 0.45 µm, 0.4 µm, 0.35 µm, 0.3 µm, 0.25 µm, 0.22 µm and/or a 0.2 µm filter. In some embodiments, filtration can be performed using a 0.45 µm filter. In some embodiments, filtration can be performed using a 0.22 µm filter. In some embodiments, filtration/purification can be performed using a low protein binding polyvinylidene difluoride (PVDF) membranes. In some embodiments, filtration/purification can be performed using polyethersulfone (PES).

In some embodiments, the filtering is by ultra-filtration. In some embodiments, the conditioned medium is filtered using a filter size of 3 kD (to achieve purification, desalting, and concentration in the processed conditioned medium of molecules larger than the filter size). In some embodiments, a filter size of less than 3 kD is used to filter the conditioned medium, while in other embodiments a filter size of greater than 3 kD is used, depending on the application for which the processed conditioned medium is used. In other embodiments, ultra-filtration of harvested conditioned medium is carried out using a filter of a different pore size (e.g., 2 kD, <2 kD or >2 kD) selected to determine the size of components of the resulting processed conditioned medium comprising the MSC secretome.

In some embodiments, the detrimental components in the growth supporting media are removed by medium exchange, preferably via "cross-flow filtration". Cross-flow filtration refers to a mode of filtration where a suspension of MSC secretome cells flows substantially parallel to a filter which is permeable to a component of the suspension other than cells. The cross-flow filtration process is characterized by a set of fluid dynamic parameters including Re=Reynolds number, γw=wall shear rate, ΔP=pressure drop and TMP=transmembrane pressure. Re, γw and ΔP will depend on the geometry of the filtration system, flow conditions and fluid properties. Such cross-flow processes can, in some embodiments, include hollow fiber filtration systems as well. See, for example, U.S. Pat. No. 5,053,334, incorporated herein by reference in its entirety.

In some embodiments, the MSC secretome can be further subject to concentrated in the absence of filtration and/or after filtration. In some embodiments, the MSC secretome can be concentrated using hollow fiber tangential flow technology, or In some embodiments, the MSC secretome can be concentrated using centrifugation based size exclusion technique, for example, amicons and/or centricons can be employed during the centration step. In some embodiments, the size cutoff is a 3-10 kDa MW cutoff. In some embodiments, the molecular weight cutoff for use during centrifugation based size exclusion technique concentration methods is at least about 3 kDa, at least about 4 kDa, at least about 5 kDa, at least about 6 kDa, at least about 7 kDa, at least about 8 kDa, at least about 9 kDa, or at least about 10 kDa.

In some embodiments, the MSC secretome is concentrated about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold. In some embodiments, the MSC secretome is concentrated about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold as compared to the conditioned media prior to concentration In some embodiments, the MSC secretome is further buffer exchanged after the concentration step into the final formulation buffer. In some embodiments, the MSC secretome is further buffer exchanged after the concentration step into the final formulation buffer without an adhesive agent. In some embodiments, buffer exchange comprises altering the buffer components of the MSC secretome. In some embodiments, the MSC secretome is not diluted during the buffer exchange step. In some embodiments, the MSC secretome is diluted less than 1%, less than 5%, less than 10%, less than 15%, less than 20%, or less than 25% during the buffer exchange step.

In some embodiments, the MSC secretome is buffer exchanged after the concentration step such that the all traces of culture media components are removed. In some embodiments, the MSC secretome is buffer exchanged after the concentration step such that less than about 25%, less than about 20%, less than about 15%, less than about 10%, less than about 5%, less than about 4%, less than about 3%, less than about 2%, or less than about 1% or about 0% of the culture media components remain.

ii. MSC Secretome—Formulating

In some embodiments, the MSC secretome is prepared in a formulation comprising about 2 µg-8 µg per 1 mL of MSC secretome. In some embodiments, the MSC secretome is prepared in a formulation comprising 0.008% to 0.015% per mL of MSC secretome.

In some embodiments, the MSC secretome is prepared in a formulation comprising 2 mg-3 mg per mL of monobasic sodium phosphate. In some embodiments, the MSC secretome is prepared in a formulation comprising 4% to 5% per mL of monobasic sodium phosphate.

In some embodiments, the MSC secretome is prepared in a formulation comprising 11 mg-12 mg per mL of dibasic sodium phosphate. In some embodiments, the MSC secretome is prepared in a formulation comprising 21.5% to 23% per mL of dibasic sodium phosphate.

In some embodiments, the MSC secretome is prepared in a formulation comprising 11.5 mg-13 mg per mL of mannitol. In some embodiments, the MSC secretome is prepared in a formulation comprising 23% to 25% per mL of mannitol.

In some embodiments, the MSC secretome is prepared in a formulation comprising 23 mg-25 mg per mL of trehalose dihydrate. In some embodiments, the MSC secretome is prepared in a formulation comprising 46% to 48% per mL of trehalose dihydrate.

In some embodiments, the MSC secretome is prepared in a formulation comprising 0.5 mg-2 mg per mL of hypromellose. In some embodiments, the MSC secretome is prepared in a formulation comprising 1% to 3% per mL of hypromellose.

In some embodiments, the MSC secretome is prepared in a formulation comprising hydrochloric acid and/or sodium hydroxide. In some embodiments, the MSC secretome is prepared in a formulation comprising hydrochloric acid. In some embodiments, the MSC secretome is prepared in a formulation comprising sodium hydroxide. In some embodiments, the hydrochloric acid and/or sodium hydroxide is employed to obtain the desired pH.

In some embodiments, the MSC secretome is prepared in a formulation comprising the components as provided in Table 1 below:

TABLE 1

MSC secretome formulation embodiment.

| Constituent Present | Amount per 1 mL of product | Percent present (%) per 1 mL |
|---|---|---|
| MSC secretome | 0.006 mg (6 µg) | 0.012 |
| Monobasic sodium phosphate | 2.28 mg | 4.5 |
| Dibasic sodium phosphate | 11.45 mg | 22.4 |
| Mannitol | 12.2 mg | 24.0 |
| Trehalose Dihydrate | 24 mg | 47.1 |
| Hypromellose | 1 mg | 2.0 |
| Hydrochloric acid and/or sodium hydroxide | adjust as required | adjust as required |
| Total quantity | 50.936 mg | 100% |

D. Assay Methods/Therapeutic Properties

In some embodiments of the invention, the MSC secretome is processed to achieve certain ingredient ratios/concentrations as well as properties for the MSC secretome.

In some embodiments, the MSC secretome composition comprises ratios of anti-angiogenic to pro-angiogenic wherein the ratio is >1. In some embodiments, the MSC secretome composition comprises ratios of anti-angiogenic to pro-angiogenic wherein the ratio is >2, >3, >4, or >5. In some embodiments, the MSC secretome composition comprises an increased concentration of pro-angiogenic factors (relative to the concentration of pro-angiogenic factors in conditioned medium from which the MSC secretome composition is produced). In some embodiments, the MSC secretome composition comprises a sum of several anti-angiogenic factors that exceeds the level of VEGF. In some embodiments, the MSC secretome composition comprises a sum of several anti-angiogenic factors such that the ratio of the more than 1 anti-angiogenic factor to VEGF is >2, >3, >4, or >5. In some embodiments, the MSC secretome composition comprises one or more anti-angiogenic factor, and wherein the sum of the concentration of the one or more anti-angiogenic factors relative to the concentration of VEGF is >2, >3, >4, or >5. In some embodiments, pro-angiogenic factors include but are not limited to Serpin E1 to VEGF-A. In some embodiments, the pro-angiogenic factor is Serpin E1. In some embodiments, the pro-angiogenic factor is VEGF-A.

In some embodiments of the invention, the MSC secretome is processed to achieve certain potency performance criteria. In some embodiments, the buffer exchange step promotes obtaining a potent MSC secretome.

Extracellular Vesicles are membrane bound particles that carry cargo of soluble and insoluble substances mentioned above. The term "Extracellular Vesicles" refers a group of secreted or shedded vesicles of various species. These are generally divided into the following subtypes: 1) microvesicles or Shed microvesicles which typically exhibit a size range of 50-1500 nm; 2) exosomes which typically exhibit a size range of 30-120 nm; and 3) vesicles which typically exhibit a size range of less than 500 nm (i.e., <500 nm). (See, for example, WO2019016799, incorporated by reference herein in its entirety.) In some embodiments, the MSC secretome can be analyzed for particle count and/or to quantitate the extracellular vesicles (EVs) present in the secretome.

In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL. In some embodiments, EVs are present in a concentration of about $3.8 \times 10^5$/uL +/− $0.8 \times 10^5$.

In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL and average 110-120 nm in diameter. In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL and average 112-116 nm in diameter. In some embodiments, EVs are present in a concentration of about $2.5 \times 10^5$/uL, $2.6 \times 10^5$/uL, $2.7 \times 10^5$/uL, $2.8 \times 10^5$/uL, $2.9 \times 10^5$/uL, $3.0 \times 10^5$/uL, $3.1 \times 10^5$/uL, $3.2 \times 10^5$/uL, $3.3 \times 10^5$/uL, $3.4 \times 10^5$/uL, $3.5 \times 10^5$/uL, $3.6 \times 10^5$/uL, $3.7 \times 10^5$/uL, $3.8 \times 10^5$/uL, $3.9 \times 10^5$/uL, $4.0 \times 10^5$/uL, $4.1 \times 10^5$/uL, $4.2 \times 10^5$/uL, $4.3 \times 10^5$/uL, $4.4 \times 10^5$/uL, $4.5 \times 10^5$/uL, $4.6 \times 10^5$/uL, $4.7 \times 10^5$/uL, $4.8 \times 10^5$/uL, $4.9 \times 10^5$/uL, or about $5.0 \times 10^5$/uL and average 114 nm in diameter. In some embodiments, EVs are present in a concentration of about $3.8 \times 10^5$/uL +/− $0.8 \times 10^5$ and average 114 nm in diameter.

i. MSC Secretome—Therapeutic Properties

The MSC secretome of the present disclosure exhibits a variety of therapeutic properties, including for example, anti-angiogenic properties (blood vessels and/or lymphatic vessels), anti-fibrotic properties, anti-inflammatory properties, properties promoting cell migration and proliferation, mitogenic promoting properties, anti-oxidative stress/damage properties, In some embodiments, anti-angiogenic (blood vessels and/or lymphatic vessels) properties can be determined by the presence and/or level of one or more factors in the MSC secretome. In some embodiments, the anti-angiogenic factors include but are not limited to one or more of PEDF, sFLT-1, lower levels of VEGF, and/or Serpin E1. In some embodiments, the anti-angiogenic factors include but are not limited to one or more of PEDF, lower levels of VEGF, and/or Serpin E1. In some embodiments, the anti-angiogenic factor is PEDF. In some embodiments, the anti-angiogenic factor is sFLT-1. In some embodiments, the anti-angiogenic factor corresponds to lower levels of VEGF. In some embodiments, the anti-angiogenic factor is Serpin E1.

In some embodiments, pro-angiogenic (blood vessels and/or lymphatic vessels) properties can be determined by the presence and/or level of one or more factors in the MSC secretome. In some embodiments, the pro-angiogenic factors includes one or more factors selected from the group consisting of VEGF, Angiogenin, IGFBP-3, uPA, Angio-1, Angio-2, Endothelial-1. In some embodiments, the pro-angiogenic factor is VEGF. In some embodiments, the pro-angiogenic factor is Angiogenin. In some embodiments, the pro-angiogenic factors is IGFBP-3. In some embodiments, the pro-angiogenic factor is uPA. In some embodiments, the pro-angiogenic factor is Angio-1. In some embodiments, the pro-angiogenic factor is Angio-2. In some embodiments, the pro-angiogenic factor is Endothelial-1.

In some embodiments, the MSC secretome exhibits anti-fibrotic properties. In some embodiments, such anti-fibrotic properties can be assayed for using standard assays. In some embodiments, the present of various factors and/or activities with regard to the MSC secretome are indicative of anti-fibrotic properties. In some embodiments, factors which are indicative of anti-fibrotic properties include but are not limited to FGF7 and/or FGF10. In some embodiments, the factor indicative of anti-fibrotic properties is FGF7. In some embodiments, the factor indicative of anti-fibrotic properties is FGF10. In some embodiments, the factor indicative of anti-fibrotic properties is HGF. In some embodiments, activities indicative of anti-fibrotic properties include, but are not limited to, activation of SMAD, inhibition of TGFβ pathway, inhibition of myofibroblast differentiation, and/or inhibition of excess ECM deposition. In some embodiments, activities indicative of anti-fibrotic properties include activation of SMAD. In some embodiments, activities indicative of anti-fibrotic properties include inhibition of TGFβ pathway. In some embodiments, activities indicative of anti-fibrotic properties include inhibition of myofibroblast differentiation. In some embodiments, activities indicative of anti-fibrotic properties include inhibition of excess ECM deposition.

In some embodiments, the MSC secretome exhibits anti-inflammatory properties. In some embodiments, the MSC secretome inhibits inflammation. In some embodiments, the MSC secretome inhibits inflammation by 5%, 10%, 15%, 20%, 30%, 40%, 50%, 60%, 70%, 80%. 90%, or 100% (e.g., complete reduction in inflammation). In some embodiments, the MSC secretome prevents degranulation of mast cells.

In some embodiments, the MSC secretome promotes cell migration and proliferation, including for example, mitogenic and motogenic activities. In some embodiments, the MSC secretome promotes mitogenic activities. In some embodiments, the MSC secretome promotes motogenic activities. In some embodiments, the MSC secretome comprises FGF7, which provides for the cell migration and proliferation activities of the MSC secretome.

In some embodiments, the MSC secretome comprises FGF7, which provides for the cell migration and proliferation activities of the MSC secretome.

In some embodiments, the MSC secretome comprises HGF, which provides for the cell migration and proliferation activities of the MSC secretome.

In some embodiments, the MSC secretome comprises anti-apoptotic agents, which provides for the cell migration and proliferation activities of the MSC secretome. In some embodiments, the MSC secretome comprises anti-apoptotic agents include but are not limited to FGF-2, HGF and IGF-1, and which provide for the cell migration and proliferation activities of the MSC secretome. In some embodiments, the MSC secretome comprises anti-apoptotic agents selected from the group the consisting of FGF-2, HGF and IGF-1, and which provide for the cell migration and proliferation activities of the MSC secretome.

In some embodiments, the MSC secretome comprises NGF, which provides for the cell migration and proliferation activities of the MSC secretome.

In some embodiments, the MSC secretome provides for anti-oxidative stress and or reduction in cellular damage. In some embodiments, the MSC secretome comprises anti-oxidative stress and reduction in cellular damage factors. In some embodiments, the anti-oxidative stress and reduction in cellular damage factors include but are not limited to SOD-1, SOD-2, SOD-3, HO-1. In some embodiments, the anti-oxidative stress and reduction in cellular damage factor is selected from the group consisting of SOD-1, SOD-2, SOD-3, HO-1.

ii. MSC Secretome—Biophysical/Biochemical Properties
Biochemical and Biophysical Characterization:

In some embodiments, the present invention provides methods for characterization of the MSC secretome. In some embodiments, the MSC secretome characterization will include: 1) a comprehensive and/or quantitative mapping of the molecular entities in the MSC secretome; 2) measuring the contributions of select factors to biological activity; and 3) measuring biophysical parameters. In some embodiments, in order to determine the properties of the MSC secretome, various potency assays can be performed on the MSC secretome as described herein. In some embodiments, the MSC secretome can be subjected to a comprehensive and/or quantitative mapping of the molecular entities in the MSC secretome; 2) measuring the contributions of select factors to biological activity; and 3) measuring biophysical parameters. In some embodiments, characterization assays include but are not limited to biophysical assays, biochemical assays, and bioassays. In some embodiments, characterization assays can include but are not limited to physical component characterizations, oxidative stress assays, safety analysis, stability assays, proliferation assays, migration assays, neovascularization assays, differentiation/scarring assays, and inflammation assays. In some embodiments, characterization assays are selected from the group consisting of physical component characterizations, oxidative stress assays, safety analysis, stability assays, proliferation assays, migration assays, neovascularization assays, differentiation/scarring assays, and inflammation assays.

Physical Component Characterizations:

In some embodiments, the characterization of the MSC secretome comprises a method employing a combination of bioanalytical techniques. In some embodiments, the characterization of the MSC secretome comprises determining the physical components of the MSC secretome. In some embodiments, characterization of the MSC secretome includes employing protein arrays, enzyme-linked immunosorbent assays (ELISAs), mass spectrometry, and immunoblotting. In some embodiments, the MSC secretome characterization can be used to identify the molecules in the MSC secretome. In some embodiments, protein arrays can be employed to identify factors in the MSC secretome. In some embodiments, mass spectrometry can be employed to determine the presence of one or more factors in the MSC secretome. In some embodiments, quantitative techniques can be employed to measure the levels of one or more factors. In some embodiments, quantitative techniques such as ELISA can be employed to measure the levels of each factor.

In some embodiments, the secretome comprises protein factors and extracellular vesicles (EVs). In some embodiments, the MSC secretome comprises trophic factors. In some embodiments, the protein factors of the MSC secretome comprise Pentraxin-3, TIMP-1, Serpin E1, TSP-1, HGF. In some embodiments, the MSC secretome comprises EVs. In some embodiments, the MSC secretome is analyzed for simple lipid content in order to quantitatively measure total lipid. In some embodiments, the EV fraction if the MSC secretome can be evaluated for EV markers. In some embodiments, the EV fraction if the MSC secretome can be evaluated for EV markers, including but not limited to AUX, TSG101, CD63, CD9, and CD8.

In some embodiments, the secretome comprises extracellular vesicles (EVs) in a size range of 30-200 nm and $1 \times 10^8$ to $5 \times 10^9$ EVs per mL.

In some embodiments, depletion studies can be performed to distill the individual contributions of critical factors. In some embodiments, using an antibody-based pulldown method, defined factors can be removed from the MSC secretome. In some embodiments, depletion can be verified by western blot and then evaluated by one or more bioassays, as described herein below. In some embodiments, depletion studies can be performed to evaluate the contributions of the protein fraction and the EV fraction. In some embodiments, TIMP1 and/or Serpin E1 can be depleted. In some embodiments, TIMP1 and/or Serpin E1 can be depleted.

Oxidative Stress:

In some embodiments, oxidative stress prevention assays can be performed on the MSC secretome. In some embodiments, the MSC secretome prevents corneal epithelium damage. In some embodiments, the MSC secretome reduces the presence of inflammation. In some embodiments, the MSC secretome reduces the presence of inflammation as determined by an increase in the present of anti-inflammation markers. In some embodiments, the MSC secretome reduces the presence of inflammation as determined by an increase in the present of anti-inflammation markers, such as, for example, IL-8.

Safety Characterization:

In some embodiments, the MSC secretome can be evaluated for blood compatibility and implementing tests for sterility as well as pyrogen and endotoxin levels. In some embodiments, the MSC secretome can be evaluated blood compatibility. In some embodiments, evaluating blood compatibility includes assays for hemolysis and hemagglutination. In some embodiments, the MSC secretome does not exhibit detrimental effects with systemic exposure. In some embodiments, the MSC secretome does not exhibit detrimental effects with systemic exposure, such as with severe ocular burns. In some embodiments, the MSC secretome does not exhibit hemagglutination activity. In some embodiments, the MSC secretome does not induce hemolysis. In some embodiments, the MSC secretome does not induce hemolytic activity.

In some embodiments, the MSC secretome can be sterile such that it can be administered as part of a pharmaceutical formulation. In some embodiments, the MSC secretome can be free or substantially free of endotoxins. In some embodiments, the MSC secretome can be free or substantially free of microorganisms.

Stability:

In some embodiments, the biophysical characteristics of the MSC secretome can be evaluated and/or determined. In some embodiments, the fluorescence, static light scattering and dynamic light scatting to characterize protein stability metrics. In some embodiments, the following parameters can be measured to further characterize the secretome: thermal melting, thermal aggregation, Delta G, and/or viscosity. In some embodiments, a thermal melting assay is employed to determine MSC secretome stability. In some embodiments, a thermal aggregation assay is employed to determine MSC secretome stability. In some embodiments, delta G is employed as a measure for determining MSC secretome stability. In some embodiments, viscosity is measured as an MSC secretome characteristic. In some embodiments, viscosity is to determine MSC secretome stability In some embodiments, biophysical metrics can be employed to establish stability parameters for characterizing different MSC secretome formulations.

In some embodiments, the MSC secretome is stable at 4° C., room temperature (20° C.), and 37° C. for at least 7 days. In some embodiments, the MSC secretome is stable for at least 7 days, at least 1 week, at least 2 weeks, at least 3 weeks, or at least 1 month. In some embodiments, the MSC secretome is stable for at least 7 days, at least 1 week, at least 2 weeks, at least 3 weeks, at least 1 month, at least 2 months, or at least 3 months at about 4° C. In some embodiments, the MSC secretome is stable for at least 7 days, at least 1 week, at least 2 weeks, at least 3 weeks, or at least 1 month at about 20° C. In some embodiments, the MSC secretome is stable for at least 7 days, at least 1 week, at least 2 weeks, at least 3 weeks, or at least 1 month at about 37° C.

Bioassays

In some embodiments, bioassays can be employed to characterize the MSC secretome. In some embodiments, bioassays can be related to corneal wound healing: epithelial cell migration and proliferation, stromal cell differentiation (e.g., scarring); neovascularization, and inflammation. In some embodiments, bioassays can be employed to evaluate the ability of the MSC secretome to mediate corneal wound healing: epithelial cell migration and proliferation, stromal cell differentiation (scarring); neovascularization; and inflammation.

Migration and Proliferation:

In some embodiments, the MSC secretome can be evaluated for the ability of the MSC secretome to promote proliferation and migration. In some embodiments, the MSC secretome can be evaluated for the ability of the MSC secretome to promote proliferation. In some embodiments, the MSC secretome can be evaluated for the ability of the MSC secretome to promote migration. In some embodiments, the MSC secretome promotes proliferation and/or migration. In some embodiments, the MSC secretome promotes proliferation. In some embodiments, the MSC secretome promotes migration. In some embodiments, the MSC secretome can be evaluated use a transwell migration assay to determined proliferation promoting ability.

In some embodiments, a migration assay can be employed to evaluate for the ability of the MSC secretome to promote migration. In some embodiments, the migration assay can include a "scratch assay" (also referred to as a "scratch wound assay"). In some embodiments, the MSC secretome promotes migration and this promotion of migration is determined and/or examined utilizing a "scratch assay". Generally, a scratch assay method is based on when artificial gap, also referred to as a "scratch", occurs on a confluent cell monolayer. The "scratch" can be monitored for the cells on the edge of the newly created gap migrating toward the opening to close/cover the "scratch". See, for example, Liang, C., Park, A. & Guan, J. In vitro scratch assay: a convenient and inexpensive method for analysis of cell migration in vitro. Nat Protoc 2, 329-333 (2007).)

In some embodiments, the migration assay can include a transwell migration assay employing corneal epithelial cells (or other cell surrogate once validation)—(e.g., wound closure) can be performed on the MSC secretome. In some embodiments, a transwell migration assay employing corneal epithelial as a test for wound closure potency of the MSC secretome. In some embodiments, the MSC secretome promotes wound closure as determined using a transwell migration assay.

In some embodiments, human corneal epithelial cell proliferation assays can be performed on the MSC secretome. In some embodiments, human corneal epithelial cell proliferation assays are indicative of a test for wound closure properties of the MSC secretome. In some embodiments, the MSC secretome promotes wound closure as determined using a human corneal epithelial cell proliferation assay.

In some embodiments, an endothelial cell tube formation assay can be performed on the MSC secretome. In some embodiments, an endothelial cell tube formation assays can be indicative that the MSC secretome is not pro-angiogenic. In some embodiments, an endothelial cell tube formation assay provides a measure of the angiogenic potential of the MSC secretome. In some embodiments, the MSC secretome exhibits anti-angiogenic properties. In some embodiments, the MSC secretome is anti-angiogenic properties. In some embodiments, an endothelial cell tube formation assay provides the ratio of anti-angiogenesis signals and pro-angiogenesis signals. In some embodiments, an endothelial cell tube formation assay a negative result will confirm the anti:pro ratio is high and will ensure the MSC secretome will not promote neovascularization. In some embodiments, an endothelial cell tube formation assay a negative result will confirm the anti:pro ratio is high and will ensure the MSC secretome will not promote CNV (choroidal neovascularization) or neovascularization in general. In some embodiments, an inhibition of TGFb induced myofibroblast differentiation assay can be performed on the MSC secretome. In some embodiments, an inhibition of TGFb induced myofibroblast differentiation assay can be performed on the MSC secretome to show that the MSC secretome prevents scarring. In some embodiments, the MSC secretome prevents scarring. In some embodiments, the MSC secretome prevents scarring corneal opacity. In some embodiments, the MSC secretome has low angiogenesis induction. In some embodiments, the MSC secretome has reduced angiogenic response. In some embodiments, the MSC secretome has reduced angiogenic capacity. In some embodiments, the MSC secretome impairs and/or reduces the normal formation of blood vessels in presence of media supportive of angiogenesis. In some embodiments, the MSC secretome has reduced angiogenic capacity when the MSC secretome is compared to untreated control. In some embodiments, the MSC secretome has reduced angiogenic capacity as compared to a sample treated to serum containing media. In some embodiments, the MSC secretome attenuates an angiogenic response. In some embodiments, the MSC secretome reduces the angiogenic response induce by serum free media. In some embodiments, a reduction in angiogenic response is induced by the MSC secretome when secretome plus serum containing media (reduced or no angiogenic response) is compared to serum containing media (angiogenic response). In some embodiments, an angiogenic response is indicated by tube formation in a cell based assay. In some embodiments, an angiogenic response is indicated by tube formation in an endothelial cell tube formation assay.

Differentiation/Scarring:

In some embodiments, the MSC secretome can be evaluated for the ability to prevent differentiation and prevent scarring. In some embodiments, the MSC secretome prevents and/or impairs scarring. In some embodiments, the MSC secretome prevents scarring. In some embodiments, the MSC secretome reduces scarring as compared to other standard treatments. In some embodiments, the MSC secretome prevents and/or impairs differentiation. In some embodiments, the MSC secretome prevents and/or impairs myofibroblast differentiation. In some embodiments, the MSC secretome reduces the loss of corneal transparency. In some embodiments, the MSC secretome reduces the loss of corneal transparency by preventing and/or impairing myofibroblast differentiation.

In some embodiments, the MSC secretome can be evaluated for the ability of the MSC secretome to modulate factors involved in differentiation. In some embodiments, the MSC secretome can be evaluated the ability of the MSC secretome to modulate factors involved in differentiation, including but not limited to TGFB2, Collagen I, Collagen III (normally upregulated during differentiation), TFGB3, MMP-2, and MMP-9 (normally downregulated during differentiation. In some embodiments, the MSC secretome modulates factors selected from the group consisting of TGFB2, Collagen I, Collagen III (normally upregulated during differentiation), TFGB3, MMP-2, and MMP-9 (normally downregulated during differentiation. In some embodiments, the MSC secretome induces a decrease in factors upregulated during normal differentiation. In some embodiments, the MSC secretome induces an increase in factors downregulated during normal differentiation. In some embodiments, the MSC secretome induces a decrease in expression of factors such as SMA. In some embodiments, the MSC secretome induces a decrease in expression of factors such as SMA which is indicative of MSC secretome potency.

Neovascularization:

In some embodiments, the MSC secretome can be evaluated for the ability to prevent neovascularization. In some embodiments, the MSC secretome prevents, impairs, inhibits, and/or reduces neovascularization. In some embodiments, the MSC secretome inhibits neovascularization. In some embodiments, the MSC secretome can be evaluated for the ability to prevent angiogenesis. In some embodiments, the MSC secretome prevents, impairs, inhibits, and/or reduces angiogenesis. In some embodiments, the MSC secretome inhibits angiogenesis.

In some embodiments, the MSC secretome can be further evaluated using depletion assays. In some embodiments, the MSC secretome can be depleted of specified factors. In some embodiments, the MSC secretome can be depleted of specified factors, including for example, but not limited to TIMP1 and/or Serpin E1. In some embodiments, the MSC secretome can be depleted of TIMP1 and/or Serpin E1. In some embodiments, the MSC secretome can be depleted of TIMP1. In some embodiments, the MSC secretome can be depleted of Serpin E1.

Inflammation:

In some embodiments, the MSC secretome can be evaluated for the ability to prevent, impair, inhibit, and/or reduce inflammation. In some embodiments, the MSC secretome prevents, impairs, inhibits, and/or reduces inflammation. In some embodiments, the MSC secretome inhibits inflammation. In some embodiments, the MSC secretome is characterized in vitro and/or in vivo to determine the ability to prevent, impair, inhibit, and/or reduce inflammation. In some embodiments, the MSC secretome prevents, impairs, inhibits, and/or reduces inflammation in vitro and/or in vivo. In some embodiments, the MSC secretome prevents, impairs, inhibits, and/or reduces inflammation in vitro. In some embodiments, the MSC secretome prevents, impairs, inhibits, and/or reduces inflammation or in vivo. In some embodiments, a tissue model can be employed to characterizing preventing, impairing, inhibiting, and/or reducing inflammation in vitro. In some embodiments, a 3D tissue model can be employed to characterizing preventing, impairing, inhibiting, and/or reducing inflammation in vitro. In some embodiments, a nitrogen mustard (NM) gas burn model can be used to evaluate preventing, impairing, inhibiting, and/or reducing inflammation in vitro. In some embodiments, a nitrogen mustard (NM) gas burn model can be used to evaluate preventing, impairing, inhibiting, and/or reducing inflammation in vitro and as a surrogate for in vivo conditions. In some embodiments, the cytokine profile in response to treatment with and/or administration of the MSC secretome can be determined. In some embodiments, the levels of specific cytokines can be determined. In some embodiments, the level of IL-8 can be determined. In some embodiments, the level of IL-8 expression can be reduced in tissues treated with the MSC secretome. In some embodiments, the level of IL-8 expression is reduced in tissues treated with the MSC secretome and this is indicative of preventing, impairing, inhibiting, and/or reducing inflammation.

E. Methods of Treatment

The present disclosure also provides methods of treatment using the MSC secretome of the present disclosure. In particular, the MSC secretome finds use in the treatment of ocular conditions. In particular, the MSC secretome finds use in the treatment of ocular conditions, including but not limited to ocular diseases. In some embodiments, the ocular disease is associated with the ocular surface. In some embodiments, the ocular disease is associated with damaged ocular tissue and/or damaged ocular tissue indications. In some embodiments, the MSC secretome finds use in the treatment of ocular conditions, including accelerating wound healing. In some embodiments, the MSC secretome finds use in the treatment of ocular conditions, including reducing scarring. In some embodiments, the MSC secretome finds use in the treatment of ocular conditions, including reducing inflammation. In some embodiments, the MSC secretome finds use in the treatment of ocular conditions, including reducing inflammation and thus promoting growth. In some embodiments, the MSC secretome finds use in treating ocular conditions such as reducing inflammation at the ocular surface. In some embodiments, the MSC secretome finds use in the treatment of ocular conditions, including reducing neovascularization. In some embodiments, the MSC secretome finds use in the treatment of ocular conditions, including reducing neovascularization in the cornea. In some embodiments, the MSC secretome finds use in the treatment of ocular conditions, including dry eye treatment (including, for example, treatment of severe dry eye, including where the epithelial cells are damaged). In some embodiments, the MSC secretome finds use in the treatment of ocular conditions, such as restoring the integrity to damaged ocular tissue. In some embodiments, the MSC secretome finds use in the treatment of ocular conditions, such as accelerating the healing of damaged ocular tissue. In some embodiments, the MSC secretome finds use in the treatment of ocular conditions, such as regenerating damaged ocular nerve tissue. In some embodiments, the MSC secretome finds use in the treatment of ocular conditions, such as regenerating damaged ocular nerve tissue associated with PCED. In some embodiments, the MSC secretome finds use in the treatment of ocular conditions, such as PCED. In some embodiments, the MSC secretome finds use in the treatment of ocular conditions, such as inflammatory damage to the eye surface. In some embodiments, the MSC secretome finds use in the treatment of ocular conditions, such as for example GvHD and/or Sjogrens syndrome.

In some embodiments, the MSC secretome finds use in accelerating wound healing. In some embodiments, the MSC secretome finds use in reducing scarring. In some embodiments, the MSC secretome finds use in reducing inflammation. In some embodiments, the MSC secretome finds use in reducing inflammation and thus promoting growth. In some embodiments, the MSC secretome finds use in reducing inflammation at the ocular surface. In some embodiments, the MSC secretome finds use in reducing neovascularization. In some embodiments, the MSC secretome finds use in reducing neovascularization in the cornea. In some embodiments, the MSC secretome finds use in the protection and repair of retinal epithelial cells and retinal ganglion cells. In some embodiments, the MSC secretome finds use in induction of trabecular meshwork regeneration and reduction of intraocular pressure.

In some embodiments, the mesenchymal stem cell secretome is administered for the treatment of an ocular disease. In some embodiments, treatment comprises administering to a patient in need thereof therapeutically effective amount of a mesenchymal stem cell secretome composition as described herein to a patient in need thereof. In some embodiments, the mesenchymal stem cell secretome is administered to a patient in need thereof in order to promote or induce ocular wound healing. In some embodiments, the mesenchymal stem cell secretome is administered to a patient in need thereof in order to reduce and/or inhibit neovascularization, reduce and/or inhibit scarring, promote and/or preserve vision, and/or increasing wound closure rate (e.g., decreasing wound closure time). In some embodiments, the mesenchymal stem cell secretome is administered to a patient in need thereof in order to prevent, reduce, and/or inhibit neovascularization. In some embodiments, the mesenchymal stem cell secretome is administered to a patient in need thereof in order to prevent, reduce, and/or inhibit reducing scarring. In some embodiments, the mesenchymal stem cell secretome is administered to a patient in need thereof in order to promote and/or preserve vision. In some embodiments, the mesenchymal stem cell secretome is administered to promote and/or induce closing wound faster wound closure (e.g., reduce the amount of time required for wound closure). In some embodiments, the mesenchymal stem cell secretome prevents, reduces, and/or inhibits neovascularization and reducing scarring in order to promote vision preservation. In some embodiments, the mesenchymal stem cell secretome is administered to a patient in need thereof in order to prevent, reduce, and/or inhibit neovascularization and reducing scarring in order to promote vision preservation. In some embodiments, the mesenchymal stem cell secretome prevents, reduces, and/or inhibits inflammation. In some embodiments, the mesenchymal stem cell secretome is administered to a patient in need thereof in order to prevent, reduce, and/or inhibit inflammation.

In some embodiments, the mesenchymal stem cell secretome is administered for the treatment of a visual dysfunction following traumatic injury to ocular structures. In some embodiments, treatment comprises administering to a patient in need thereof a therapeutically effective amount of a mesenchymal stem cell secretome composition as described herein In some embodiments, the mesenchymal stem cell secretome is administered for the treatment of a traumatic injury of the optic nerve degeneration following concussive injury. In some embodiments, the concussive injury to the eye is selected from the group consisting of ocular contusion and blunt injury to the eye. In some embodiments, the mesenchymal stem cell secretome is administered for the treatment of a traumatic injury of the optic nerve. In some embodiments, treatment comprises administering to a patient in need thereof a therapeutically effective amount of a mesenchymal stem cell secretome composition as described herein.

In some embodiments, the mesenchymal stem cell secretome is administered for ameliorating optic nerve degeneration following concussive injury to the eye. In some embodiments the method for ameliorating optic nerve degeneration comprises administering to the patient a therapeutically effective amount of a mesenchymal stem cell secretome composition as described herein. In some embodiments, the concussive injury to the eye is selected from the group consisting of ocular contusion and blunt injury to the eye. In some embodiments, the concussive injury to the eye an ocular contusion. In some embodiments, the concussive injury to the eye a blunt injury to the eye.

Efficacy readouts can include a reduced in symptoms and/or decreased disease state, including for example, increased quality of life. In some embodiments, reduced in symptoms and/or decreased disease state by 10%, 20%, 30%, 40%, 50%, 60%, 70%, 80%, 90%, 95%, or 100% is indicative of therapeutic efficacy. In some embodiments, reduction in inflammation by 10%, 20%, 30%, 40%, 50%, 60%, 70%, 80%, 90%, 95%, or 100% is indicative of therapeutic efficacy. In some embodiments, a reduction in scarring by 10%, 20%, 30%, 40%, 50%, 60%, 70%, 80%, 90%, 95%, or 100% is indicative of therapeutic efficacy. In some embodiments, a reduction in neovascularization by 10%, 20%, 30%, 40%, 50%, 60%, 70%, 80%, 90%, 95%, or 100% is indicative of therapeutic efficacy.

In some embodiments, the disease or conditions an ocular disease or ocular condition. In some embodiments, the disease or condition is a visual dysfunction following traumatic injury to ocular structures. In some embodiments, the disease or condition is a concussive (e.g., blunt or non-blunt) injury to the eye. In some embodiments, the disease or condition is a burn, including a chemical burn to the eye.

In some embodiments, the mesenchymal stem cell secretome is administered to a particular targeted area. In some embodiments, the particular targeted area is the eye. In some embodiments, the mesenchymal stem cell secretome is administered to a particular targeted area and is formulated so as not to spread to other surrounding areas.

In some embodiments, the mesenchymal stem cell secretome is administered to a particular targeted area and is formulated so as not to spread to other surrounding areas.

In some embodiments, the mesenchymal stem cell secretome is administered to a particular targeted area and is formulated to stay in the targeted area for at least 1 minute, at least about 2 minutes, 3 at least about minutes, at least about 4 minutes, at least about 5 minutes, at least about 10 minutes, at least about 15 minutes, at least about 20 minutes, at least about 30 minutes, at least about 40 minutes, at least about 50 minutes, at least about 60 minutes, at least about 70 minutes, at least about 80 minutes, at least about 90 minutes, or at least about 2 hours.

In some embodiments, the mesenchymal stem cell secretome is administered to an affected area immediately after the wound or injury. In some embodiments, the mesenchymal stem cell secretome is administered to an affected area within 15 seconds, 30 seconds, 1 minutes, 2 minutes, 3 minutes, 4 minutes, 5 minutes, 10 minutes, 15 minutes, 20 minutes, 30 minutes, 40 minutes, 50 minutes, 60 minutes, 70 minutes, 80 minutes, 90 minutes, 2 hours, 4 hours, 8 hours, 12 hours, 24 hours, 36 hours, 48 hours, or 96 hours.

In some embodiments, the mesenchymal stem cell secretome is administered topically. In some embodiments, the mesenchymal stem cell secretome is administered by subconjunctival injection. In some embodiments, the MSC secretome compositions exhibit ultrapotency when administered to a subject in need thereof. In some embodiments, the mesenchymal stem cell secretome is administered topically once, two, three, four, five, and/or up to six times daily. In some embodiments, the MSC secretome compositions allow for therapeutic efficacy with one drop or one administration per day. In some embodiments, one drop is administered 1, 2, 3, 4, 5, or 6 times per day. In some embodiments, one drop is administered at 1 hour, 2 hour, 3 hour, or 4 hour intervals. In some embodiments, one drop is administered at least once per day for 1 week, 2 weeks, 3 weeks, 4 weeks, 5 weeks, 6 weeks, 7 weeks, 8 weeks, 9 weeks, or 10 weeks. In some embodiments, one drop is administered at least twice per day for 1 week, 2 weeks, 3 weeks, 4 weeks, 5 weeks, 6 weeks, 7 weeks, 8 weeks, 9 weeks, or 10 weeks. In some embodiments, one drop is administered at least 3 times per day for 1 week, 2 weeks, 3 weeks, 4 weeks, 5 weeks, 6 weeks, 7 weeks, 8 weeks, 9 weeks, or 10 weeks. In some embodiments, one drop is administered at least 4 times per day for 1 week, 2 weeks, 3 weeks, 4 weeks, 5 weeks, 6 weeks, 7 weeks, 8 weeks, 9 weeks, or 10 weeks. In some embodiments, one drop is administered at least 5 times per day for 1 week, 2 weeks, 3 weeks, 4 weeks, 5 weeks, 6 weeks, 7 weeks, 8 weeks, 9 weeks, or 10 weeks. In some embodiments, one drop is administered at least 6 times per day for 1 week, 2 weeks, 3 weeks, 4 weeks, 5 weeks, 6 weeks, 7 weeks, 8 weeks, 9 weeks, or 10 weeks.

F. Kit

A kit can include an MSC secretome in a container or the conditioned media for use in preparing an MSC secretome, also in a container, as disclosed herein, and instructions for use. Additionally, a kit can include components for mixing to prepare a solution for use in an ocular treatment, and instructions for mixing and use.

The container can include at least one vial, well, test tube, flask, bottle, syringe, or other container means, into which an MSC secretome in a container or the conditioned media for use in preparing an MSC secretome, and in some instances, suitably aliquoted. Where an additional component is provided, the kit can contain additional containers into which this component may be placed. Such containers may include injection or blow-molded plastic containers into which the desired vials are retained. Containers and/or kits can include labeling with instructions for use and/or warnings.

The present disclosure is further illustrated by the following examples, which should not be construed as further limiting. The contents of all figures and all references, Genbank sequences, patents and published patent applications cited throughout this application are expressly incorporated herein by reference.

The present invention can provide kits comprising a panel of tests and/or assays for characterizing a MSC secretome, wherein the panel comprises at least two characterization assays, wherein characterization assays are selected from the group consisting of physical component characterizations, oxidative stress assays, safety analyses, stability assays, proliferation assays, migration assays, neovascularization assays, differentiation/scarring assays, and/or inflammation assays. In some embodiments, the panel of tests and/or assays identifies a MSC secretome as described herein.

The present invention can provide kits comprising a panel of tests and/or assays for determining consistency between MSC secretome lots, wherein the panel comprises one or more characterization assays, wherein characterization assays are selected from the group consisting of physical component characterizations, oxidative stress assays, safety analyses, stability assays, proliferation assays, migration assays, neovascularization assays, differentiation/scarring assays, and/or inflammation assays. In some embodiments, the panel of tests and/or assays identifies a MSC secretome as described herein.

EXAMPLES

Example 1: Secretome Characterization

Biochemical Composition:

The biochemical composition of the MSC secretome can be analyzed for the presence of various factors and activities, including:
- IDO (Indoleamine-2,3-dioxygenase) enzyme activity assay;
- threshold ppm levels for several trophic factors/cytokines including, but not limited to: HGF, FGF-7, TIMP-1, TIMP-2 Thrombospondin, PAI-1 (Serpin E1), VEGF-A, b-NGF; evaluated by ELISA or luminex; and
- additional factors: sFLT-1, PEDF (Serpin F1), IGFBP-2, IGFBP-3, SDF-1, TSG-14, Kallikrein 3, MCP-1, bFGF (FGF2), Angiogenin, MCP-2, Angio-2, IL-6, IL-17, G-CSF, M-CSF, GM-CSF, IL-8, TNF-beta, PDGF.

The biochemical composition of the MSC secretome can be analyzed based on ranges of factors of from about 10-150,000 pg/$10^5$ cells/per day.

Particle counts to quantitate the EVs (extracellular vesicles) in the secretome will also be performed Lipid content can be evaluated as needed.

Biophysical Characterization/Release can be performed, including 1) FTIR spectroscopy; 2) Buffer Exchange/Concentrating Secretome Process (the buffer exchange process is used to concentrate secretome as well as in some instances being a size exclusion process where any molecules below a pre-defined molecular weight cut-off can be removed. For example, VEGF is a very small protein (42 kDa) so can potentially remove almost all (or effectively all) of VEGF based the filtration cut-off employed.

Once purified and concentrated, the MSC secretome can then be subjected to further downstream processing. Such downstream processing will include buffer exchange processes to prepare the MSC secretome for administration. The buffer exchange can employ hollow fiber tangential flow method in order to remove the media components and replace them with the desired formulation components. The buffer exchange processing step can also result in concentration of the secretome as well.

The secretome can then be formulated for administration.

Example 2: Biopotency and Biophysical Characterization of a Secretome

The present example describes methods for determining the secretome identity, as well as composition analyses, biochemical and biophysical characterization, and cell-based assays for use in secretome characterization.

The analytical techniques described in this example can be used to evaluate performance and stability of different formulations. The formulation with the best stability and tolerance profile will undergo dose-response and dosing regimen evaluation using the alkaline rodent burn injury model. Time to wound healing and histopathology at the wound site, as well as local toxicity can be evaluated.

Potency Assays:

In order to determine the properties of the conditioned media, various potency assays can be performed, including the following:

A transwell migration assay corneal epithelial cells (or other cell surrogate once validation)—(e.g., wound closure) can be performed. This assay will provide a metric of the trophic growth factors present in secretome (e.g., HGF, FGFs).

A human corneal epithelial cell proliferation assays (e.g., wound closure). This assay will provide a metric of the trophic growth factors present in secretome (e.g., HGF, FGFs).

An endothelial cell tube formation assay, which can be a characterization assay to show that the lot is not pro-angiogenic, can be performed. This assay will provide a measure of the angiogenic potential of the secretome product—it must be inhibitory (e.g., exhibit anti-angiogenic properties). This assay will allow for testing for reduced angiogenic capacity. In assay, angiogenic response or angiogenic capacity is reduced relative to untreated. For example, the experiments will have two sample groups: 1) untreated with secretome but with serum containing media (which induces tube formation aka the normal angiogenic response) and 2) treated with secretome and serum containing media. The secretome attenuates this normal angiogenic response and as such exhibits reduced angiogenic potential. See, for example, FIGS. 5-6. This assay will reflect the ratio of anti-angiogenesis signals and pro-angiogenesis signals. A negative result will confirm the anti:pro ratio is high and will ensure the secretome product will not promote CNV (choroidal neovascularization) or neovascularization in general. For example, for evaluating the neovascularization modulating ability the MSC secretome, other assays to evaluate expression level and activity of a few factors (as revealed through depletion studies described herein) will also be employed. An inhibition of TGFb induced myofibroblast differentiation assay (e.g., anti-scarring) can be performed. This assay will evaluate the ability of secretome to prevent scarring (or corneal opacity); to be evaluated by qPCR, fluorescence microscopy, and western blot are factors characteristic of differentiation of stromal fibroblasts into myofibroblasts (e.g., smooth muscle actin) and matrix deposition.

Oxidative stress prevention assays can be performed. A 3D model assay may also be used to evaluate potency and to prevent/repair nitrogen mustard gas damage to the corneal epithelium, as a readout. For such an assay, macroscopic observations would be examined to ensure tissue health as well as assaying for various anti-inflammation markers (such as, for example, IL-8).

The FDA Guidance has provided industry Guidance for cellular and gene products. (See, the World Wide Web at fda.gov/downloads/biologicsbloodvaccines/guidancecompliance regulatoryinformation/guidances/cellularand-genetherapy/ucm243392.pdf; incorporated herein by reference). This guidance provides for performing potency assays and testing, and how such potency assays correlated to therapeutic efficacy of the MSC secretome can be evaluated for potency under the standard FDA guidelines.

Safety Characterization

Secretomes can be evaluated for blood compatibility and implementing tests for sterility as well as pyrogen and endotoxin levels. Generally, the current recent FDA guidance can be employed for such analytical analyses (e.g., 2012 FDA Guidance: Pyrogen and Endotoxin testing). (See, the fda.gov/downloads/Drugs/GuidanceComplianceRegulatoryInformation/Guidances/UCM31 0098.pdf, incorporated herein by reference).

Methods for evaluating blood compatibility that comprise assays for hemolysis and hemagglutination will also be employed to confirm no systemic exposure issues with the MSC secretome prepared, in the event systemic exposure occurs for example with severe ocular burns. These methods build on existing techniques (Maji et al.; Saswati et al.; Nayak et al.) and use blood from healthy consenting donors. Briefly, for hemolysis, red blood cells (RBCs) can be co-incubated with the MSC secretome at 37° C. for 1 hour. RBCs treated with ostonic PBS will serve as a negative control and distilled water will serve as a positive control. After incubation and centrifugation, the absorbance at 540 nm (Amax for hemoglobin) can be measured. % hemolysis can be calculated as: $100\% \times (A_{MSC-S} - A_{blank})/A_{distilled\ water}$. This study will allow for establishment of a dose that begins to induce hemolysis and make an assessment if the MSC secretome is hemocompatible in accordance with ISO/TR 7406 (hemolytic ratio <5%). For hemagglutination, an RBC suspension can be co-incubated for 2 hr at 37 C with the MSC secretome in 96 well U-bottom dish. A positive result for hemagglutination is an RBC suspension (as an agglutinated RBC lattice doesn't fall out of solution), whereas a negative result an RBC 'button' at the bottom of the well resulting from RBCs settled out of solution. The MSC secretome will not demonstrate hemagglutination activity.

Sterility and endotoxin methods for analysis will also be developed. These methods can be useful to perform sterility and endotoxin testing for each MSC secretome produced. These assays can be employed to demonstrate the test is capable of reliably detecting the presence of viable contaminating microorganisms or contaminating endotoxin. All test components can also be verified to demonstrate the test method can consistently detect the presence viable microorganisms or endotoxin.

Biochemical and Biophysical Characterization

The MSC secretome is a complex combination of components and therefore it is beneficial to characterize the secretome components in order to develop the most relevant and meaningful potency assays. A diverse combination of characterization techniques, including molecular, biochemical, and biophysical analyses can be used to measure potency.

Such characterization studies will focus on: 1) a comprehensive (and quantitative) mapping of the molecular entities in the MSC secretome; 2) measuring the contributions of select factors to biological activity; and 3) measuring biophysical parameters. Importantly, each of the focus areas can be applied to each preparation of the MSC secretome to evaluate preparation consistency.

This example describes the characterization of the molecular makeup the MSC secretome. The MSC secretome is composed of protein factors as well as extracellular vesicles (EVs), therefore necessitating the need to characterize both fractions. A combination of bioanalytical techniques (including protein arrays, enzyme-linked immunosorbent assays (ELISAs), mass spectrometry, and immunoblotting), can be used to characterization these molecules in the MSC secretome. Protein arrays and mass spectrometry has been employed to determine the presence of factors and to identify the factors. More quantitative techniques such as ELISA can be used to measure the levels of each factor present and establish ranges for several analytes.

Several factors for the MSC secretome have been identified, including trophic factors as well as properties such as overall low angiogenesis induction. Factors identified for the MSC secretome to date include: Pentraxin-3, TIMP-1, Serpin E1, TSP-1, HGF.

In addition to trophic and other factors, EVs are a prominent component of secretomes, and themselves have been the focus of therapeutic campaigns. To evaluate the EV component of our API, a series of analyses can be performed. First, a simple lipid content analysis can be performed using a lipid-binding dye (such as Nile Red) to generate quantitative measurement for total lipid in product lots. Additionally, evaluation of particle number and size distribution using a NanoSight NS300 can be done. This analysis can be performed on each lot to establish ranges for particles concentration and consistent particle distribution size. Biochemical characterization of the EV fraction using immunoblotting for standard markers (including AUX, TSG101, CD63, CD9, and CD81) can be performed.

To complement our biochemical analyses, depletion studies can be performed to distill the individual contributions of critical factors. Briefly, using an antibody-based pulldown method, defined factors can be removed from the MSC secretome. Depletion can be verified by western blot and then evaluated in a series of bioassays (described below). Similar studies can be performed to evaluate the contributions of the protein fraction and the EV fraction.

The biophysical characteristics of the MSC secretome can also be evaluated with a platform that uses fluorescence, static light scattering and dynamic light scatting to characterize protein stability metrics. The following parameters can be measured:

Thermal melting: Measures the intrinsic fluorescence of exposed tryptophan or tyrosine residues proteins undergo conformational changes. The assay measures a change in fluorescence intensity or a peak shift as proteins begin to unfold. Enables rank-ordering and comparison of different formulations.

Thermal melting with SYPRO: Uses Differential scanning fluorimetry (DSF). Measures the spectral shift of a dye (SYPRO Orange, Molecular Probes, Inc.) when it binds to exposed hydrophobic residues as proteins unfold. Sensitivity of fluorescence enables measurement at very low concentrations of MSC secretome.

Thermal aggregation: Monitors the aggregation behavior and temperature at which API aggregates during a thermal ramp. Uses SLS to measure at two wavelengths (266 nm and 463 nm) to differentiate small and large particles. Enables rank-ordering and comparison of different formulations and informs on the dynamic of protein unfolding and aggregation.

Delta G: measures the change in fluorescence of API after addition of a chemical denaturant. Enables calculation of a quantitative value for protein stability, or the amount of energy required to unfold the MSC secretome, delta G Viscosity: measures viscosity of MSC secretome formulations using small amounts of material. Enables evaluation and comparison on different formulations The above biophysical metrics will establish key stability parameters for evaluating different MSC secretome formulations and performing extended/and or accelerated stability studies for the MSC secretome. Stability analyses on the MSC secretome formulated at two different pH 6.4 and 7.4 have been performed.

Biopotency

Rationale:

Development of a cell-based assay program for evaluating potency of the MSC secretome has begun. The cell-based assay program will aim achieve the following:

Demonstrate product activity, quality and consistency throughout product development Generate a collection of data to support specifications for lot release Provide a basis for assessing manufacturing changes Evaluate the MSC secretome stability To appropriately evaluated the MSC secretome, a suite of bioassays can be developed to evaluate the MSC secretome bio-potency, as described in the Examples provided herein.

Bioassays

To develop the suite of bioassays for the MSC secretome, the focus can be on processes which include the major events that co-ordinate corneal wound healing: epithelial cell migration and proliferation, stromal cell differentiation (scarring); neovascularization; and inflammation. Bioassays to evaluate the MSC secretome's ability to mediate each of these processes can be employed.

Migration and Proliferation:

Following trauma, corneal epithelial cells must divide and migrate at the leading edge of the wound to mediate closure (Ljubimov A V., Prog Retin Eye Res. 2015 November; 49:17-45.). Primary corneal epithelial cells (or alternatively immortalized corneal epithelial cells) and in vitro cell assays to evaluate the ability of the MSC secretome to promote proliferation and migration.

For proliferation, corneal epithelial cells can be cultured in the presence of MSC-S at defined doses. Live cell stains (e.g., MTT or WST-8) to quantitate viable cells after defined incubation periods (e.g., 24 hr and 48 hr). For migration, transwell migration assay can be employed, in which corneal epithelial cells can be seeded into chambers with an 8 micron polycarbonate membrane in basal media minus growth factors. The chamber can be placed into a culture dish well (24 well dishes) contained basal media supplemented with our API at defined doses. After 24 hour incubation the cells that have migrated through the membrane can be quantitated using either fluorescent (e.g., Calcein AM) or colorimetric (e.g., crystal violet) stains.

Differentiation/Scarring:

After an ocular trauma that breaches the stromal layer of the cornea (the layer beneath the epithelium), corneal fibroblasts are triggered to differentiate into smooth muscle actin (SMA)-expressing myofibroblasts in a process mediated by transforming growth factor-$\beta$ (TGF$\beta$). While this process accompanies the normal wound healing process, it carries an undesirable outcome for the eye: scarring and vision impairment. This vision impairment comes about from myofibroblasts deposing large quantities of disorganized extracellular matrix which leading to a loss of corneal transparency. An assay has been developed to evaluate the ability of the MSC secretome to prevent or impair myofibroblast differentiation, and hence is also a potency measure of the MSC secretome.

Human corneal fibroblasts can be used a model cell system. Cells can be treated with TGFB1 to induce differentiation in presence (or absence) of increasing concentrations of API and allowed to incubate for a further 24 hr. Fibroblasts treated with TGFB1 rapidly differentiate to myofibroblasts, characterized by markedly increased expression level of smooth muscle actin, as well as modulation of several other factors: TGFB2, Collagen I, Collagen III (normally upregulated during differentiation) and TFGB3, MMP-2, and MMP-9 (normally downregulated during differentiation). qPCR and immunoblotting (for mRNA and protein, respectively) can be employed to measure the effects of the MSC secretome on expression levels of these molecular hallmarks of differentiation. The MSC secretome treatment will decrease the expression of factors such as SMA, which can be a reflective measure of its potency.

Neovascularization:

Healthy corneas are avascular and devoid of blood vessels. However, after trauma, corneal neovascularization often occurs, which contributes to vision impairment and even vision loss. More specifically, neovascularization may induce tissue scarring, lipid deposition, stromal hemorrhage, and corneal edema, severely altering visual acuity. A critical feature of the MSC secretome is its ability to impair neovascularization during the healing process. A cell-based assay can be implemented to evaluate the MSC secretome's ability to impair angiogenesis.

An endothelial tube formation assay can be implemented using human umbilical vein endothelial cells (HUVEC). This assay is a standard assay for evaluating blood vessel development by measuring the endothelial cell reorganization to form capillary-like vascular structures. Briefly, HUVEC cells are seeded on thin layer of basement membrane extract (collagen or Matrigel®; BD Biosciences), and incubated in the presence or absence of API. Within 2-6 hr, endothelial cells will divide and begin to form a vascular network if supported by pro-angiogenic molecules. It can be evaluated whether the MSC secretome is able to impair the formation of this network. Images can be acquired and image analysis software can be used to measure the following parameters: branch points, tube lengths and numbers, loop numbers and areas, cell covered area. The MSC secretome can inhibit angiogenesis.

To supplement the tube formation assay, it can be helpful to perform depletion studies, in which specified factors (e.g., TIMP1, Serpin E1) are removed or depleted from the API and evaluate the impact in the assay. A goal in performing these assays can be to determine the critical anti-angiogenic molecules in MSC-S (of which there are many), which can assist in developing release criteria.

Inflammation:

Several animal models (Yamagami S., et al., *Invest Ophthalmol Vis Sci.* 2005 April; 46(4): 1201-7; Gao, N., et al., *Am J Pathol.* 2011 November; 179(5):2243-53; and Jin, Y., et al., *Mol Vis.* 2007 Apr. 27; 13:626-34.) have shown that corneal epithelial wounding prompts an acute inflammatory response in the limbal blood vessels leading to accumulation of leukocytes and neutrophils and migration of dendritic cells, macrophages and lymphocytes into the stroma and the wounded epithelium. This increased immune infiltration of the cornea leads to neovascularization, which may result in visual loss. Indeed, the clinicians on our scientific advisory board have emphasized the importance of dampening the inflammatory response in the acute stage of corneal injury. To characterize this critical capacity of the MSC secretome and develop a bioassay for the process in vitro cells assays as well as in vitro tissue assays can be developed and employed.

To develop an in vitro cell assay, the ability of lipopolysaccharide (LPS) to trigger an inflammatory response can be utilized. LPS is a component of the cell membrane in Gram-negative bacteria and is a potent trigger for secretion of various cytokines produced by inflammatory cells. Injection of LPS into the corneal stroma induces rapid infiltration of inflammatory cells including neutrophils and monocytic cells into the stroma and leads to corneal ulceration in rabbits. Specifically, stromal fibroblasts recognize the presence of LPS and trigger inflammatory cell infiltration through expression of chemokines and adhesion molecules (e.g., IL-8 and MCP-1) (Fukuda K., Int J Mol Sci. 2017 Aug. 23; 18(9).). Primary human corneal fibroblasts can be treated with LPS in presence or absence of the MSC secretome. Cells can be incubated for 24 hr prior to assessment, during which the levels of IL-8 and MCP-1 (immune cell chemoattractants) can be measured, in the culture media. ELISA can be used as a quantitative technique to measure the cytokine levels. Treatment with the MSC secretome will decrease the levels of IL-8 and MCP-1 in the media.

Second, a 3D tissue model can be used model is an in vitro reconstructed human corneal tissue model that structurally and functionally reproduces key features of in vivo corneal tissue. Importantly, the model behaves like native corneal tissue and replicates the inflammatory response to chemical burn (e.g., Nitrogen Mustard). The model for nitrogen mustard (NM) gas burns can be implemented and can be used to evaluate the ability of the MSC secretome to dampen the immune response. This model is generally employed to mimic the in vivo conditions for evaluating the inflammatory response. Similar to the in vitro model, the cytokine profile (e.g., levels of IL-8) in response to treatment with the MSC secretome after NM burn can be evaluated. The levels IL-8 can be reduced in tissues treated with the MSC secretome.

Example 3: MSC Secretome Characterization and Properties

MSC-S is Comprised of Key Factors Associated with Wound Healing.

Figure 2:
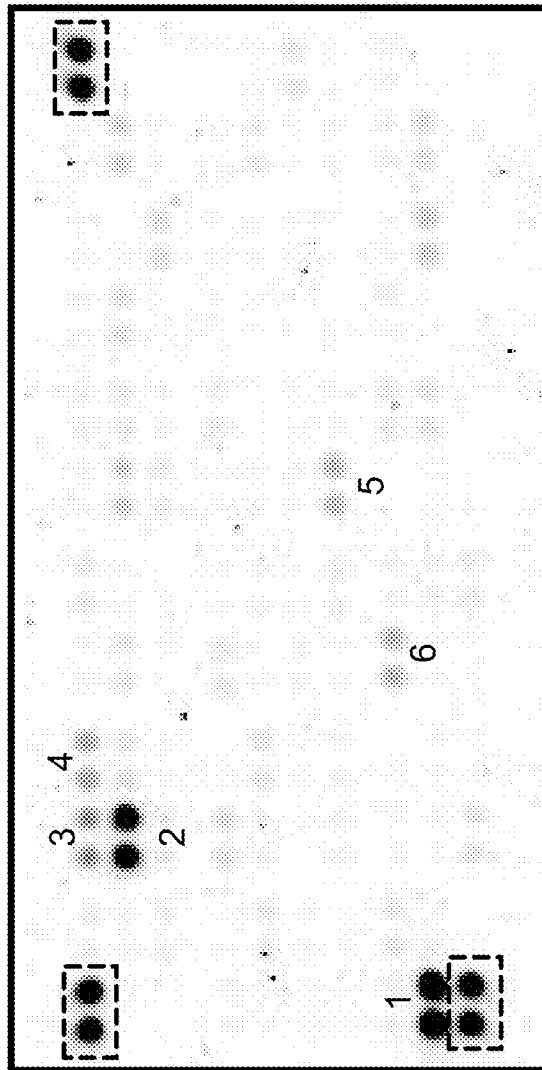
FIG. 2. MSC-S contains wound healing factors. A Human XL Cytokine Array (R&D Systems) was used to identify several protein factors present in MSC-S. Dashed boxes: reference spots.

Prominent factors associated with wound healing and repair make up MSC-S. Biochemical characterization of MSC-S has been performed using a human growth factor/cytokine array containing 105 different proteins (FIG. 2) and most of the highly represented proteins are involved in promoting wound healing or modulating important processes for tissues repair (e.g., reducing oxidative stress).

MSC-S Exhibits a Low Propensity for Aggregation.

MSC-S was analyzed to evaluate stability and aggregation propensity. In this study, MSC-S was prepared in phosphate buffers at pH 6.4 and 7.4. MSC-S was first characterized by size exclusion chromatography (SEC) by storage of the MSC-S at 4° C., room temperature (20° C.), and 37° C. for 7 days and then re-evaluated those sample by SEC. Only a slight increase in one SEC peak (RT 8.5 min) that correlates with increasing temperature and is reflective of a slight increase in aggregated material over time was observed.

Figures 3A, 3B, 3C:
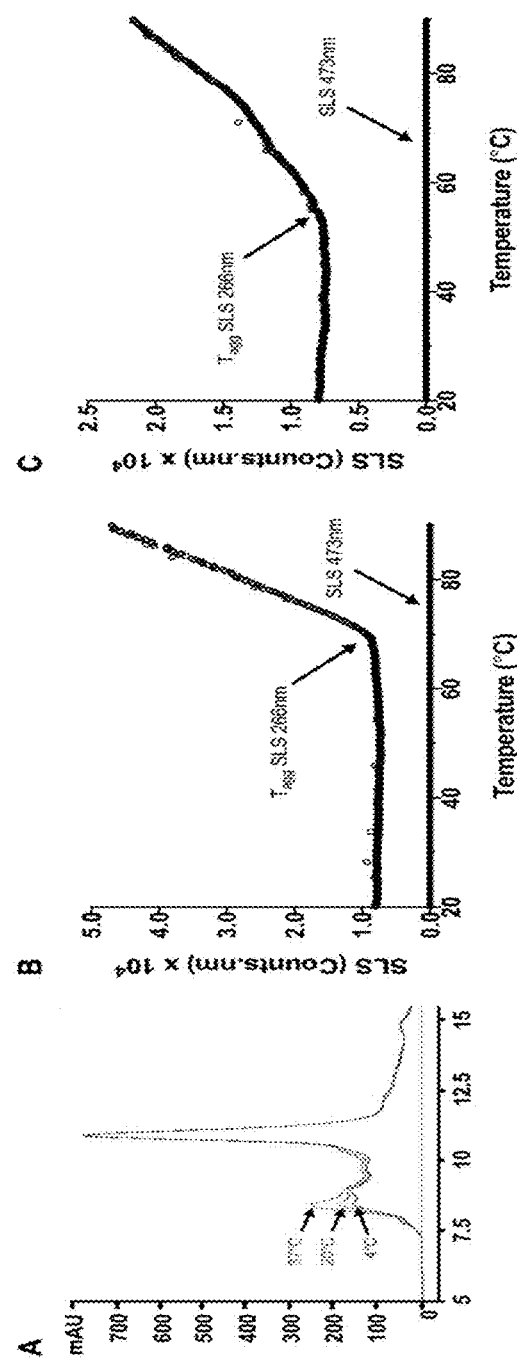
FIG. 3A-FIG. 3C. MSC-S demonstrates a low propensity for aggregation. A) MSC-S formulated in phosphate buffer at pH 7.4 was analyzed by SEC. After initial thaw, MSC-S was maintained at 4° C., 20° C., or 37° C. for seven days and analyzed by SEC. Only a small increase in higher order aggregates is observed and correlates with higher storage temperature. Sample were resolved on an Agilent 1100 HPLC system equipped with a diode array detector and TSKgel SuperSW 2000, 4.6×300 mm column using a flow rate of 0.25 mg/mL and mobile phase of 1×PBS. Wavelength monitored was 214 nm. 28 ug MSC-S was loaded. B) MSC-S formulated at pH 7.4 is more stable than C) pH 6.4 by thermal aggregation propensity. Samples were evaluated and monitored signal at 266 nm and 473 nm (for large aggregates). 8.8 uL of 1 mg/mL MSC-S was loaded in 4 replicates into Uni cuvettes. A temperature scan was performed from 20° C. to 90° C. at 0.6° C. per minute scan rate.

To further analyze the aggregation propensity, a static light scattering (SLS) thermal aggregation analysis was performed (FIG. 3). This assay measures SLS at 266 nm and 473 nm; SLS266 measurements are more sensitive to changes in sample intensity and inform on the onset of small particle formation, whereas SLS473 measurements are useful to detect larger aggregates. The temperature for onset of small aggregates ($T_{agg-266}$ nm) was observed to be higher for sample at pH 7.4 (68-70° C.; FIG. 3A) compared to pH 6.4 (54° C.; FIG. 3B). This indicates MSC-S is more stable at pH 7.4 in terms of thermal aggregation propensity. Importantly, no appreciable signal for large aggregates ($SLS_{473\,nm}$) was observed throughout the temperature ramp for both pH values tested (FIG. 3A, 3B), indicating the degree of large aggregate formation is very low.

MSC-S Promotes the Migration of Human Primary Corneal Epithelial Cells.

Figures 4A, 4B:
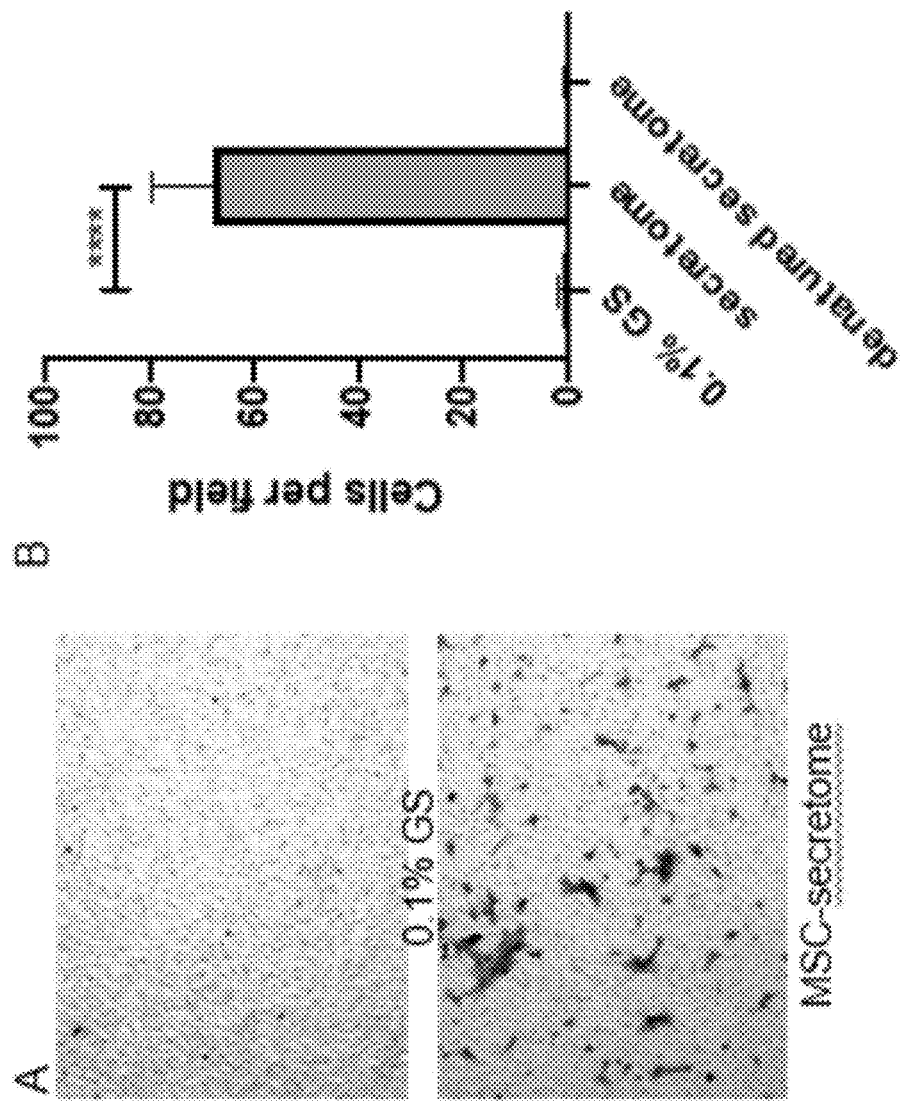
FIG. 4A-FIG. 4B. MSC-S promotes the migration of human primary corneal epithelial cells. A) Pictured are the bottom sides of the transwell membrane after 24 incubation with MSC-S or 0.1% growth supplement. B) MSC-S significantly promotes migration. Migrated cells were enumerated in 3 fields per replicate over 3 replicates per treatment. A two-tailed unpaired t-test was performed using GraphPad Prism version 8.0.0 for Windows, GraphPad Software, San Diego, Calif. USA, (See, the World Wide Web at graphpad- .com). Data presented is mean±SE: ****$p<0.0001$.

The ability of MSC-S (lot 2) was evaluated to promote migration of corneal epithelial cells, which is a critical process for rapid wound closure. A transwell migration assay was implemented that used human primary corneal epithelial cells to measure migration. Cells were seeded in basal media in an upper chamber with a porous membrane bottom. The chamber was then placed in media containing MSC-S. After 24 hr the migrated cells are quantitated. Data showed that MSC-S indeed promotes the migration of epithelial cells (FIG. 4 A, B). Further data showed that heat denaturation (90° C./10 min) abrogates the migration promoting activity of MSC-S (FIG. 4B), establishing the assay as a stability indicating assay.

MSC-S Demonstrates Anti-Angiogenic Properties.

Figures 6A, 6B:
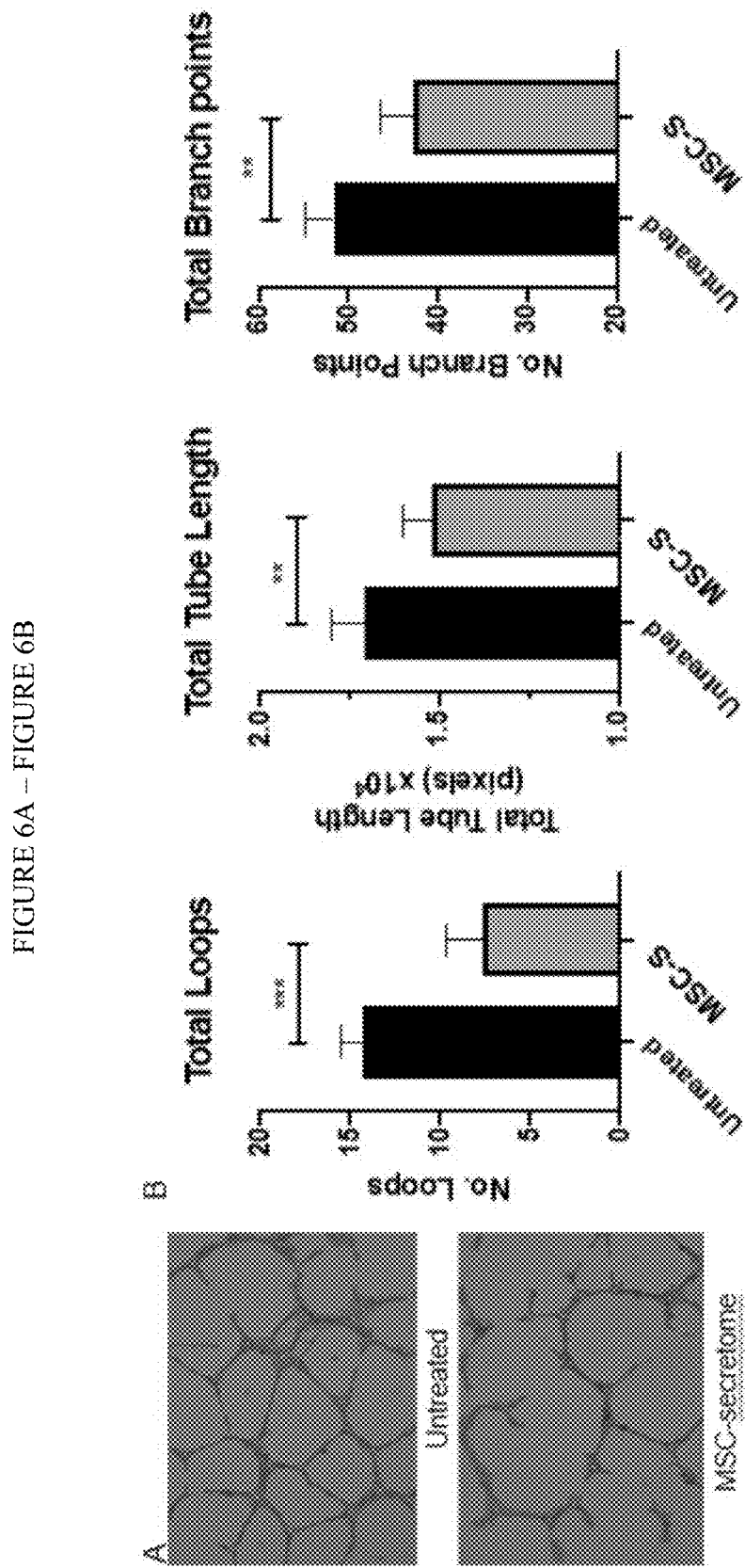
FIG. 6A-FIG. 6B. MSC-S exhibits anti-angiogenic properties in a tube formation assay. HUVEC cells (10K in 100 µL) were seeded onto Matrigel at 10K cells in 100 uL of Endothelial Cell Basal media plus Low Serum Growth Supplement (Life Technologies) and in the absence or presence of MSC-S (300 µg/mL). Cells were incubated for 6 hr to allow endothelial tube formation, followed by image acquisition and processing. Five replicates were performed for each condition. A) Image panels show MSC-S attenuates tube formation. B) MSC-S reduces angiogenesis metrics: total loops, total tube length, and total branch points. Images processed using Wimasis. 2016. WimTube: Tube Formation Assay Image Analysis Solution. Release 4.0. A two-tailed unpaired t-test was performed using GraphPad Prism version 8.0.0 for Windows, GraphPad Software, San Diego, Calif. USA, www.graphpad.com. Data presented is mean SE: $p<0.001$, and *$p<0.0005$.

Characterization of MSC-S has been performed to identify key proteins associated with angiogenesis, as well as evaluate its effect on in vitro endothelial tube formation. The content of MSC-S was analyzed using human angiogenesis protein arrays (R&D Systems) (FIG. 5A). Different production lots have been analyzed and it has been found that the protein composition, both identity and relative quantity, to be consistent. Analysis of the arrays shows the most prominent proteins are classified as anti-angiogenic and are present in 2-7 fold excess of pro-angiogenic molecules (FIG. 5B). Notably, TIMP-1, a matrix-metalloprotease inhibitor, is present at high levels, which is consistent with reports that identify TIMP-1 as the principal anti-angiogenic modulator produced by MSCs (Zanotti, et al., Leukemia. 2016 May; 30(5):1143-54.). The anti-angiogenic biochemical fingerprint translated to a cell-based assay where an inhibition of angiogenic features was observed. Using a HUVEC tube formation assay, it was shown that incubation with MSC-S attenuates tube formation parameters, such as total tube length, number of branch points, and number of loops (FIG. 6). Collectively, the inhibition of these characteristics highlights that MSC-S impairs neovascularization. These anti-angiogenic properties of MSC-S make it well suited as an ophthalmic therapeutic as it has the potential to impair corneal neovascularization during wound healing, thereby decreasing the chances of vision impairment or blindness.

MSC-S Demonstrates Anti-Scarring Properties.

Figure 7A:
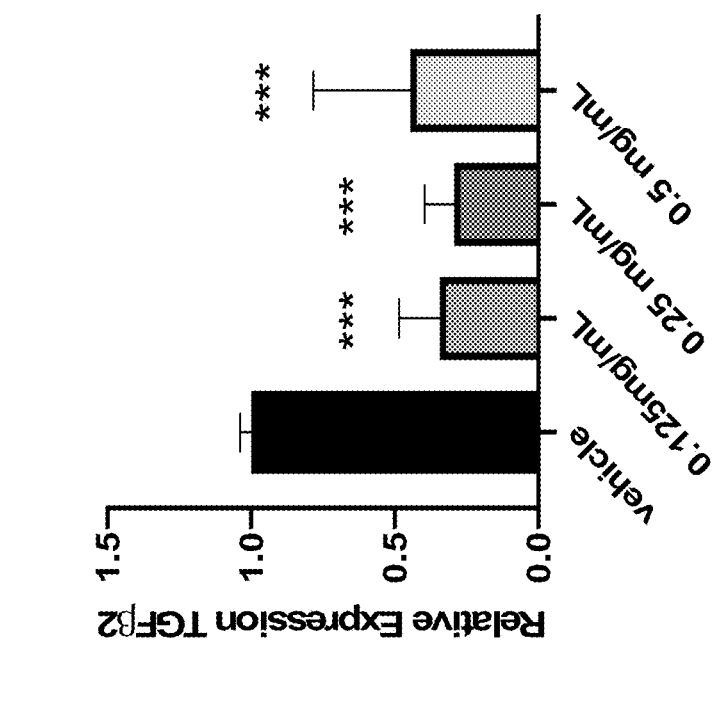
FIG. 7. MSC-S demonstrates anti-scarring properties. Human dermal fibroblasts were differentiated to myofibroblasts using TGFβ-1 in the presence of MSC-S. After 24 hr, qPCR was performed on total isolated RNA. MSC-S reduces the expression of scarring biomarkers TGFβ2 and SMA. Data represent the mean±SD of nine replicates. Comparisons were performed using a one-way analysis of variance (ANOVA) followed by a post hoc Dunnett's test; * $p<0.05$, *** $p<0.0001$.
Figure 7B:
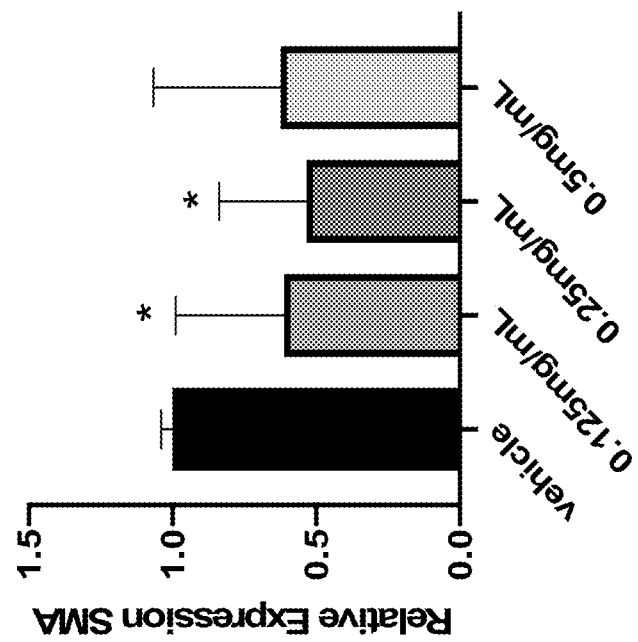

Evaluation of the anti-scarring capabilities of MSC-S was performed. Following corneal trauma, fibroblasts in the stroma differentiate to myofibroblasts, the hallmark of scarring, in a process characterized by several biomarkers. Myofibroblast differentiation can be replicated in vitro using dermal fibroblasts and treatment with TGFβ-1, a potent inducer of differentiation (Li, M. et al., *Int Wound J.* 2017 February; 14(1):64-73.). The ability of MSC-S to impair differentiation using this assay was evaluated and qPCR was used to evaluate the expression of key biomarkers, TGFβ-2 and Smooth Muscle Actin (SMA), which are both upregulated during myofibroblast differentiation (FIG. 7). Data showed that MSC-S had a potent effect at dampening the expression of both TGFβ-2 and SMA, indicating the inhibition of myofibroblast differentiation. Therefore, MSC-S demonstrated anti-scarring properties and the potential to mediate scarless corneal wound healing.

MSC-S Increases In Vitro Corneal Cell Proliferation.

To evaluate the ability of MSC-S to promote cell proliferation, in vitro assays were performed using primary rabbit corneal epithelial cells. When incubated with MSC-S, proliferation increase in a dose-dependent manner following incubation in primary rabbit corneal cells (see, for example, Femandes-Cunha, G M, et al., Stem Cells Transl. Med. 2019).

MSC-S Improves In Vivo Wound Closure in Different Corneal Trauma Models.

After demonstrating increased cellular proliferation in an in vitro setting, wound healing was evaluated following mechanical corneal injury in a murine model. MSC-S was administered as a single drop daily for 4 days and evaluated 24 hours post cessation of treatment. Significant wound closure was observed for the eyes that received MSC-S compared to saline (see, for example, Femandes-Cunha, G M, et al., Stem Cells Transl. Med. 2019)(*, p<0.05).

Figure 8:
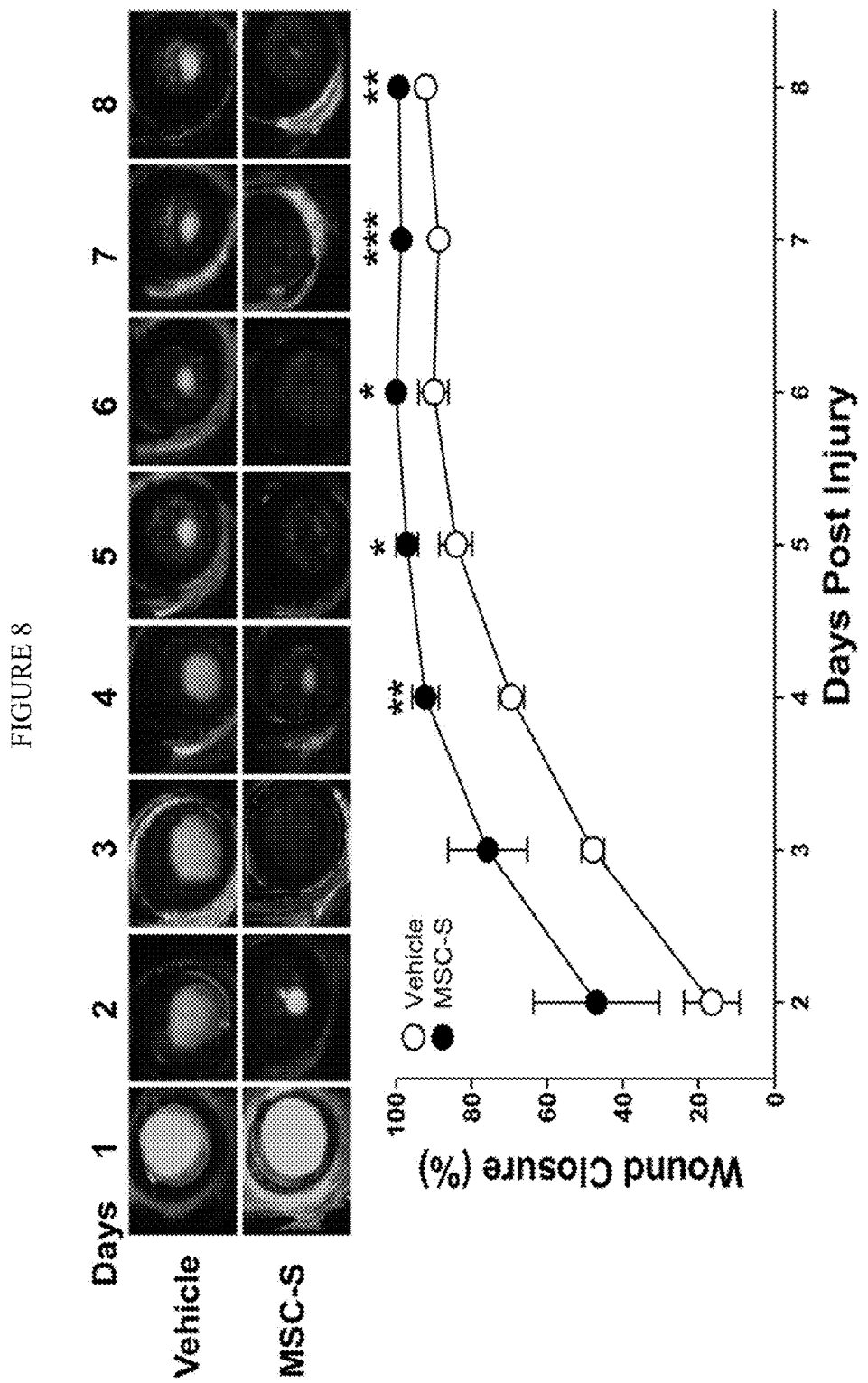
FIG. 8. MSC-S treatment significantly ameliorates corneal alkali burn injury-induced wound closure. Alkali burn animal model: Brown Norway rats (150 g. 10 weeks old) were deeply anesthetized via subcutaneous administration of ketoprofen prior to S.C. injection of ketamine/xylazine. One drop of topical proparacaine was then applied to the intended to treat right eye. An alkali burn was then created in the right eye of each deeply anesthetized rat by placing a 5 mm diameter circular piece of filter paper soaked in 1N NaGH on the center cornea for 30 seconds followed by washing with 100 ml of balanced salt solution (BSS). Post-operative pain management was achieved by SC injections of ketoprofen every 24 hours for a total of 3 administrations. The animals were then randomly allocated into two treatment groups; Vehicle (n=4) and MSC-S (n=4-5). Eyes were stained with fluorescein (20 μl of 1.0% fluorescein phosphate diluted in BSS) and photographed at initial wounding and each day after the induction of the alkali burn to measure the area of the epithelial defect. Immediately following the initial fluorescein staining, topical treatment was begun; Vehicle (BSS, 5 uL) and MSC-S (5 mg/mL, 5 μL) three times a day (TID) for 7 days. The area of the corneal scrape wound was quantified from the photographs using a computer-assisted image analyzer (Image J 1.38x: National Institutes of Health, Bethesda, Md.). The extent of healing was determined by the ratio of the difference between the immediate insult and the remaining wound areas after each 24 h period. A two-tailed unpaired t-test was performed using GraphPad Prism version 8.0.0 for Windows, GraphPad Software, San Diego, Calif. USA, www.graphpad.com. Data presented in mean±SE: $*p<0.05$, $p<0.01$, and $*p<0.001$.
Figure 9:
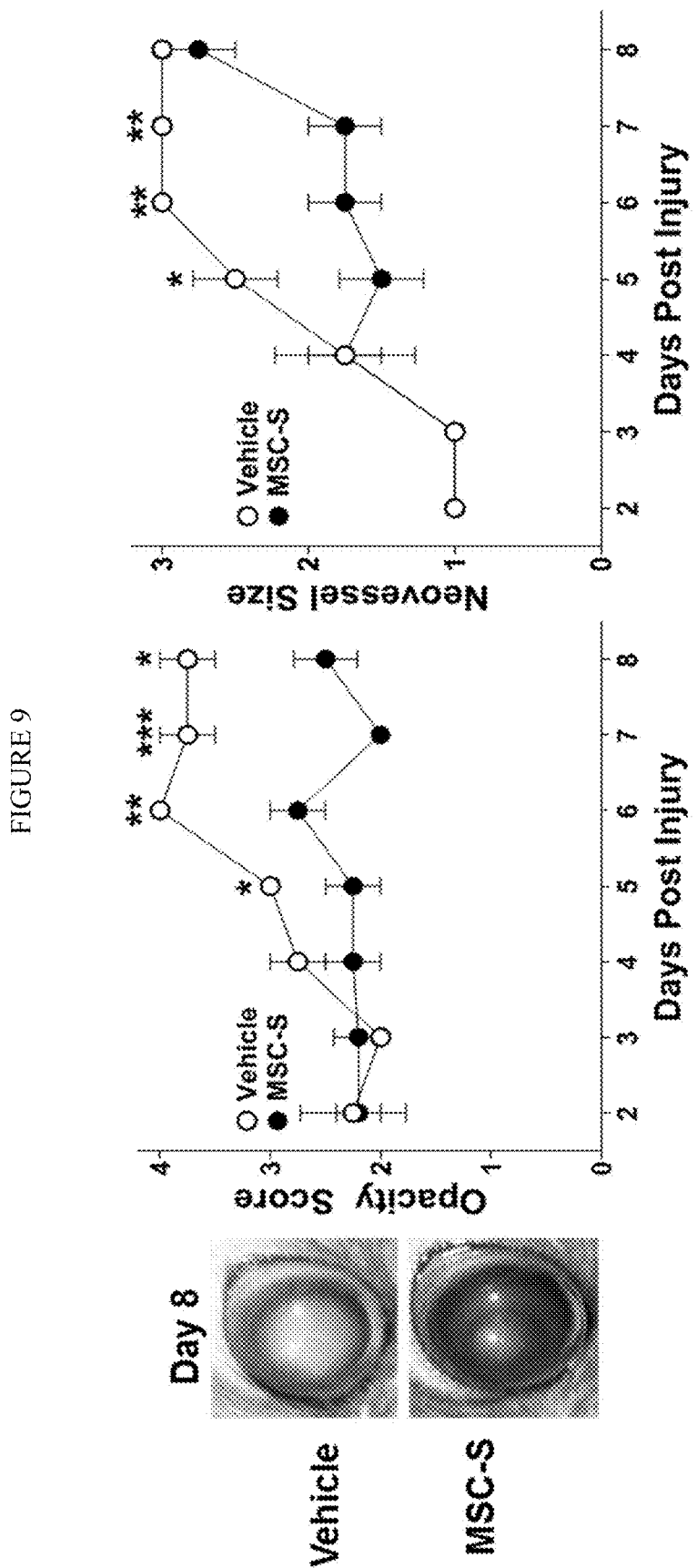
FIG. 9. MSC-S treatment significantly improves corneal opacity and neovessel size. Corneal burn injured eyes were treated with Vehicle (n=4) and CMB-012 (n=4-5) TID for 7 days. Corneal opacity on a scale of 0-4. 0=completely clear; 1=slightly hazy, iris and pupil easily visible; 2=slightly opaque, iris and pupil still detectable; 3=opaque, pupils hardly detectable; and 4=completely opaque with no view of the pupil. Neovessel size on a scale of 0-3. 0=no neovessels; 1=neovessels detectable under surgical microscope; 2=neovessels easily seen under surgical microscope; 3=neovessels easily seen without the microscope. A two-tailed unpaired t-test was performed using GraphPad Prism version 8.0.0 for Windows, GraphPad Software, San Diego, Calif. USA, www.graphpad.com. Data presented in mean±SE: $*p<0.05$, $p<0.01$, and $*p<0.001$.

A second lot of MSC-S (formulated in BSS) was evaluated using a corneal alkali burn model in rats. Topical application of MSC-S to corneal alkali burn injury-induced rats significantly reduced corneal damage (FIG. 8). Alkali burning induced very apparent severe corneal damage including severe epithelial wounds, neovascularization and opacification, which persisted through to Day 8 (FIG. 8). FIG. 8 illustrates substantial epithelial damage induced by the alkali burn with only 16.7±14.3%, 48.0±6.04%, and 69.4±6.74% wound closure on Days 2, 3 and 4 post injury for the vehicle-control group in contrast to the MSC-S treated group with exhibited substantial improvements in wound closure with 47.0±37.2%, 75.7±23.6%, and 92.1±5.73%, respectively.

MSC-S Decreases Opacity and Neovessel Size in Corneal Chemical Burns.

Figure 10:
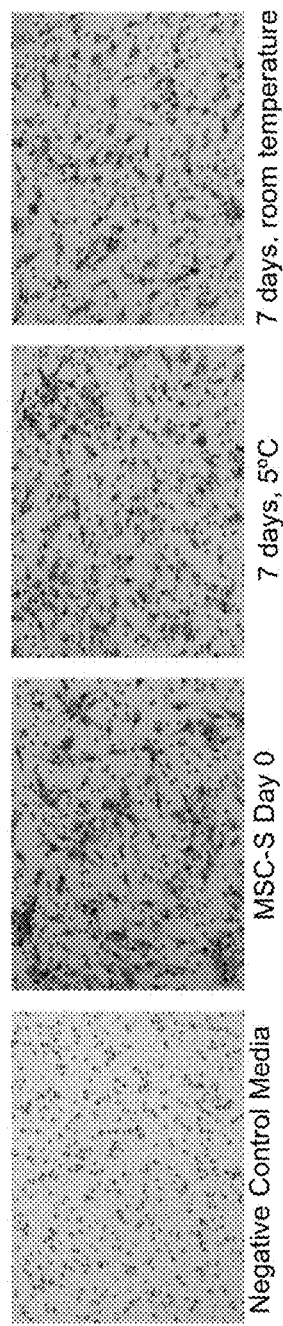
FIG. 10: MSC-S MAINTAINS PRO-MIGRATION BIOACTIVITY FOR 7 DAYS WHEN STORED AT 5° C. AND 25° C. (AMBIENT TEMPERATURE) [STUDY CM19_TWS01]. The cell-based migration stability biassay utilizes a transwell migration principle and primary corneal fibroblasts. Briefly, cells are seeded in basal (nutrient depleted) media in an upper chamber with a porous membrane. The chamber is then placed in a well of basal media containing MSC-S. After 24 hours the migrated cells on the bottom surface of the membrane are stained, imaged, and quantitated.

MSC-S significantly decreased opacity and neovessel size in the corneal alkali burn model (FIG. 10). The opacity scores for the vehicle treated group, were 3.0±0, 4.0±0, 3.75±0.5 and 3.75±0.5 on Days 5, 6, 7 and 8 compared to 2.25.0±0.5, 2.75±0.5, 2.0±0 and 2.5±0.6 for the MSC-S treated group (*p<0.05, p<0.01, *p<0.001 and *p<0.05, respectively). Moreover, the neovessel size scores for vehicle-control treated group were 2.5.0±0.6, 3.0±0, and 3.0±0 on Days 5, 6 and 7 compared to 1.5.0±0.6, 1.75±0.5, and 1.75±0.5, respectively for the MSC-S-treated group (*p<0.05, p<0.01, p<0.01). This data is consistent with the in vitro data which showed the anti-angiogenic properties of MSC-S (FIGS. 5 and 6) and anti-scarring properties of MSC-S (FIG. 7).

Example 4: An Ophthalmic Pharmaceutical Formulation Containing MSC Secretome, MSC-S which is Safe and Effective in Treating Corneal Wounds Topical ophthalmic drug development is impeded by many anatomical constraints including tear turnover and dilution, nasolacrimal drainage, and reflex blinking with often less than 5% of the topically administered dose reaching deeper ocular tissues (Gaudana et al., 2009). In the case of corneal wounds, the initial insult causes rifts in the corneal epithelium thereby enabling the passage of topically applied MSC-S to penetrate the epithelial layers. The residence time of the formulated therapeutic on the cornea may be too limited therefore a formulation strategy can be evaluated including 1) evaluation of pH, including mimicking the pH of tears (pH 7.4) to reduce stinging and tearing, 2) maximizing the concentration of the MSC secretome to overcome tear dilution and optimize the effective dose delivered, without causing adverse events, 3) utilizing an FDA-approved viscous mucoadhesive agent, Hydroxyl propyl methyl cellulose (HPMC, hypermellose), to increase residence time, increase ocular penetration and provide sustained therapeutic delivery, 4) increasing lipophilicity of the formulation to optimize penetration of the cornea without causing unselective eukaryotic toxicity. All of these formulation changes must ensure the MSC-S remains stable and potent The formulation can be the most stable, tolerable formulation while maintaining therapeutic potency. The FDA approved pharmaceutical excipient, HPMC can be utilized for initial evaluation, and modified as necessary to achieve an effective suitable, and stable formulation. HPMC is a semisynthetic, inert, viscoelastic polymer, used extensively as an ophthalmic lubricant and a controlled-delivery agent. Its bioadhesive properties are attributed to the formation of hydrogen bonding between carboxylic acid group of cellulosic polymers and glycoprotein of mucin present in the mucosal layer. Buffers such as phosphate, acetate or citrate, containing osmolality-adjusting agents such as salts, sorbitol or propylene glycol, can be added to increase viscosity, lipophilicity and hence, residence time.

Formulations of appropriate pH (pH 6.8 and 7.4) and tonicity (285 mOsm/L), and gelled to appropriate viscosity (e.g., 15 to 150 mPa-s), for stability assessment. Two prototype formulations can be developed for use in providing clinical patients to be treated or undergoing treatment to develop a 1-week take home supply that can be stable at 2-8° C. A 1-month stability evaluation can be conducted to assess the physical and chemical stability of the selected prototype formulations; timepoints will include time zero and then 1, 2, and 4 weeks at 2-8° C. and then 1 week at room temperature (accelerated stability). The samples can be assayed for bioactivity.

Such a MSC-S formulation will provide a more efficacious drug product due to an increase in viscosity of the formulation and therefore increased dwell time of the antimicrobial on the ocular surface.

Evaluation of the Ocular Tolerability of the Optimized MSC Secretome Formulations:

Ocular irritation studies can be employed to verify that the MSC-S and the excipients in the drug product formulation can be tolerable to the patients. To reduce animal testing, the ocular irritation evaluation can be conducted using the EpiOcular™ eye irritation test, a human cell-derived in vitro corneal tissue model. The EpiOcular™ eye irritation test is an in vitro alternative to the Draize rabbit eye test (Kandarova et al., 2019).

Tolerance to human corneal cells can be evaluated using the EpiOcular™ eye irritation test. Tolerance can also be evaluated using bioluminescent human epithelial cell-based assays (Lumigenics).

The formulations with the best safety profile can be evaluated in the rodent corneal wound model.

Evaluation of the Therapeutic Potential of the Optimized Formulations in a Rodent Chemical Burn Model:

The use of the corneal alkaline burn wound model is the most clinically relevant corneal burn wound model at present (Chen et al., 2016: Fernandes-Cunha et al., 2019). Alkaline burns of the cornea can be induced in the left eye of each rat. A filter paper disc (5 mm in diameter) soaked with 1 M NaOH was placed on the center of the corneal surface for 30 seconds, followed by irrigation with 200 ml of saline. Beginning immediately after the corneal alkaline burn, animals received treatments (See, Choi, H., et al., *Curr Eye Res.* 2017 October; 42(10):1348-1357). Neovascularization, opacification, and epithelial defect can be evaluated in the corneal alkaline burn wound model.

Statistical analysis comparing the effects of treatment across groups can be performed using a one-way ANOVA with a Dunnett's post hoc comparison test using either vehicle control or treatment groups as references. Data can be considered as significantly different at P<0.05.

Corneal wounds can be expected to develop in the vehicle control eyes as evidenced by the robustness of this clinically relevant rodent wound model and by the results exhibited in previous studies (Femandes-Cunha et al., 2019). If, consistent wounds are not observed, changing experimental parameters such as changing the amount of time the sodium hydroxide is placed on the cornea, and/or size and change of strain of rat can be employed. A more efficacious drug product, compared to that formulated in HBBS, can be due to the addition of the mucoadhesive, HPMC, a presumed increase in viscosity of the formulation and therefore increased dwell time of the MSC-S on the ocular surface. This will manifest as significantly lower clinical score, decreased wound size, neovascularization, opacification and epithelial defect (update as appropriate). The higher MSC-S dose is also expected to be more efficacious than the lower concentration. In some cases, increasing the frequency of topical application of the MSC-S or changing the MSC-S formulation loading dose can be employed to evaluation efficacy.

Example 5: Chemical Burns of the Cornea and/or Persistent Corneal Epithelial Defects (PCED)

Summary of Chemistry, Manufacturing and Controls

MSC-S, derived from human bone marrow-derived mesenchymal stem cell secretome, is composed of a mixture of biologically active endogenous components, including cytokines and growth factors, present at physiologic levels. Mesenchymal stem cell secretome comprises highly potent biological substances such as chemokines, cytokines, growth factors, proteins, enzymes, and ribonucleic acids (RNAs).

The entire MSC-S production process, including Master Cell Bank (MCB) and Working Cell Bank (WCB) creation, will be performed in compliance with current Good Manufacturing Practice (cGMP). The donor mesenchymal stem cell (MSC) was tested and confirmed to be negative for viruses and communicable disease agents.

MSC-S manufacturing begins with a MCB derived from a single draw of donor MSC. A WCB is created from the MCB, and a batch of secretome is produced from the WCB, concentrated, and diafiltrated to produce the MSC-S Drug Substance. MSC-S Drug Product is formulated by combining 6 μg of MSC-S Drug Substance with compendial pharmaceutical excipients for ophthalmic drugs to produce 5 mL of MSC-S Drug Product.

MSC-S will be formulated for topical ophthalmic delivery and is packaged in eye drop bottles with each bottle intended for one day's use. The bottled MSC-S will be thawed in a refrigerator for up to 24 hours before use and stored under refrigeration during the intended day's use.

Summary of Nonclinical Findings

Nonclinical assessments of MSC-S include in vitro pharmacology studies, in vivo pharmacology in the rat, in vitro irritancy in a human tissue model, and repeat-dose toxicology studies in rats and rabbits.

Transwell migration assays found MSC-S to stimulate migration of corneal epithelial cells and human primary fibroblasts. The pro-migratory effect of MSC-S was also confirmed using a wound gap assay, where MSC-S enhanced the healing of a gap in a corneal epithelial cell monolayer compared to control.

A biochemical evaluation of the protein composition of MSC-S using human angiogenesis protein arrays, supports the anti-angiogenesis ability of MSC-S as the most prominent proteins present were 2-7 fold excess of the pro-angiogenic molecules. A human umbilical tube formation assay, a well-established in vitro model to evaluate angiogenic potential of therapeutic compounds, demonstrated MSC-S did not promote angiogenesis, and it attenuates tube formation parameter compared to vascular endothelial growth factors alone.

MSC-S was assessed in an alkali burn dose-ranging study in Brown Norway Rats. MSC-S at 0.6 or 6 μg/mL administered topically 3× daily enhanced wound closure and reduced corneal opacity and neovascularization in this study, suggesting that MSC-S may be a potential therapeutic agent for corneal re-epithelialization after corneal trauma.

An in vitro irritancy study conducted in EpiOcular human tissue model found MSC-S to be non-irritating, with the exposure needed for a test article to reduce the viability of treated tissue to 50% of control tissue ($ET_{50}$) greater than 60 minutes for both control and MSC-S.

Repeat-dose toxicology was assessed in the rat and in the rabbit. A repeat-dose range finding study was conducted in rats to identify doses to investigate in the formal Good Laboratory Practice (GLP) rabbit toxicology study. To match the treatment duration of the clinical study, a 14-day GLP toxicology study following ocular instillation of MSC-S was conducted in rabbits. The rabbit was chosen as the toxicology species due to anatomical similarity to human eyes; 13 mm rabbit corneal diameter versus 11 mm corneal diameter in humans and decreased blink rate; every 6 minutes in rabbits compared to every 5 seconds in humans, therefore providing a rigorous safety test for the ocular exposure of MSC-S (Vézina 2012).

887 778'564443

Introduction

Overview of the Product

MSC-S is a novel mesenchymal stem cell secretome (MSC-S) therapy and is being developed to treat sight-threatening corneal wounds. MSC-S is composed of a mixture of biologically active components, including cytokines and growth factors, present at physiologic levels that have been shown to accelerate corneal wound healing and reduce scarring, inflammation, and corneal neovascularization in nonclinical studies in an alkali chemical burn model in rats.

Human MSCs are a heterogenous population of fibroblast-like cells isolated from many adult tissues including bone marrow, blood, skeletal muscle, placenta, amniotic fluid and the limbal stroma of the human cornea. MSCs exhibit substantial regenerative potential due to the 4865437684538 ir capacity for self-renewal, high plasticity, immune response modulation, and ability for genetic modification (Ferreira et al. 2018; Harkin et al. 2015). The bio-factors produced by MSCs, which are commonly referred to as MSC-S, comprises highly potent biological endogenous substances such as chemokines, cytokines, growth factors, proteins, enzymes, and RNAs. The literature is replete with pre-clinical studies underscoring the therapeutic potential of MSC-S, including for corneal epithelial wound healing (Samaeekia et al. 2018; Vizoso et al. 2017). Additionally, because MSC-S is a cell-free therapy and is obtained from conditioned media which does not require invasive cell collection procedures, it possesses several key advantages for clinical and commercial translation over stem-cell therapy. These advantages include elimination of safety risks of implanted MSC (tumorigenicity, immune system rejection and migration, more immediate availability for acute treatments (enabled by avoiding invasive cell collection procedures), potential for controlled production, release and potency (similar to conventional pharmaceutical agents), long-term storage, stability and portability, and reduced sourcing costs.

MSC-S Drug Substance is manufactured using a cGMP-compliant MSB derived from cGMP MSCs. MSCs were thawed, seeded, and expanded to produce a volume of 3.0 L of intermediate MSC-S Drug Substance. The intermediate is then concentrated and diafiltrated to formulate the final MSC-S Drug Product formulation for aseptic filling of eye drop bottles.

MSC-S is delivered via topical ocular instillation in 5 mL eye drop bottles. MSC-S is formulated to contain 6 μg/mL of MSC-S Drug Substance formulated (per mL) in monobasic sodium phosphate, anhydrous (2.28 mg), dibasic sodium phosphate, dried (11.45 mg), trehalose dihydrate (24 mg), mannitol (12.2 mg), hypromellose (0.1 mg), Water for Injection, United States Pharmacopeia (USP) grade, and hydrochloric acid and/or sodium hydroxide to adjust pH.

Overview of Targeted Disease and Indication

The cornea serves a protective role as the outermost tissue of the eye, yet it is highly vulnerable to severe injury and disease. Its lack of blood vessels confers its transparency, but also limits its ability to heal. In the United States (US), over 2.4 million individuals experience eye injury with the estimated incidence rate presented at emergency departments or eye-trauma centers of approximately 3.15 per 1000 population (McGwin and Owsley 2005; Serrano et al. 2013).

Severe injuries such as chemical burns can extensively damage the ocular surface epithelium, cornea, anterior segment and limbal stem cells, and frequently result in vision loss, disfigurement, and challenging ocular surface complications (Baradaran-Rafii et al. 2017; Singh et al. 2013). Chemical burns can be caused by acid or alkali exposure, with alkali burns being more severe. Alkali burns can penetrate the anterior chamber more easily than acid, and can result in cataract formation, damage to the ciliary body and damage to the trabecular meshwork (Singh et al. 2013).

Ocular injuries are classified by the amount of limbal involvement at the time of injury, with no limbal ischemia predictive of the best prognosis (Baradaran-Rafii et al. 2017). The clinical course of chemical burns of the cornea can be divided into four phases: immediate phase, acute phase, early reparative phase, and late reparative and sequelae phase. The defining clinical characteristics of the phases of corneal injury is summarized in Table 1.

TABLE 1

Phases and clinical characteristics of corneal burns

| Phase | Time frame | Clinical characteristics |
| --- | --- | --- |
| Immediate | The moment a chemical agent comes into contact with the ocular surface | Injuries resulting in defect of the cornea and conjunctiva, limbal blanching, corneal opacification, increased intraocular pressure, and loss of lens clarity. |
| Acute | First 7 days after injury | Tissues rid themselves of contaminants while reestablishing the superficial protective layer of corneal epithelium. |
| Early reparative | 8-20 days after injury | This phase is characterized by chronic inflammation, stromal repair and scarring. The regenerating corneal epithelium and polymorphonuclear leukocytes releases collagenase, metalloproteinase and other proteases. |
| Late reparative | Three weeks after injury | This stage is characterized by completion of healing. |

(Singh et al. 2013)

An epithelial defect that does not heal within the expected time frame of one to two weeks despite conventional treatment is defined as persistent corneal epithelial defect (PCED) (Katzman and Jeng 2014). There are many risk factors that might contribute to PCED, including corneal hypesthesia, diabetic keratopathy, limbal stem cell deficiency, dry eye disease, exposure keratopathy, and neurotrophic keratopathy from herpetic infections or previous corneal transplantation (Katzman and Jeng 2014). Regardless of the etiology, treatment of PCED remains challenging and the outcome has a severe impact on the quality of life of the affected patient.

Current Therapies

The management of corneal wounds has not changed significantly in the last few decades and consists mainly of supportive measures in the form of lubrication, antibiotics, steroids, patching, autologous serum eye, and in some cases, sutured lid closure or amniotic membrane grafting (Baradaran-Rafii et al. 2017; Ziaei, Greene, and Green 2018). These treatments have had limited success, and pose issues with logistics, procedural invasiveness, and patient intolerance. Thus, there is an unmet critical need for improved ocular surface healing therapies for patients with severe ocular surface injuries (Femandes-Cunha et al. 2019).

Physical, Chemical, and Pharmaceutical Properties and Formulations

MSC-S is composed of a mixture of biologically active endogenous components, including cytokines and growth factors, present at physiologic levels. The MSC-S Drug Substance intermediate is the secretome derived from human bone marrow-derived MSCs. This example provides a MCB derived from a single draw of MSCs from a single donor and a WCB from this MCB. A batch of secretome was produced using a vial of WCB, then concentrated and diafiltrated to produce the MSC-S Drug Substance. MSC-S Drug Product was formulated with compendial pharmaceutical excipients for ophthalmic drugs by combining 6 μg of MSC-S Drug Substance (per 1 mL) in monobasic sodium phosphate, anhydrous (2.28 mg), dibasic sodium phosphate, dried (11.45 mg), trehalose dihydrate (24 mg), mannitol (12.2 mg), hypromellose (0.1 mg), Water for Injection, USP, and hydrochloric acid and/or sodium hydroxide to adjust to pH 7.4.

The entire MSC-S production process, including MCB and WCB creation, is performed in compliance with cGMP. A description of the MCB, WCB and secretome extract and characterization are described in the following sections.

Original Master Cell Bank Manufacture

The MSC used to create the MCB (donor MSC) was derived from human bone marrow from a normal healthy donor and expanded 2 passages using controlled manufacturing processes under cGMP conditions. These cells were characterized for expansion potential, cell surface marker expression and differentiation potential into adipocytes, osteocytes and chondrocytes. They were characterized after a 2-passage expansion, cells at passage 4 (P4), to have cell expansion potential, were predominantly (≥80%) CD166 and CD90 positive cells with ≤20% positive for CD34 and CD45 (haemopoietic lineage), showed differentiation in to the expected osteocytes, chondrocytes and adipocytes and showed immunomodulatory activity through the induction of the enzyme, indoleamine 2, 3 dioxygenase which mediates potent local effects on innate and adaptive immune responses to inflammatory insults, following stimulation with interferon-gamma (IFN-γ) and the formation of kynurenine, a marker of immune activation. MSCs were also confirmed to be from a normal human male following passage and expansion.

Donor MSC was tested and confirmed negative for various viruses and other communicable disease agents including human immunodeficiency virus, hepatitis B and C, human T-lymphotropic virus, cytomegalovirus, Epstein Barr Virus, human papilloma virus, adeno-associated virus, human herpes virus 6, parvovirus, human transmissible spongiform encephalopathies and mycoplasma.

Donor MSC was manufactured and characterized at a cGMP-compliant manufacturing site and the Certificate of Analysis for donor MSC recorded negative sterility, endotoxin levels <0.50 endotoxin units (EU)/mL, negative mycoplasma and adventitious agents not detected, confirmed as human cells with 100.0% cells showing CD90, 97.8% with CD166, 1.2% with CD34 and 1.4% with CD45 surface markers. Cell count was $2.3 \times 10^7$ cells per vial with 98% calculated viability. Cells were passaged and cells were characterized following this expansion, and confirmed to be viable, predominantly (≥80%) CD166 and CD90 positive cells with ≤20% positive for CD34 and CD45 (haemopoietic lineage). The passaged cells were tested and met release criteria for mycoplasma (negative), sterility (negative), bacteriostasis/fungistasis (no inhibition), and endotoxin (<10 EU/mL).

Working Cell Bank

The cells were characterized following this expansion, and confirmed to be viable, predominantly (≥80%) CD166 and CD90 positive cells with ≤20% positive for CD34 and CD45 (haemopoietic lineage). The cells were tested and met release criteria for mycoplasma (negative), sterility (negative) and endotoxin (<10 EU/mL). These vials were frozen and stored for future use in the manufacture of MSC-S as described below.

MSC-S Drug Substance Manufacture

The cells were used to make clinical grade MSC-S. Vials were thawed, seeded, and harvested to produce a 3 L batch of intermediate MSC-S Drug Substance (Human mesenchymal stem/stromal cell [hMSC] secretome). The endogenous biological components of the secretome include TIMP-1 (Tissue inhibitor of metalloproteinase-1), HGF (Hepatocyte growth factor), VEGF (Vascular Endothelial Growth Factor) and EVs (Extracellular vesicles).

The secretome intermediate drug substance was then concentrated and diafiltered to provide 300 mL of purified MSC-S Drug Substance. The physical and chemical properties of the final MSC-S Drug Substance is provided in Table 2.

TABLE 2

Physical and Chemical Properties of the Drug Substance

| Substance | MSC-S |
| --- | --- |
| Approved Name (USAN): | Not assigned |
| Chemical Name (IUPAC): | Not assigned |
| Molecular Weight: | Range of proteins of MW 20-60 kDa |
| Physical Form: | MSC-S Drug Substance is a clear colorless liquid |
| pH: | 7.0-7.4 |
| Osmolarity: | 280-320 Milliosmoles (mOsm)/kg |

USAN = United States Adopted Name, IUPAC = International Union of Pure and Applied Chemistry Pharmaceutical Presentation The final Drug Product was formulated. The MSC-S Drug Product was filled aseptically into standard medical-grade USP Class VI polyethylene resin sterile eye drop bottles. Each bottle contained 5 mL of MSC-S formulation. Details of the formulation per bottle is provided in Table 3.

MSC-S Drug Product was a sterile clear, colorless solution with a pH of 7.0-7.4 and osmolarity of 280-320 mOsm/kg. The Certificate of Analysis of final Drug Product confirms that it met release criteria for mycoplasma (negative), bacteriostasis/fungistasis (no inhibition), sterility (negative) and endotoxin (<10 EU/mL).

Each bottle (5 mL) of MSC-S Drug Product was intended to be used for a single day's dosing only.

Formulation Including Excipients

MSC-S ophthalmic solution is a sterile solution formulated as shown in Table 3. MSC-S Drug Product is prepared by combining 6 μg of MSC-S Drug Substance (% w/w) with compendial pharmaceutical excipients approved for ophthalmic drugs including monobasic sodium phosphate, anhydrous (0.27 mg), dibasic sodium phosphate, dried (1.09 mg); mannitol (0.4 mg), hypromellose (0.1 mg), Water for Injection, USP, and hydrochloric acid and/or sodium hydroxide to adjust pH 7.4.

TABLE 3

MSC-S Product Formulation

| Constituent Present | Amount per 1 mL of product | Percent present (%) per 1 mL |
| --- | --- | --- |
| MSC-S (hMSC secretome) | 0.006 mg (6 ug) | 0.012 |
| Monobasic sodium phosphate | 2.28 mg | 4.5 |
| Dibasic sodium phosphate | 11.45 mg | 22.4 |
| Mannitol | 12.2 mg | 24.0 |
| Trehalose Dihydrate | 24 mg | 47.1 |
| Hypromellose | 1 mg | 2.0 |
| Hydrochloric acid and/or sodium hydroxide | adjust as required | adjust as required |
| Total quantity | 50.936 mg | 100% |

Storage and Handling

Each MSC-S Drug Product is to be stored at −20° C. at the Clinical Site and thawed in a refrigerator (2-8° C.) and stored refrigerated for up to 24 hours before the intended day's use. During the intended day's use, MSC-S should be stored refrigerated. Storage and handling details are described in the Study Protocol.

Stability Data

MSC-S Drug Product has been assessed for stability. MSC-S was formulated and put on a stability program to evaluate physical characteristics and bioactivity after store at 25° C. or 5° C. for fixed periods of time. Specifically, physical appearance, pH, osmolality, and viscosity were evaluated. The physical attributes were evaluated at 5° C. for up to 30 days, and at 25° C. for 1 week; no significant changes were observed over the duration of the stability program. In addition, the stability of MSC-S was evaluated using a cell-based migration bioassay (assay described below). FIG. 10 shows MSC-S maintains potent pro-migration behavior when stored for 7 days at 5° C. and 25° C. (ambient temperature).

The bottled product remains stable at −20° C. for up to six months following manufacture. MSC-S is stable at refrigerated storage condition (2-8° C.) for at least one day and stable at room temperature for short duration (<4 hrs). Based on the available stability data, the sponsor has assigned a shelf life of 6 months from the date of manufacture for the MSC-S ophthalmic solution. The shelf life may be extended based on data generated from on-going/future stability studies MSC-S ophthalmic solution should be stored at −80° C. Prior to use it should be thawed and stored refrigerated (2-8° C.) for up to 24 hours before and during the intended day's use.

Nonclinical Studies
Introduction
Nonclinical Development Program

A comprehensive nonclinical program has been conducted to support the clinical development of MSC-S for treatment of corneal wounds by topical ocular administration. The nonclinical development program consists of primary pharmacology and toxicologic evaluation. A summary of these studies is provided in the present example. In all in vivo studies, the investigational medicinal product (IMP) was delivered via topical ocular instillation, the intended route for clinical dosing.

Nonclinical Test Material Formulation

Test material for non-clinical studies was formulated in buffered saline solution similar in composition to the clinical formulation. All in vitro cell-based assays were performed directly with test article formulated in buffered saline and in vivo studies were performed with test article formulated in buffered saline plus HPMC.

In Vitro Pharmacology
MSC-S Promotes the Migration of Human Primary Corneal Epithelial Cells and Corneal Fibroblasts [Study CM19_TWM01]

Figures 11A, 11B:
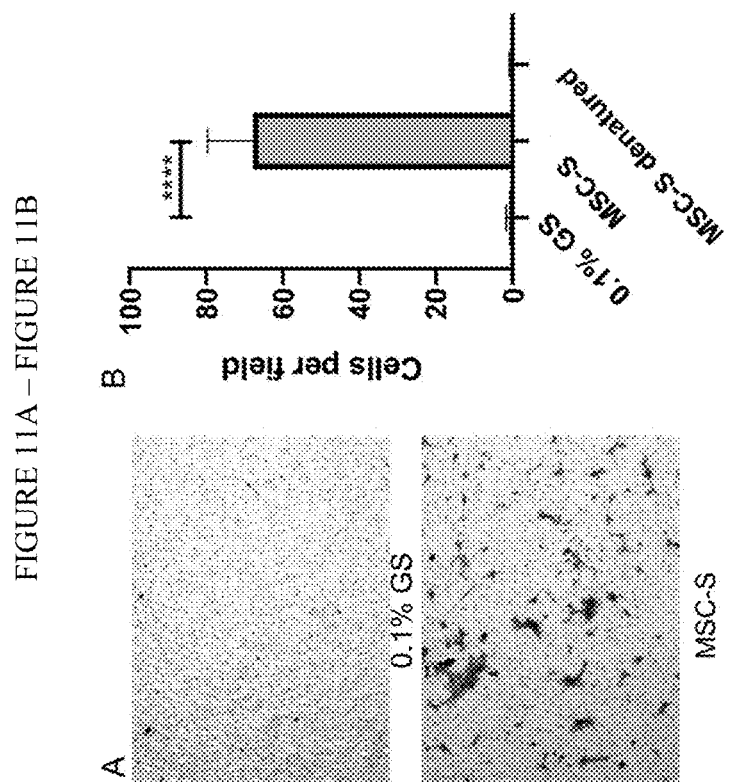
FIG. 11A-FIG. 11B: MSC-S PROMOTES THE MIGRATION OF HUMAN PRIMARY CORNEAL EPITHELIAL CELLS. Pictured are the bottom sides of the transwell membrane after 24 hr incubation with 0.1% growth supplement (GS, A) or MSC-S (300 μg/mL, B). Migrated cells were enumerated in 3 fields per replicate over 3 replicates per treatment; denat: denatured with heat at 90° C. for 10 min. Data presented is mean±SE, $****p<0.0001$ using a two-tailed unpaired t-test.

MSC-S promoted the migration of human primary corneal epithelial cells. Following a corneal trauma, corneal epithelial cells at the leading edge begin to migrate to close the wound. The ability of MSC-S to promote migration was evaluated using a transwell migration assay. Briefly, cells were seeded in basal (nutrient depleted) media in an upper chamber with a porous membrane. The chamber was then placed in a well of basal media containing MSC-S. After 24 hours the migrated cells on the bottom surface of the membrane were stained, imaged, and quantitated. Firstly, MSC-S was found to stimulate migration of corneal epithelial cells, a process critical to rapid wound healing. Further, as anticipated, heat (90° C./10 min) abrogates the migration promoting activity of MSC-S due to denaturation of the protein components (FIG. 11).

MSC-S Promotes Corneal Epithelial Cell Wound Closure [Study CM19_WGA01].

Figures 12A, 12B:
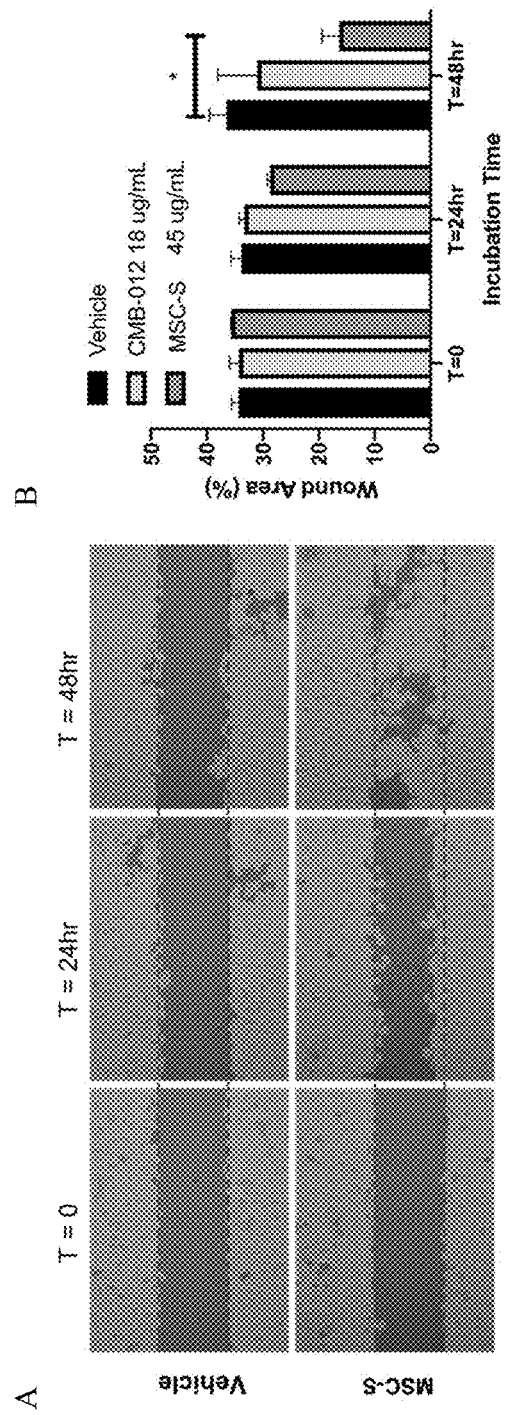
FIG. 12A-FIG. 12B: MSC-S IMPROVES CLOSURE OF A WOUND GAP IN A CONFLUENT MONOLAYER OF HUMAN PRIMARY CORNEAL EPITHELIAL CELLS. A) Pictured are representative images of the wound gap in a human primary corneal epithelial cell monolayer treated with vehicle control (top panel) or MSC-S (45 μg/ml; bottom panel)), and imaged at T=0, 24, and 48 hours. The cell monolayer is depicted in green and the dashed lines (red) correspond to the wound gap. B) Wound gap closure is significant improved when cells are treated with 45 μg/ml MSC-S for 48 hr. A two-tailed unpaired t-test was performed using GraphPad Prism version 8.0.0 for Windows, GraphPad Software, San Diego, Calif. USA. Data presented is mean±SE: $*p<0.001$.

The pro-migratory effect of MSC-S was also confirmed using a wound gap assay. In this wound healing assay, a "wound gap" in a cell monolayer is created and the "healing" of this gap by cell migration and growth towards the center of the gap is monitored. In this assay, primary corneal epithelial cells treated with MSC-S demonstrate enhanced healing of the wound gap relative to vehicle (negative) control (FIG. 12).

MSC-S Promotes the Migration of Human Primary Fibroblasts [Study CM19_TWM02]

Figure 13:
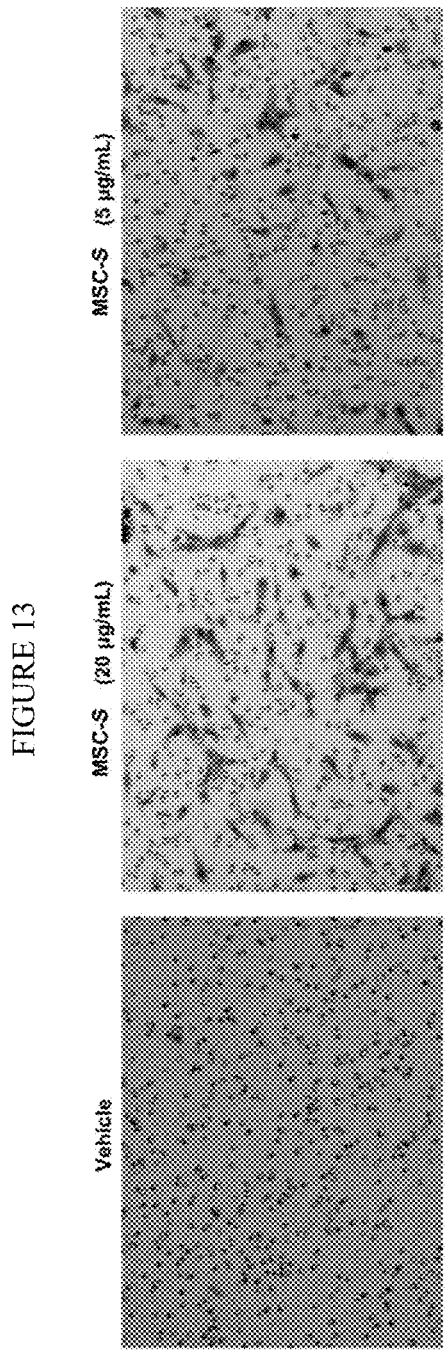
FIG. 13: MSC-S PROMOTES THE MIGRATION OF HUMAN PRIMARY CORNEAL FIBROBLASTS. Pictured are the bottom sides of the transwell membrane after 20 hours of incubation with MSC-S or vehicle control.

Following a corneal trauma, corneal fibroblasts migrate from the surrounding stroma into the affected region. Similar to the effect observed with corneal epithelial cells, a potent pro-migratory response was observed in primary corneal fibroblasts treated with MSC-S (FIG. 13).

MSC-S Exhibits a Negative Angiogenic Potential
MSC-S Composition Supports Anti-Angiogenesis [Study CM19_PA01]

Figures 14A, 14B:
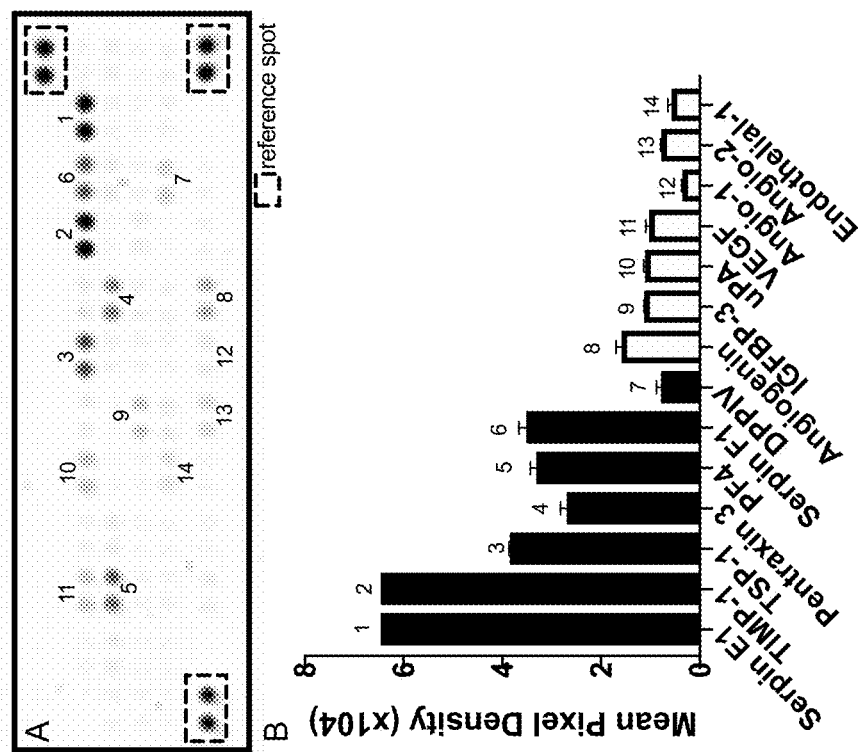
FIG. 14A-FIG. 14B: MSC-S EXHIBITS AN ANTI-ANGIOGENIC PROTEIN PROFILE. A) A human angiogenesis array was used to identify pro- and anti-angiogenic protein factors in MSC-S. The pictured numbering (1-14) in A corresponds to labeled density bar graph in panel B. B) Anti-angiogenic factors (black) are present at high levels, and pro-angiogenic factors (white) are present in low levels. Mean pixel intensities were determined using image processing software, Image J (NIH, Bethesda, Md.).

After trauma, corneal neovascularization often occurs, which contributes to vision impairment. More specifically, neovascularization may induce tissue scarring, lipid deposition, stromal hemorrhage, and corneal edema, severely altering visual acuity (Maddula et al. 2011). A biochemical evaluation of the protein composition of MSC-S using human angiogenesis protein arrays underscores its negative angiogenic potential (FIG. 14A). Strikingly, the analysis shows the most prominent proteins present in MSC-S have anti-angiogenic roles and are present in 2-7 fold excess of the pro-angiogenic molecules (FIG. 14B). Notably, TIMP-1, a matrix-metalloprotease inhibitor, is present at high levels, which is consistent with reports identifying TIMP-1 as the principal anti-angiogenic modulator produced by MSCs (Zanotti et al. 2016).

MSC-S Exhibits a Negative Angiogenic Potential in a Cell-Based Assay [Study CM19_TFA02]

Figures 15A, 15B:
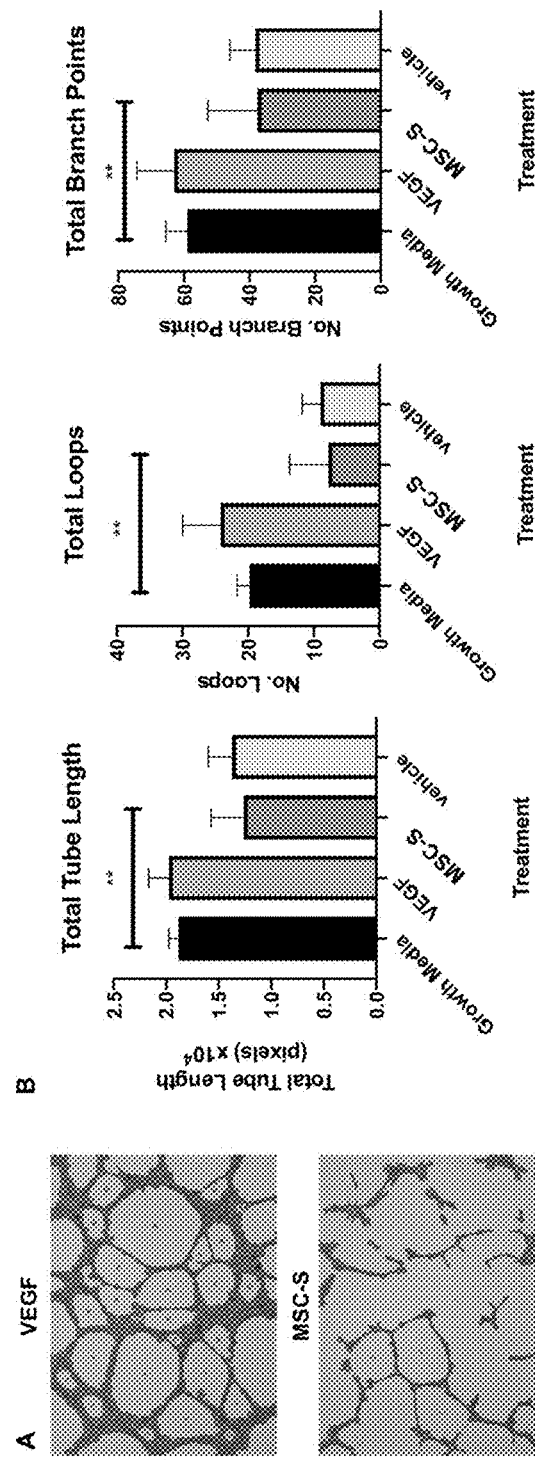
FIG. 15A-FIG. 15B: MSC-S EXHIBITS ANTI-ANGIOGENIC PROPERTIES IN A TUBE FORMATION ASSAY. Matrigel at 12,000 cells in 100 uL of Endothelial Cell Basal media plus Low Serum Growth Supplement (Life Technologies) and in the absence or presence of MSC-S (40 μg/mL). Cells were incubated for 6 hrs to allow endothelial tube formation, followed by image acquisition and processing. Five replicates were performed for each condition. A) Image panels show MSC-S attenuates tube formation relative to VEGF positive control. B) MSC-S reduces angiogenesis metrics: total tube length, total loops, and total branch points. Images processed using Wimasis, 2016. WimTube: Tube Formation Assay Image Analysis Solution. Release 4.0. A two-tailed unpaired t-test was performed using GraphPad Prism version 8.0.0 for Windows, GraphPad Software, San Diego, Calif. USA. Data presented is mean±SE: $**p<0.05$.

While there is no established in vitro cell-based assay to specifically evaluate corneal angiogenesis, the human umbilical vein endothelial cell (HUVEC) tube formation assay is a well-established in vitro model to evaluate angiogenic potential of therapeutic compounds. This assay evaluates the ability of compounds to promote or impair blood vessel formation by measuring the endothelial cell reorganization to form capillary-like vascular structures. Briefly, HUVEC cells are seeded on a thin layer of Matrigel® (BD Biosciences) and incubated in the presence or absence of active drug substance. Within 2-6 hours endothelial cells will divide and begin to form a vascular network if supported by pro-angiogenic molecules. Using this method, we show that the sum collective of factors in MSC-S do not promote angiogenesis, and it attenuates tube formation parameters, such as total tube length, number of branch points, and number of loops (FIG. 15). Comparatively, treatment with vascular endothelial growth factor (VEGF) alone induces a potent pro-angiogenic response.

MSC-S Exhibits Anti-Scarring Properties [CM19_CFS04]

Figure 16:
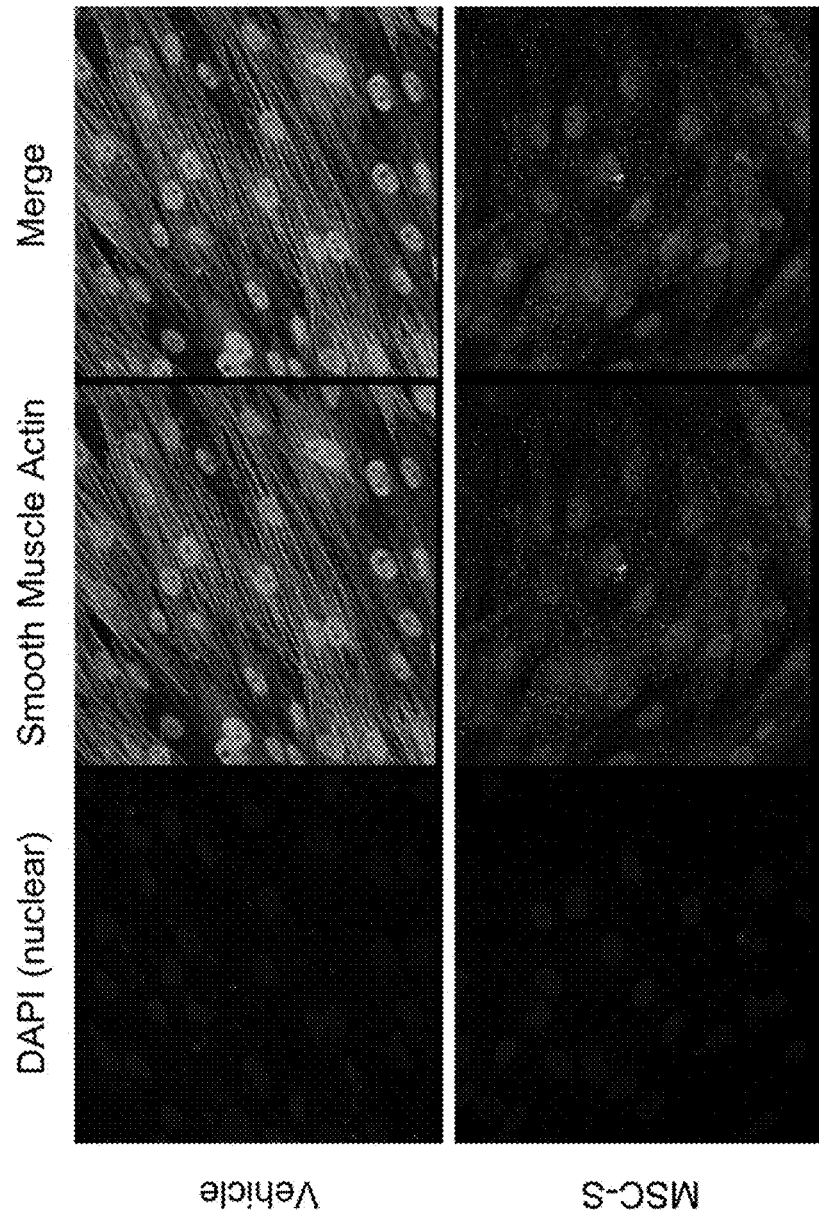
FIG. 16: MSC-S IMPAIRS TGFB-1-INDUCED CORNEAL MYOFIBROBLAST DIFFERENTIATION. Depicted are human primary corneal induced to differentiate into myofibroblasts by treatment with TGFβ-1 in the presence of vehicle buffer or MSC-S (10 μg/mL). After 24 hours, cells were fixed and stained with a nuclear dye (DAPI; blue channel) and for Smooth Muscle Actin (green channel). For all treatment groups, the same imaging and camera setting were applied.

Following corneal trauma, fibroblasts in the stroma differentiate to myofibroblasts, the hallmark of scarring, in a process characterized by dysregulation of several biomarkers. Myofibroblast differentiation can be replicated in vitro using primary corneal fibroblasts and treatment with TGFβ-1, a potent inducer of differentiation (Li, et al 2017). The ability of MSC-S to impair differentiation was evaluated using immunofluorescent staining for the key scarring biomarker, Smooth Muscle Actin (SMA), which is strongly upregulated during myofibroblast differentiation. Our data show MSC-S has a potent effect and decreases the expression of SMA (FIG. 16), indicating the inhibition of myofibroblast differentiation, and therefore exhibits the ability to impair or prevent scarring.

In Vivo Pharmacology
14-Day Brown Norway Rat Cornea Alkali Burn Dose-Ranging Study [Study COMB.002]

To determine efficacious dosing strength and regimen for a topical ocular formulation of MSC-S, a 14-day dose-ranging study was conducted for the amelioration of alkali-induced corneal injury in Brown Norway rats. Corneal alkali burns were placed in the right eye of Brown-Norway rats (approximately 150 g, 12 weeks old) and animals treated with 5 µL of Vehicle (Hydroxypropyl methylcellulose [HPMC], n=9) or 5 µL MSC-S (0.6 µg/mL, n=8; 6 µg/mL, n=10; 60 µg/mL, n=8) 3× daily or 6 µg/mL MSC-S 6× (n=9) daily as outlined in Table 4 below.

The alkali chemical burn model was selected as the primary in vivo efficacy model as it is the most clinically-relevant to the severity of the indications that MSC-S is intended to treat, given its severe corneal pathologies (Chen et al. 2016; Choi, Choi, and Joo 2011; Kim et al. 2015).

Perforations in the corneal epithelium negatively impacts visual acuity and also causes the cornea to be susceptible to infection (Akpek and Gottsch 2003). Increasing the rate of re-epithelialization is therefore important as it decreases the likelihood that patients will develop an ocular infection or result in other issues such as corneal melting. Ocular treatments seeking to enhance corneal epithelial wound closure by modulating cellular proliferation, migration, and adhesion are vital therefore the rate of 100% wound closure was evaluated.

Cornea opacification and corneal neovascularization were additionally evaluated as they are predictable parameters for detecting the activity of test agents in corneal alkali injury models with higher levels relating to vision loss (Epstein et al. 1987; Schrage et al. 2002).

TABLE 4

A 14-day cornea alkali burn study in rats

| Group | Treatment | Treatment Details | Assessment |
|---|---|---|---|
| 1 | HPMC (control) n = 9 | Unilateral topical instillation to right eyes only, 3× daily, days 1-10 (5 µl/instillation) | Quantification of initial corneal wound size by fluorescein staining on Day 1 prior to the first dose administration; Body weights at baseline and on Days 1-4 and Days 7-14; Quantification of corneal wound closures by fluorescein staining on Days 2-4 at 1 hour after the first dose administration; Clinical scoring of corneal opacity and neovascularization on Days 2-4 and Days 7-14 at 1 hour after the first dose administration; |
| 2 | MSC-S 0.6 µg/mL n = 8 | | |
| 3 | MSC-S 6 µg/mL n = 10 | | |
| 4 | MSC-S 60 µg/mL n = 8 | | |
| 5 | MSC-S 6 µg/mL n = 9 | Unilateral topical instillation to right eyes only, 6× daily, Days 1-10 (5 µl/instillation) | Digital images without fluorescein taken on Days 7 and 14; Collection and fixation of whole eyes on Day 15 |

HPMC: hydroxypropyl methycellulose
Vehicle consisted of sodium phosphate, mannitol, 2% HPMC pH 7.4

Study Results

The application of alkali to the cornea induced a severe chemical burn in all eyes to which it was applied. Deaths occurred within each group prior to scheduled termination. The frequency of animal death did not correlate to any single treatment and did not affect the overall efficacy comparisons between the groups; 3, 2, 4, 1 and 2 early deaths occurred in Groups 1, 2, 3, 4 and 5, respectively yielding a total of 6, 6, 6, 7 and 7 animals remaining for evaluation on Day 14. Mean body weight trends were consistent across all treatment arms, with a decline in daily body weights from Day 1 to Day 7, and a subsequent gradual increase in daily body weights from Day 8 to Day 14.

Figures 17A, 17B:
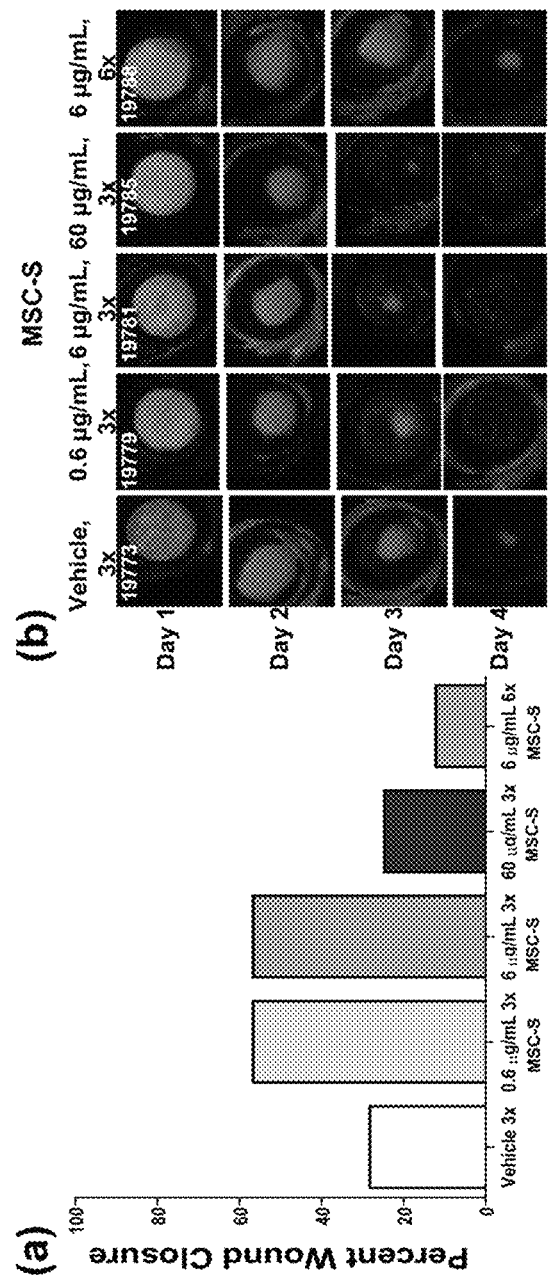
FIG. 17A-FIG. 17B: MSC-S TREATMENT ACCELERATES WOUND CLOSURE. Corneal alkali burns were placed in the right eye of Brown-Norway rats (approximately 150 g, 12 weeks old) and animals treated with 5 μL of Vehicle (HPMC, n=7) or MSC-S (0.6 μg/mL, n=7; 6 μg/mL, n=7; 60 μg/mL, n=8) 3× daily or 6 μg/mL MSC-S 6× (n=8) daily. Data from Day 4 are shown with percent wound closure exhibited in panel (a) and representative fluorescein staining shown in panel (b). The animal identification number is shown in white in the top left-hand corner. The extent of wound closure was evaluated via fluorescein staining by the ratio of the difference between the immediate insult and the remaining wound area.

Alkali burning induced very apparent severe corneal damage including severe epithelial wounds, neovascularization and opacification. Topical application, 3× daily, of MSC-S to corneal alkali burn injury-induced eyes led to complete (i.e. 100%) wound closure in 57% of eyes treated with 0.6 and 6 µg/mL on Day 4 compared to 27% of eyes treated with Vehicle and 60 µg/mL MSC-S (FIG. 17a). In comparison, eyes treated with 6 µg/mL MSC-S, 6× daily resulted in a 12.5% wound closure rate. Fluorescein angiograms denoting corneal injury from representative eyes from each of the treatment groups are shown in FIG. 17b. Eyes treated with 0.6, 6 and 60 µg/mL MSC-S 3× daily exhibit smaller wounds on Day 3 compared to the Vehicle control administered 3× daily and 6 µg/mL MSC-S administered 6× daily. The increased dosing application of 6 µg/mL MSC-S, from 3× daily to 6× daily, did not result in an increase in activity and instead yielded results comparable to Vehicle. This may have been a result of increased irritation at the wound site.

Figures 18A, 18B:
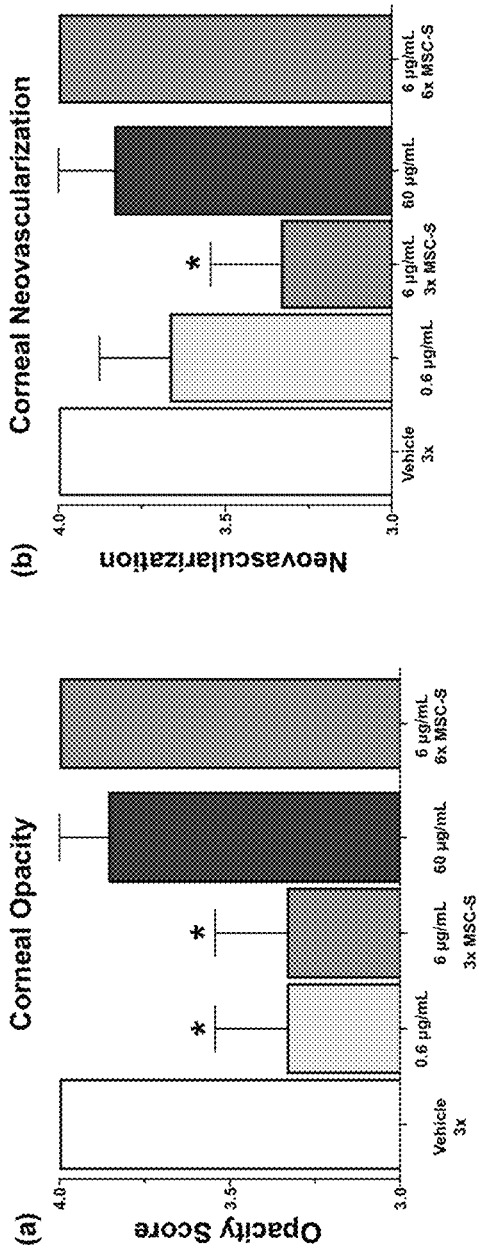
FIG. 18A-FIG. 18B: MSC-S TREATMENT SIGNIFICANTLY IMPROVES CORNEAL OPACITY AND NEOVASCULARIZATION. The corneal opacity (A) and neovascularization (B) data of corneal burns treated with 5 μL of Vehicle (HPMC, n=6) or MSC-S (0.6 μg/mL, n=6; 6 μg/mL, n=6; 60 μg/mL, n=6) 3× daily or 6 μg/mL MSC-S (n=7) 6× daily for 10 days are displayed. Corneal opacity on a scale of 0-4. 0=completely clear; 1=slightly hazy, iris and pupil easily visible; 2=slightly opaque, iris and pupil still detectable; 3=opaque, pupils hardly detectable; and 4=completely opaque with no view of the pupil. Neovascularization on a scale of 0-4. 0=no neovessels; 1=neovessels at limbus; 2=neovessels spanning limbus; 3=neovessels reaching the corneal center with remaining clear zones elsewhere in the cornea; 4=neovessels in all four quadrants of the cornea, including the corneal center. Data are expressed as mean with standard error. Comparisons of parameters were performed using a one-way analysis of variance followed by a post-hoc Bonferroni test. A *P value of <0.05 was considered statistically significant (GraphPad Prism version 8.0.0 for Windows, GraphPad Software, San Diego, Calif. USA).
Figures 19A, 19B:
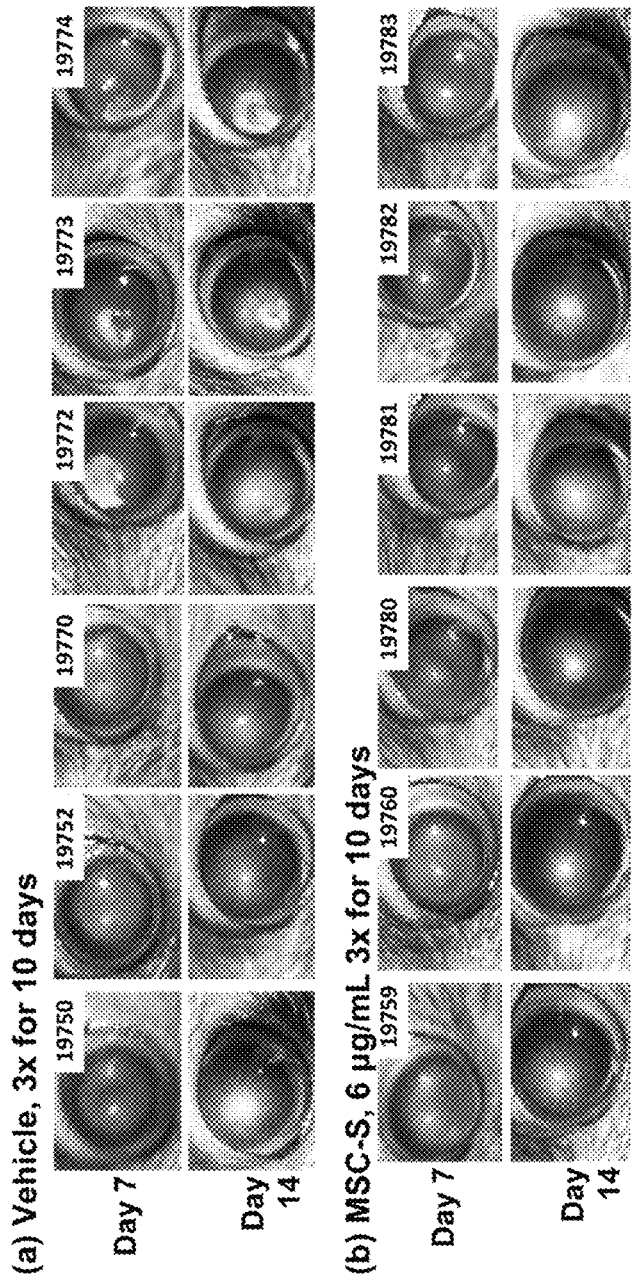
FIG. 19A-FIG. 19B: MSC-S AT 6 µg/mL IS MARKEDLY SUPERIOR TO VEHICLE IN AMELIORATING THE EFFECTS OF CORNEAL INJURY. Changes in corneal damage during topical application (5 µL) of Vehicle (a) and 6 µg/mL MSC-S(b) 3× daily for 10 days in corneal alkali injury-induced rats. Digital images of the eyes were obtained on Days 7 and 14 to document the clinical appearance of the eyes. The animal identification number is shown in the top right-hand corner of each rat composite.
Figure 20:
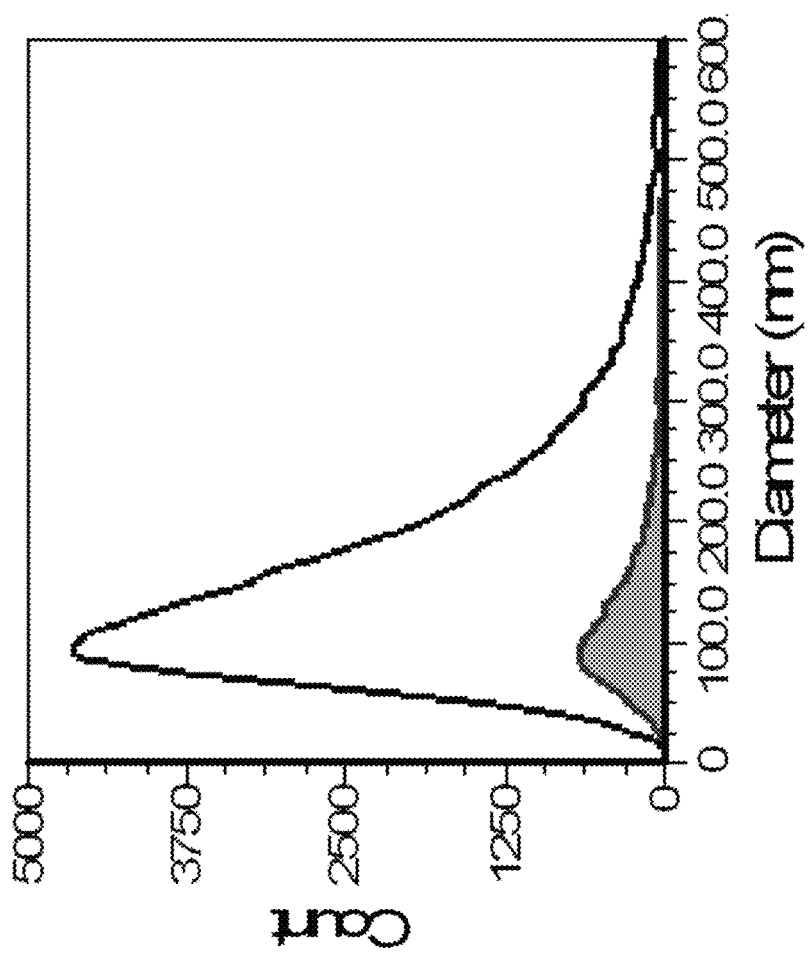
FIG. 20: Size Distribution of EVs. Shaded area is particles remaining after detergent treatment, indicating >85% of particles are detergent-labile lipid based vesicles.

MSC-S significantly decreased corneal opacity when topically administered at 0.6 and 6 µg/mL 3× daily and neovascularization when administered at 6 µg/mL 3× daily (FIG. 18). The opacity scores for the 3× daily 0.6 and 6 µg/mL MSC-S groups were both 3.33±0.21 compared to 4.0±0 (level 4 being the highest opacity level) and 3.86±0.14 for the Vehicle and 60 µg/mL MSC-S groups and then 4.0±0 for 6 µg/mL MSC-S delivered 6× daily for 10 days. All MSC-S 3× daily groups yielded lower corneal neovascularization scores compared to the Vehicle 3× daily control group of 4.0±0 (level 4 being the highest neovascularization level) with the 6 µg/mL dosing group delivered 3× daily the most effective at 3.33±0.21 followed by 0.6 µg/mL MSC-S at 3.67±0.21 and 60 µg/mL MSC-S at 3.83±0.17. The 6 µg/mL MSC-S delivered 6× daily was no more active than the Vehicle control at 3× daily.

Overall, administration of MSC-S at 0.6 or 6 µg/mL 3× daily for 10 days exhibited enhanced wound healing activity compared to Vehicle. However, some of the positive effects of MSC-S may have been masked by a limitation of the dynamic range of the scoring parameters applied in this study which are necessary to discern differences between groups. As shown in FIGURE, the individual eyes of the 6 µg/mL MSC-S 3× daily and Vehicle treated groups on Days 7 and 14 depict a marked difference in wound healing. All of the MSC-S treated eyes show recovery from the corneal injury while half of the Vehicle treated eyes still exhibit the severe signs of corneal damage on Day 14.

In conclusion, MSC-S at 0.6 or 6 µg/mL MSC-S administered topically 3× daily enhanced wound closure and reduced corneal opacity and neovascularization in a rodent model of corneal burn wounds. These results suggest that MSC-S may be a potential therapeutic agent for corneal re-epithelialization after corneal trauma. As an illustrative example, a typical dosing drop (20-30 uL) will contain 120-180 ng of drug product.

In Vitro Irritancy
Evaluation of the Eye Irritation Potential of Topically Applied Formulations Using the EpiOcular Human Tissue Model [Study 046-19]

An in vitro irritancy study was conducted using EpiOcular tissue to assess the eye irritancy potential of MSC-S. MSC-S was formulated at the proposed clinical concentration of 6

μg/mL as per Table 3 and compared to vehicle control (formulation solution without MSC-S). EpiOcular tissue was exposed to the treatment groups for 3, 30, and 60 minutes and the viability of treated tissues was assessed using the MTT (3-[4,5-dimethylthiazol-2-yl]-2,5-diphenyltetrazolium bromide; thiazolyl blue) viability tissue test to calculate the $ET_{50}$. Ultrapure water was used as the control and was exposed to EpiOcular tissue for 60 minutes prior to tissue viability assessment.

At 60 minutes of exposure, all test articles were categorized as non-irritating. A summary of the results is provided in Table 5.

TABLE 5

EpiOcular $ET_{50}$ results

| Test Article | $ET_{50}$ (minutes) | Possible Draize Score | Category |
| --- | --- | --- | --- |
| MSC-S-pH 7.4 | >60 | <8.4 | Non-irritating, minimal |
| Vehicle, pH 7.4 | >60 | <8.4 | Non-irritating, minimal |

$ET_{50}$: exposure needed for a test article to reduce the viability of treated tissue to 50% of control tissue Repeat Dose Studies A repeat-dose non GLP dose range finding study was conducted in rats to identify doses to investigate in the formal GLP rabbit toxicology study. To match the treatment duration of the clinical study, a 14-day GLP toxicology study following ocular instillation of MSC-S was conducted in rabbits. The rabbit was chosen as the toxicology species due to anatomical similarity to human eyes; 13 mm rabbit corneal diameter versus 11 mm corneal diameter in humans and decreased blink rate; every 6 minutes in rabbits compared to every 5 seconds in humans. Rapid clearance occurs following topical ocular application, due in part to test agent drainage, blinking, tear film and tear film turn over. Therefore, to fully assess any potential toxicities the residence time of MSC-S on the eye was maximized by utilizing the rabbit which has a substantially slower blink rate compared to humans (Vézina 2012).

An Ocular Tolerability Study of MSC-S Following Repeated Ocular Instillation for Seven Days in Brown Norway Rats [Study COMB.004]

The ocular tolerability of MSC-S (6 μg/mL) was evaluated in a repeated 7-day study in Brown Norway rats (~12 weeks old) following 3× a day (9 AM, 1 PM and 5 PM, 5 μL/instillation), or 6× a day (7 AM, 9 AM, 11 AM, 1 PM 3 PM, and 5 PM; 5 μL/instillation) bilateral topical instillation and compared to 3× per day with Vehicle (1% HPMC) (n=1/group). At approximately 30 minutes following the final daily dose administration, ocular tolerability was assessed by Draize scoring of chemosis, hyperemia, and discharge on Day 1 to Day 7.

All animals survived to their scheduled termination. No chemosis, hyperemia, or discharge was observed following delivery of any of the test groups in this study. Therefore, topical administration of MSC-S (6 μg/mL) either 3× a day (up to 0.09 μg of MSC-S), or 6× a day (up to 0.18 μg of MSC-S), for seven days is well tolerated in Brown Norway rats.

A 14-Day Repeat Dose Toxicity Study of MSC-S in Rabbits Following Topical Ocular Administration (GLP) [Study p19-0838-00b]

The purpose of the study was to determine the ocular and systemic toxicity of MSC-S following repeated topical ocular application for two weeks in Dutch belted rabbits. The rabbit eye is anatomically similar to the human eye; 13 mm rabbit corneal diameter versus 11 mm corneal diameter in humans and the slower blink rate in the rabbit (every 6 minutes compared to every 5 seconds in humans) allows a greater residence time of MSC-S on the eye thereby allowing a rigorous assessment of safety (Vézina 2012).

Nine male Dutch belted rabbits (18-28 weeks old) was administered MSC-S (6 μg/mL, 30 μL each dose) via topical ocular instillation to the right eye for three times a day (low dose; n=4) or six times a day (high dose; n=5) for two weeks with a one week recovery period. The day of initial dosing was defined as Day 0. The left eye served as a contralateral control and received vehicle; 100 mM sodium phosphate, 0.4% mannitol, 2% HPMC, pH 7.4 at the same frequency as the right MSC-S-treated eye. The low (3×/daily) and high doses (6×/daily) were administered approximately 4 and 2 hours apart, respectively.

Rabbits were sacrificed on Day 15 (4 animals for the low dose and 3 animals for the high dose; 24 hours after the last dose) or Day 22 (2 animals for the high dose; 168 hours after the last dose). Toxicity was assessed based on mortality, clinical observations (twice daily), body weight (pre-dose, weekly and at termination), ophthalmic examinations, intraocular pressure (pre-dose and at termination), clinical pathology (hematology, clinical chemistry, and coagulation; pre-dose and at termination), gross pathology, organ weights, and ocular histopathology. Ophthalmic examinations of all eyes were performed by a board-certified veterinary ophthalmologist; slit-lamp biomicroscopy with McDonald-Shaddack Scoring Systems and Ocular Posterior Segment Scoring Scale and indirect ophthalmoscopy, at pre-dose and then on Days 1, 3, 14 and at termination.

All rabbits survived to their scheduled sacrifice. No gross lesions and abnormalities were recorded. There were no test article-related findings on body weight, intraocular pressure, clinical pathology, gross pathology, organ weights, ophthalmologic examination or histopathology.

In conclusion, repeated daily topical administration of 6 μg/mL of MSC-S, at both three times a day and six times a day for 14 days was safe and well-tolerated and supports the clinical investigation of 6 μg/mL three times a day for 14 days of MSC-S.

Effects in Humans

MSC-S will be tested in human subjects. The dose selection for the First-in-Human study has been based on multiple factors.

Justification for Dose

Dosing MSC-S three times daily (TID) at 6 μg/mL via topical instillation is predicted to be safe for human eyes, and the selected concentration is supported by in vivo animal studies as being effective and safe. MSC-S tolerability rabbit study (two-week dosing, followed by one week recovery period), as well as a pharmacological activity rodent study, were performed to identify appropriate doses for human treatment. In the rat chemical burn model, MSC-S at both 0.6 μg/mL and 6 μg/mL (three times daily) enhanced corneal wound healing; both 0.6 μg/mL and 6 μg/mL administer three times daily resulted in significantly reduced corneal opacity compared to vehicle, and 6 μg/mL administered three times daily significantly reduced neovascularization compared to vehicle control [Study COMB.002]. Further, no adverse effects are observed at 6 μg/mL of clinical formulation of MSC-S administered to healthy rabbit eyes three or six times daily, for 14 days [Study p19-0838-00b].

Topical ophthalmic drug development is impeded by many anatomical constraints including tear turnover and dilution, nasolachrymal drainage, and reflex blinking with often less than 5% of the topically administered dose reaching deeper ocular tissues (Gaudana et al., 2009). The residence time of the formulated therapeutic on the cornea may be too limited therefore the rabbit was chosen as the toxicologic species in which to evaluate the safety of MSC-S, as the rabbit exhibits a slower blink rate (every 6 minutes compared to every 5 seconds in humans, (Vézina 2012)) thereby allowing a greater residence time of MSC-S on the eye and resulting in a rigorous assessment of safety. Moreover, in the rabbit study, the MSC-S formulation utilized a higher concentration of the HPMC viscous and mucoadhesive polymers to increase residence time and increase ocular penetration. Assuming a comparable dosage drop, the corneal surface MSC-S concentration is therefore expected to be higher in rabbits than in humans, and since no adverse effects occur in rabbit eyes and we anticipate the MSC-S concentration to be lower in human eyes (due to increased blink rate), a dose of 6 µg/mL (TID) in humans is justified as safe.

Indications, Usage, Dosage Forms

MSC-S is indicated for the treatment of chemical burns of the cornea and/or Persistent Corneal Epithelial Defects (PCED). The dosage form of MSC-S is a sterile ophthalmic solution. MSC-S will be administered three times per day via topical instillation as a single drop to the eye (approximately 30 µL/drop). The concentration of MSC-S will be 6 µg/mL. Additionally, 6 µg/mL was shown to significantly improve corneal wound healing in a chemical burn rat model following three doses per day over 10 days, and exhibited no adverse effects when applied to the eyes of healthy rabbits up to 6× per day for 14 days.

REFERENCES

Akpek, E. K., and J. D. Gottsch. 2003. "Immune Defense at the Ocular Surface." *Eye* (London, England) 17 (8): 949-56. https://doi.org/10.1038/sj.eye.6700617.

Baradaran-Rafii, Alireza, Medi Eslani, Zeeshan Haq, Ebrahim Shirzadeh, Michael J. Huvard, and Ali R. Djalilian. 2017. "Current and Upcoming Therapies for Ocular Surface Chemical Injuries." *The Ocular Surface* 15 (1): 48-64. https://doi.org/10.1016/j.jtos.2016.09.002.

Chen, Yanfeng, Wenzhao Yang, Xiaobo Zhang, Shu Yang, Gao Peng, Ting Wu, Yueping Zhou, et al. 2016. "MK2 Inhibitor Reduces Alkali Burn-Induced Inflammation in Rat Cornea." *Scientific Reports* 6 (June): 28145. https://doi.org/10.1038/srep28145.

Choi, Jin A., Jun-Sub Choi, and Choun-Ki Joo. 2011. "Effects of Amniotic Membrane Suspension in the Rat Alkali Burn Model." *Molecular Vision* 17 (February): 404-12.

Epstein, R. J., R. D. Stulting, R. L. Hendricks, and D. M. Harris. 1987. "Corneal Neovascularization. Pathogenesis and Inhibition." *Cornea* 6 (4): 250-57. https://doi.org/10.1097/00003226-198706040-00004.

Femandes-Cunha, Gabriella Maria, Kyung-Sun Na, Ilham Putra, Hyun Jong Lee, Sarah Hull, Yu-Chia Cheng, Ignacio Jesus Blanco, Medi Eslani, Ali R Djalilian, and David Myung. 2019. "Corneal Wound Healing Effects of Mesenchymal Stem Cell Secretome Delivered within a Viscoelastic Gel Carrier." *Stem Cells Translational Medicine* 8 (5): 478-89.

Ferreira, Joana R, Graciosa Q Teixeira, Susana G Santos, Mário A Barbosa, Graca Almeida-Porada, and Raquel M Gongalves. 2018. "Mesenchymal Stromal Cell Secretome: Influencing Therapeutic Potential by Cellular Pre-Conditioning." *Frontiers in Immunology* 9.

Gaudana R, Jwala J, Boddu S H, Mitra A K. 2009. "Recent perspectives in ocular drug delivery." *Pharm Res.* 26(5): 1197-216

Harkin, Damien G, Leanne Foyn, Laura J Bray, Allison J Sutherland, Fiona J Li, and Brendan G Cronin. 2015. "Concise Reviews: Can Mesenchymal Stromal Cells Differentiate into Corneal Cells? A Systematic Review of Published Data." *Stem Cells* 33 (3): 785-91.

Katzman, Lee R, and Bennie H Jeng. 2014. "Management Strategies for Persistent Epithelial Defects of the Cornea." *Saudi Journal of Ophthalmology: Official Journal of the Saudi Ophthalmological Society* 28 (3): 168-72. https://doi.org/10.1016/j.sjopt.2014.06.011.

Kim, Dae Won, Sung Ho Lee, Min Jea Shin, Kibom Kim, Sae Kwang Ku, Jong Kyu Youn, Su Bin Cho, et al. 2015. "PEP-1-FK506BP Inhibits Alkali Burn-Induced Corneal Inflammation on the Rat Model of Corneal Alkali Injury." *BMB Reports* 48 (11): 618-23. https://doi.org/10.5483/bmbrep.2015.48.11.041.

Li M, Luan F, Zhao Y, Hao H, Liu J, Dong L, Fu X, Han W. "Mesenchymal stem cell-conditioned medium accelerates wound healing with fewer scars." *Int Wound J.* 2017, 14:64-73.

Maddula, Surekha, Don K. Davis, Soumya Maddula, Michael K. Burrow, and Balamurali K. Ambati. 2011. "Horizons in Therapy for Corneal Angiogenesis." *Ophthalmology* 118 (3): 591-99. https://doi.org/10.1016/j.ophtha.2011.01.041.

McGwin, Gerald, and Cynthia Owsley. 2005. "Incidence of Emergency Department-Treated Eye Injury in the United States." *Archives of Ophthalmology* 123 (5): 662-66.

Samaeekia, Ravand, Behnam Rabiee, Ilham Putra, Xiang Shen, Young Jae Park, Peiman Hematti, Medi Eslani, and Ali R Djalilian. 2018. "Effect of Human Corneal Mesenchymal Stromal Cell-Derived Exosomes on Corneal Epithelial Wound Healing." *Investigative Ophthalmology & Visual Science* 59 (12): 5194-5200.

Schrage, Norbert Franz, Sirpa Kompa, Wolfram Haller, and Stephanie Langefeld. 2002. "Use of an Amphoteric Lavage Solution for Emergency Treatment of Eye Burns. First Animal Type Experimental Clinical Considerations." *Burns: Journal of the International Society for Burn Injuries* 28 (8): 782-86. https://doi.org/10.1016/s0305-4179(02)00194-8.

Serrano, Felipe, Lawrence B Stack, R Jason Thurman, Lara Phillips, and Wesley H Self. 2013. "Traumatic Eye Injuries: Management Principles for the Prehospital Setting." *JEMS: A Journal of Emergency Medical Services* 38 (12): 56.

Singh, Parul, Manoj Tyagi, Yogesh Kumar, K K Gupta, and P D Sharma. 2013. "Ocular Chemical Injuries and Their Management." *Oman Journal of Ophthalmology* 6 (2): 83-86. https://doi.org/10.4103/0974-620X. 116624.

Vézina, Mark. 2012. "Comparative Ocular Anatomy in Commonly Used Laboratory Animals." In *Assessing Ocular Toxicology in Laboratory Animals,* 1-21. Springer.

Vizoso, Francisco J, Noemi Eiro, Sandra Cid, Jose Schneider, and Roman Perez-Fernandez. 2017. "Mesenchymal Stem Cell Secretome: Toward Cell-Free Therapeutic Strategies in Regenerative Medicine." *International Journal of Molecular Sciences* 18 (9): 1852.

Zanotti, L., R. Angioni, B. Cali, C. Soldani, C. Ploia, F. Moalli, M. Gargesha, et al. 2016. "Mouse Mesenchymal Stem Cells Inhibit High Endothelial Cell Activation and Lymphocyte Homing to Lymph Nodes by Releasing TIMP-1." *Leukemia* 30 (5): 1143-54. https://doi.org/10.1038/leu.2016.33.

Ziaei, Mohammed, Carol Greene, and Colin R Green. 2018. "Wound Healing in the Eye: 50 Therapeutic Prospects." *Advanced Drug Delivery Reviews* 126: 162-76.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method of treatment for an ocular condition in a subject in need thereof comprising administering to the subject a bone marrow-derived mesenchymal stem cell (MSC) secretome composition, wherein the MSC secretome composition comprises: HGF; Pentraxin-3 (TSG-14); VEGF; TIMP-1; Serpin E1; and <5 ng/mL IL-8.

2. The method of treatment according to claim 1, wherein the MSC secretome composition further comprises:
   i. at least one trophic factors/cytokines selected from the group consisting of TIMP-2, and VEGF-A;
   ii. at least one additional factor selected from the group consisting of PEDF (Serpin F1), IGFBP-2, IGFBP-3, SDF-1, Kallikrein 3, MCP-1, Angiogenin, MCP-2, Angio-2, IL-6, IL-17, G-CSF, M-CSF, GM-CSF, IL-8, TNF-beta, and PDGF; and
   iii. at least one additional factor selected from the group consisting of DPPIV (dipeptidyl peptidase-4), uPA, Angiopoietin-1, Angiopoietin-2, Amphiregulin, Endostatin, Endothelin-1, Thrombospondin-2, and Thrombospondin-1.

3. The method of treatment according to claim 2, wherein the MSC secretome composition comprises 1 ng/mL-100 ng/mL of at least one factor selected from the group consisting of Serpin E1, TIMP-1, Thrombospondin-1, Pentraxin-3 (TSG-14), and Serpin F1.

4. The method of treatment according to claim 2, wherein the MSC secretome composition comprises 400 pg/mL-3000 pg/mL of at least one factor selected from the group consisting of Angiopoietin-1, Angiopoietin-2, Amphiregulin, Endostatin, Endothelin-1, Thrombospondin-2, Thrombospondin-1, Angiogenin, DPPIV, IGFBP-3, and uPA.

5. The method of treatment according to claim 2, wherein the MSC secretome composition further comprises at least one factor selected from the group consisting of Apolipoprotein A1, Complement Factor D, C-reactive protein, Cystatin C, DKK-1, Emmprin, Osteopontin, vitamin D BP, MIF, RANTES, uPAR, IL-17a, GDF-15, and IFNγ.

6. The method of treatment according to claim 2, wherein the MSC secretome composition comprises ratios of anti-angiogenic to pro-angiogenic wherein the ratio is >2, >3, >4, or >5.

7. The method of treatment according to claim 2, wherein the MSC secretome comprises 1 pg/mL-400 pg/mL of VEGF.

8. The method of treatment according to claim 2, wherein the level of VEGF is 5-10 fold lower than the level of Serpin E1.

9. The method of treatment according to claim 2, wherein the MSC secretome composition comprises one or more anti-angiogenic factor, and wherein the sum of the concentration of the one or more anti-angiogenic factors relative to the concentration of VEGF is >2, >3, >4, or >5.

10. The MSC secretome composition according to claim 2, wherein the MSC secretome comprises less than 1000 pg/mL of bFGF, PLGF, and PDGF.

11. The method of treatment according to claim 2, wherein the MSC secretome composition has a pH of about 4.7 to about 7.5.

12. The method of treatment according to claim 2, wherein the MSC secretome composition is formulated in a buffer system selected from the group consisting of di/mono sodium phosphate, sodium citrate/citric acid, boric acid/sodium citrate, boric acid/sodium tetraborate, and citric acid/disodium phosphate.

13. The method of treatment according to claim 2, wherein the MSC secretome composition further comprises a tonicity modifying agent.

14. The method of treatment according to claim 13, wherein the tonicity modifying agent is selected from the group consisting of NaCl, KCl, mannitol, dextrose, sucrose, sorbitol, and glycerin.

15. The method of treatment according to claim 2, wherein the MSC secretome composition further comprises mono/di-sodium phosphate, mannitol, and trehalose, and wherein the composition has a pH of about pH 7.4.

16. The method of treatment according to claim 2, wherein the MSC secretome composition further comprises divalent cations.

17. The method of treatment according to claim 16, wherein the divalent cations are selected from the group consisting of Mg2+, Ca2+, and Zn2+.

18. The method of treatment according to claim 2, wherein the MSC secretome composition further comprises di-sodium phosphate/citric acid, mannitol, and trehalose, and wherein the composition has a pH of about pH 6.4.

19. The method of treatment according to claim 2, wherein the MSC secretome composition does not comprise one or more components selected from the group consisting of: xenobiotic components; Phenol red; peptides and biomolecules <3 kDa; antibiotics; protein aggregates >200 nm; cells; non-exosome/non-Extracellular Vesicles cell debris; hormones; and L-glutamine.

20. The method of treatment according to claim 2, wherein the MSC secretome composition comprise an anti-angiogenic MSC secretome or an anti-scarring MSC secretome.

21. The method of treatment according to claim 1, wherein the MSC secretome composition further comprises an agent that increases viscosity.

22. The method of treatment according to claim 21, wherein the adhesive agent is selected from the group consisting of hypromellose, Poloxamer 407, Poloxamer 188, Poloxomer 237, Poloxomer 338, Hypromellose, (HPMC), polycarbophil, polyvinylpyrrolidone (PVP), PVA (polyvinyl alcohol), polyimide, sodium hyaluronate, gellan gum, poly (lactic acid-co-glycolic acid) (PLGA), polysiloxane, polyimide, carboxymethylcellulose (CMC), or hydroxypropyl methylcellulose (HPMC), hydroxy methyl cellulose, hydroxy ethyl cellulose, sodium carboxy methyl cellulose, fibrin glue, polyethyelene glycol, and GelCORE.

23. The method of treatment according to claim 1, wherein the MSC secretome composition comprises:
   i. 0.3-4.5 ng/mL HGF;
   ii. 0.5-20 ng/mL Pentraxin-3 (TSG-14);
   iii. 100-600 pg/mL VEGF;
   iv. 10-200 ng/mL TIMP-1;
   v. 20-80 ng/mL Serpin E1; and
   vi. <5 ng/mL IL-8.

24. A method of treatment for an ocular condition in a subject in need thereof comprising administering to the subject a bone marrow-derived mesenchymal stem cell (MSC) secretome composition, wherein the MSC secretome composition is a stable mesenchymal stem cell (MSC) secretome formulation comprising:
   i. 2 µg-20 µg of MSC secretome per mL;
   ii. 2 mg-3 mg monobasic sodium phosphate per mL;
   iii. 11 mg-12 mg dibasic sodium phosphate per mL;
   iv. 11.5 mg-13 mg mannitol per mL;
   v. 23 mg-24 mg trehalose dihydrate;
   vi. 0.5 mg-2 mg hypromellose per mL; and
   wherein the pH is about 4.7 to about 7.5.

25. A method of treatment for an ocular condition in a subject in need thereof comprising administering to the subject a bone marrow-derived mesenchymal stem cell (MSC) secretome composition, wherein the MSC secretome composition is a stable mesenchymal stem cell (MSC) secretome formulation comprising:
   i. 0.004%-0.08% w/w of MSC secretome
   ii. 4%-5% w/w monobasic sodium phosphate;
   iii. 21.5%-23% w/w dibasic sodium phosphate;
   iv. 23%-25% w/w mannitol;
   v. 46%-48% w/w trehalose dehydrate;
   vi. 1%-3% w/w hypromellose; and
   wherein the pH is about 4.7 to about 7.5.

\* \* \* \* \*